United States Patent
Silbert et al.

(10) Patent No.: US 9,068,953 B2
(45) Date of Patent: Jun. 30, 2015

(54) INTEGRATED ROBOTIC SAMPLE TRANSFER DEVICE

(71) Applicant: AGENA BIOSCIENCE, INC., San Diego, CA (US)

(72) Inventors: Rolf Silbert, Del Mar, CA (US); Richard Capella, La Jolla, CA (US); Justin Cuzens, San Diego, CA (US)

(73) Assignee: Agena Bioscience, Inc., San Diego, CA (US)

( * ) Notice: Subject to any disclaimer, the term of this patent is extended or adjusted under 35 U.S.C. 154(b) by 0 days.

(21) Appl. No.: 13/625,719

(22) Filed: Sep. 24, 2012

(65) Prior Publication Data

US 2013/0017128 A1    Jan. 17, 2013

Related U.S. Application Data

(63) Continuation of application No. 12/211,796, filed on Sep. 16, 2008, now abandoned.

(60) Provisional application No. 60/972,879, filed on Sep. 17, 2007.

(51) Int. Cl.
*B01J 19/00* (2006.01)
*G01N 1/28* (2006.01)
*G01N 35/00* (2006.01)
(Continued)

(52) U.S. Cl.
CPC ... *G01N 35/0099* (2013.01); *B01J 2219/00277* (2013.01); *B01L 3/0244* (2013.01); *B01L 3/0251* (2013.01); *G01N 2035/1037* (2013.01)

(58) Field of Classification Search
CPC .............. B01J 2219/00277; B01L 3/0244; B01L 3/0251
See application file for complete search history.

(56) References Cited

U.S. PATENT DOCUMENTS

| | | |
|---|---|---|
| 2,797,213 A | 6/1957 | Moore |
| 3,046,118 A | 7/1962 | Schmidt |
| 3,046,120 A | 7/1962 | Schmidt |

(Continued)

FOREIGN PATENT DOCUMENTS

| | | |
|---|---|---|
| DE | 3221681 | 12/1993 |
| DE | 19617011 | 4/1996 |

(Continued)

OTHER PUBLICATIONS

NanoPrintTM Microarrayer 60 and 210 slide capacity with plate product information download from http://www.arrayit.com/Products/Microarrayl/NanoPrint/nanoprint.html on May 17, 2007.

(Continued)

*Primary Examiner* — P. Kathryn Wright
(74) *Attorney, Agent, or Firm* — Grant IP, Inc.

(57) ABSTRACT

Embodiments include integrated robotic sample transfer devices and components thereof which are used for reliably and accurately transferring small samples of material from one registered position to another registered position. Such transfers of material may be carried out by a single pin tool or an array of pin tools of a pin tool head assembly of robotic sample transfer devices. Some embodiments also include automated cleaning of the pin tools used to transfer the sample material. Some embodiments are fully integrated units having internal fluid supply and waste tanks, vacuum source, fluid pumps, controllers and user interface devices.

8 Claims, 35 Drawing Sheets

(51) Int. Cl.
*B01L 3/02* (2006.01)
*G01N 35/10* (2006.01)

(56) References Cited

U.S. PATENT DOCUMENTS

| | | |
|---|---|---|
| 3,148,983 A | 9/1964 | Endermann et al. |
| 3,184,310 A | 5/1965 | Fritz et al. |
| 3,201,239 A | 8/1965 | Neugebauer et al. |
| 3,402,044 A | 9/1968 | Steinhoff et al. |
| 3,567,453 A | 3/1971 | Borden |
| 3,568,735 A | 3/1971 | Lancaster |
| 3,776,700 A | 12/1973 | Gallant |
| 3,782,197 A | 1/1974 | Grams |
| 3,807,235 A | 4/1974 | Lefkovitz |
| 3,813,544 A | 5/1974 | Franzen et al. |
| 3,999,689 A | 12/1976 | Ciantro et al. |
| 4,204,117 A | 5/1980 | Aberle et al. |
| 4,214,159 A | 7/1980 | Hillenkamp et al. |
| 4,243,887 A | 1/1981 | Hillenkamp et al. |
| 4,442,354 A | 4/1984 | Hurst et al. |
| 4,458,994 A | 7/1984 | Jain et al. |
| 4,461,328 A | 7/1984 | Kenney |
| 4,491,629 A | 1/1985 | Koike et al. |
| 4,548,245 A | 10/1985 | Crandell et al. |
| 4,550,069 A | 10/1985 | Pampalone |
| 4,554,839 A | 11/1985 | Hewett et al. |
| 4,725,677 A | 2/1988 | Koster et al. |
| 4,731,335 A | 3/1988 | Brigati |
| 4,735,778 A | 4/1988 | Maruyama et al. |
| 4,740,692 A | 4/1988 | Yamamoto et al. |
| 4,779,467 A | 10/1988 | Rainin et al. |
| 4,798,706 A | 1/1989 | Brigati |
| 4,844,298 A | 7/1989 | Ohoka et al. |
| 4,877,745 A | 10/1989 | Hayes et al. |
| 4,882,127 A | 11/1989 | Rosenthal et al. |
| 4,925,629 A | 5/1990 | Schramm |
| 4,931,400 A | 6/1990 | Jitsukawa |
| 4,948,442 A | 8/1990 | Manns |
| 4,952,518 A | 8/1990 | Johnson et al. |
| 5,000,921 A | 3/1991 | Hanaway et al. |
| 5,023,187 A | 6/1991 | Koebler et al. |
| 5,045,694 A | 9/1991 | Beavis et al. |
| 5,055,271 A | 10/1991 | Golias et al. |
| 5,055,408 A | 10/1991 | Higo et al. |
| 5,077,210 A | 12/1991 | Eigler et al. |
| 5,108,703 A | 4/1992 | Pfost et al. |
| 5,118,605 A | 6/1992 | Urdea |
| 5,118,937 A | 6/1992 | Hillenkamp et al. |
| 5,143,854 A | 9/1992 | Pirrung et al. |
| 5,171,989 A | 12/1992 | Williams et al. |
| 5,175,209 A | 12/1992 | Beattie et al. |
| 5,195,657 A | 3/1993 | Wells |
| 5,210,412 A | 5/1993 | Levis et al. |
| 5,221,518 A | 6/1993 | Mills |
| 5,262,128 A | 11/1993 | Leighton et al. |
| 5,279,796 A | 1/1994 | Parker et al. |
| 5,288,644 A | 2/1994 | Beavis et al. |
| 5,300,774 A | 4/1994 | Buttrill |
| 5,312,233 A | 5/1994 | Tanny et al. |
| 5,338,688 A | 8/1994 | Deeg et al. |
| 5,350,676 A | 9/1994 | Oberhardt et al. |
| 5,373,156 A | 12/1994 | Franzen |
| 5,376,788 A | 12/1994 | Standing et al. |
| 5,381,008 A | 1/1995 | Tanner et al. |
| 5,382,793 A | 1/1995 | Weinberger et al. |
| 5,399,501 A | 3/1995 | Pope et al. |
| 5,439,649 A | 8/1995 | Tseung et al. |
| 5,457,041 A | 10/1995 | Ginaven et al. |
| 5,498,545 A | 3/1996 | Vestal |
| 5,503,980 A | 4/1996 | Cantor |
| 5,504,326 A | 4/1996 | Reilly et al. |
| 5,505,916 A | 4/1996 | Berry, Jr. |
| 5,506,348 A | 4/1996 | Pieles |
| 5,510,613 A | 4/1996 | Reilly et al. |
| 5,512,295 A | 4/1996 | Kornberg et al. |
| 5,514,548 A | 5/1996 | Krebber et al. |
| 5,525,812 A | 6/1996 | Bandzuch et al. |
| 5,547,835 A | 8/1996 | Koster |
| 5,550,004 A | 8/1996 | Honda |
| 5,558,983 A | 9/1996 | Simpson et al. |
| 5,561,029 A | 10/1996 | Fitzgerald et al. |
| 5,567,569 A | 10/1996 | Aviram et al. |
| 5,580,434 A | 12/1996 | Robotti et al. |
| 5,580,733 A | 12/1996 | Levis et al. |
| 5,589,136 A | 12/1996 | Northrup et al. |
| 5,591,969 A | 1/1997 | Park et al. |
| 5,599,500 A | 2/1997 | Jones |
| 5,601,982 A | 2/1997 | Sargent et al. |
| 5,605,662 A | 2/1997 | Heller et al. |
| 5,605,798 A | 2/1997 | Koster et al. |
| 5,607,816 A | 3/1997 | Fitzgerald et al. |
| 5,609,907 A | 3/1997 | Natan |
| 5,612,000 A | 3/1997 | Lemieux |
| 5,612,002 A | 3/1997 | Cody et al. |
| 5,614,153 A | 3/1997 | Homberg |
| 5,622,824 A | 4/1997 | Koster |
| 5,631,134 A | 5/1997 | Cantor |
| 5,643,800 A | 7/1997 | Tarantino et al. |
| 5,658,802 A | 8/1997 | Hayes et al. |
| 5,660,792 A | 8/1997 | Koike |
| 5,663,242 A | 9/1997 | Ghosh et al. |
| 5,670,322 A | 9/1997 | Eggers et al. |
| 5,670,381 A | 9/1997 | Jou et al. |
| 5,677,195 A | 10/1997 | Winkler et al. |
| 5,688,642 A | 11/1997 | Chrisey et al. |
| 5,691,141 A | 11/1997 | Koster |
| 5,700,642 A | 12/1997 | Monforte et al. |
| 5,716,825 A | 2/1998 | Hancock et al. |
| 5,742,049 A | 4/1998 | Holle et al. |
| 5,743,960 A | 4/1998 | Tisone |
| 5,746,373 A | 5/1998 | Sanada |
| 5,756,050 A | 5/1998 | Ershow et al. |
| 5,757,392 A | 5/1998 | Zhang |
| 5,770,151 A | 6/1998 | Roach et al. |
| 5,770,272 A | 6/1998 | Biemann et al. |
| 5,770,860 A | 6/1998 | Franzen |
| 5,777,324 A | 7/1998 | Hillenkamp |
| 5,795,714 A | 8/1998 | Cantor et al. |
| 5,807,522 A | 9/1998 | Brown et al. |
| 5,812,272 A | 9/1998 | King et al. |
| 5,828,063 A | 10/1998 | Koster et al. |
| 5,830,655 A | 11/1998 | Monforte et al. |
| 5,837,860 A | 11/1998 | Anderson et al. |
| 5,851,765 A | 12/1998 | Koster |
| 5,854,486 A | 12/1998 | Dreyfus |
| 5,864,137 A | 1/1999 | Becker et al. |
| 5,869,240 A | 2/1999 | Patterson |
| 5,869,242 A | 2/1999 | Kamb |
| 5,872,003 A | 2/1999 | Koster |
| 5,872,010 A | 2/1999 | Karger et al. |
| 5,885,775 A | 3/1999 | Haff et al. |
| 5,894,063 A | 4/1999 | Hutchens et al. |
| 5,900,481 A | 5/1999 | Lough et al. |
| 5,925,520 A | 7/1999 | Tully et al. |
| 5,927,547 A | 7/1999 | Papen et al. |
| 5,928,906 A | 7/1999 | Koster et al. |
| 5,955,729 A | 9/1999 | Nelson et al. |
| 5,957,167 A | 9/1999 | Feygin |
| 5,965,363 A | 10/1999 | Monforte et al. |
| 5,969,350 A | 10/1999 | Kerley et al. |
| 5,981,185 A | 11/1999 | Matson et al. |
| 5,985,356 A | 11/1999 | Schultz et al. |
| 6,022,688 A | 2/2000 | Jurinke et al. |
| 6,024,925 A | 2/2000 | Little et al. |
| 6,040,193 A | 3/2000 | Winkler et al. |
| 6,051,378 A | 4/2000 | Monforte et al. |
| 6,063,339 A | 5/2000 | Tisone et al. |
| 6,074,823 A | 6/2000 | Koster et al. |
| 6,079,283 A | 6/2000 | Papen et al. |
| 6,083,762 A | 7/2000 | Papen et al. |
| 6,090,558 A | 7/2000 | Butler et al. |
| 6,101,946 A | 8/2000 | Martinsky |
| 6,103,518 A | 8/2000 | Leighton |
| 6,104,028 A | 8/2000 | Hunter et al. |

(56) References Cited

U.S. PATENT DOCUMENTS

| | | |
|---|---|---|
| 6,110,426 A | 8/2000 | Shalon et al. |
| 6,111,251 A | 8/2000 | Hillenkamp |
| 6,116,297 A | 9/2000 | Feygin |
| 6,121,048 A | 9/2000 | Zaffaroni et al. |
| 6,133,436 A | 10/2000 | Koster et al. |
| 6,136,269 A | 10/2000 | Winkler et al. |
| 6,143,031 A | 11/2000 | Knothe et al. |
| 6,146,854 A | 11/2000 | Koster et al. |
| 6,159,425 A | 12/2000 | Edwards et al. |
| 6,193,939 B1 | 2/2001 | Kozlowski |
| 6,194,144 B1 | 2/2001 | Koster |
| 6,197,498 B1 | 3/2001 | Koster |
| 6,207,370 B1 | 3/2001 | Little et al. |
| 6,221,601 B1 | 4/2001 | Koster et al. |
| 6,221,605 B1 | 4/2001 | Koster |
| 6,225,061 B1 | 5/2001 | Becker et al. |
| 6,225,450 B1 | 5/2001 | Koster et al. |
| 6,235,478 B1 | 5/2001 | Koster |
| 6,238,871 B1 | 5/2001 | Koster |
| 6,258,538 B1 | 7/2001 | Koster et al. |
| 6,265,716 B1 | 7/2001 | Hunter et al. |
| 6,268,131 B1 | 7/2001 | Kang et al. |
| 6,268,144 B1 | 7/2001 | Koster |
| 6,269,846 B1 | 8/2001 | Overbeck et al. |
| 6,277,573 B1 | 8/2001 | Koster |
| 6,287,872 B1 | 9/2001 | Schurenberg et al. |
| 6,287,972 B1 | 9/2001 | Ziger et al. |
| 6,300,076 B1 | 10/2001 | Koster |
| 6,303,309 B1 | 10/2001 | Jurinke et al. |
| 6,309,891 B1 | 10/2001 | Shalon et al. |
| 6,322,970 B1 | 11/2001 | Little et al. |
| 6,342,396 B1 | 1/2002 | Perrin et al. |
| 6,355,487 B2 | 3/2002 | Kowallis |
| 6,376,044 B1 | 4/2002 | Jarrell et al. |
| 6,387,628 B1 | 5/2002 | Little et al. |
| 6,399,394 B1 | 6/2002 | Dahm et al. |
| 6,406,670 B1 | 6/2002 | Earley et al. |
| 6,419,881 B1 | 7/2002 | Weinberg et al. |
| 6,423,966 B2 | 7/2002 | Hillenkamp |
| 6,428,955 B1 | 8/2002 | Koster et al. |
| 6,485,913 B1 | 11/2002 | Becker et al. |
| 6,500,621 B2 | 12/2002 | Koster |
| 6,506,611 B2 | 1/2003 | Bienert et al. |
| 6,558,902 B1 | 5/2003 | Hillenkamp |
| 6,565,813 B1 | 5/2003 | Garyantes |
| 6,566,055 B1 | 5/2003 | Monforte et al. |
| 6,569,385 B1 | 5/2003 | Little et al. |
| 6,589,485 B2 | 7/2003 | Koster |
| 6,602,662 B1 | 8/2003 | Koster et al. |
| 6,605,257 B1 | 8/2003 | Nakazawa et al. |
| 6,610,253 B2 | 8/2003 | Kennedy et al. |
| 6,629,626 B1 | 10/2003 | Horsman et al. |
| 6,635,452 B1 | 10/2003 | Monforte et al. |
| 6,670,609 B2 | 12/2003 | Franzen et al. |
| 6,723,569 B1 | 4/2004 | Moore et al. |
| 6,730,517 B1 | 5/2004 | Koster et al. |
| 6,769,760 B1 * | 8/2004 | Kuo et al. ................. 347/44 |
| 6,812,455 B2 | 11/2004 | Hillenkamp |
| 6,835,352 B2 | 12/2004 | Ito et al. |
| 6,858,184 B2 | 2/2005 | Pelrine et al. |
| 6,861,214 B1 | 3/2005 | Rampal et al. |
| 7,144,554 B1 | 12/2006 | Gulla et al. |
| 7,256,046 B2 | 8/2007 | Nebuloni et al. |
| 7,267,800 B2 | 9/2007 | Takli et al. |
| 7,285,422 B1 | 10/2007 | Little et al. |
| 2001/0008615 A1 | 7/2001 | Little et al. |
| 2001/0049148 A1 | 12/2001 | Wolk et al. |
| 2001/0049149 A1 * | 12/2001 | Kennedy et al. ............. 436/180 |
| 2001/0055811 A1 | 12/2001 | Hillenkamp |
| 2002/0005478 A1 | 1/2002 | Hillenkamp et al. |
| 2002/0009394 A1 | 1/2002 | Koster et al. |
| 2002/0018999 A1 | 2/2002 | Henriksson et al. |
| 2002/0040130 A1 | 4/2002 | Braun |
| 2002/0041829 A1 | 4/2002 | Kowallis |
| 2002/0051971 A1 | 5/2002 | Stuelpnagel et al. |
| 2002/0076723 A1 | 6/2002 | Virtanen |
| 2002/0098115 A1 | 7/2002 | Fawcett et al. |
| 2002/0102725 A1 | 8/2002 | Zabarovsky et al. |
| 2002/0109085 A1 | 8/2002 | Hillenkamp et al. |
| 2002/0119578 A1 | 8/2002 | Zaffaroni et al. |
| 2002/0142483 A1 * | 10/2002 | Yao et al. ................. 436/180 |
| 2002/0155587 A1 | 10/2002 | Opalsky et al. |
| 2002/0159918 A1 | 10/2002 | Tseng et al. |
| 2003/0003465 A1 | 1/2003 | Little et al. |
| 2003/0017469 A1 | 1/2003 | Risinaer et al. |
| 2003/0022225 A1 | 1/2003 | Monforte et al. |
| 2003/0033091 A1 | 2/2003 | Opalsky et al. |
| 2003/0036057 A1 | 2/2003 | Braun et al. |
| 2003/0096426 A1 | 5/2003 | Little et al. |
| 2003/0111494 A1 | 6/2003 | Lin et al. |
| 2003/0113233 A1 | 6/2003 | Nanthakumar |
| 2003/0113745 A1 | 6/2003 | Monforte et al. |
| 2003/0124735 A1 | 7/2003 | Nanthakumar et al. |
| 2003/0129589 A1 | 7/2003 | Koster et al. |
| 2003/0148528 A1 | 8/2003 | Hillenkamp |
| 2003/0180148 A1 | 9/2003 | Weng |
| 2003/0180749 A1 | 9/2003 | Koster et al. |
| 2003/0190644 A1 | 10/2003 | Braun et al. |
| 2003/0207297 A1 | 11/2003 | Koster et al. |
| 2003/0215368 A1 | 11/2003 | Ito et al. |
| 2003/0220844 A1 | 11/2003 | Manellos et al. |
| 2003/0224418 A1 | 12/2003 | Braun et al. |
| 2003/0228594 A1 | 12/2003 | Koster et al. |
| 2004/0037748 A1 | 2/2004 | Hasan et al. |
| 2004/0072365 A1 | 4/2004 | Rose et al. |
| 2004/0126895 A1 | 7/2004 | Overbeck et al. |
| 2005/0053521 A1 | 3/2005 | Hirayama |
| 2005/0136534 A1 | 6/2005 | Austin et al. |
| 2006/0024841 A1 | 2/2006 | Yao et al. |
| 2008/0008874 A1 | 1/2008 | Little et al. |
| 2009/0130745 A1 * | 5/2009 | Williams et al. ........... 435/287.2 |
| 2009/0180931 A1 | 7/2009 | Silbert et al. |

FOREIGN PATENT DOCUMENTS

| | | |
|---|---|---|
| DE | 19618032 | 5/1996 |
| DE | 19628178 | 7/1996 |
| DE | 19731479 | 7/1997 |
| DE | 19754978 | 12/1997 |
| EP | 0339781 | 11/1989 |
| EP | 0396116 | 11/1990 |
| EP | 0500506 | 8/1992 |
| EP | 0543550 | 5/1993 |
| EP | 0268237 | 5/1998 |
| EP | 1164203 | 12/2001 |
| EP | 1262564 | 12/2002 |
| EP | 1271609 | 2/2003 |
| FR | 2597260 | 10/1987 |
| GB | 2017105 | 10/1979 |
| GB | 2233654 | 1/1991 |
| GB | 2312782 | 11/1997 |
| GB | 2332273 | 6/1999 |
| JP | 2215399 | 8/1990 |
| JP | A-8-233710 | 9/1996 |
| JP | 8290377 | 11/1996 |
| JP | 63230086 | 9/1998 |
| JP | 2001-033463 | 2/2001 |
| JP | 2001-296303 | 10/2001 |
| JP | 2007-147656 | 6/2007 |
| WO | WO 84/02579 | 7/1984 |
| WO | WO 88/05074 | 7/1988 |
| WO | WO 89/09406 | 10/1989 |
| WO | WO 89/10786 | 11/1989 |
| WO | WO 89/11270 | 11/1989 |
| WO | WO 89/12624 | 12/1989 |
| WO | WO 90/01564 | 2/1990 |
| WO | WO 92/07879 | 5/1992 |
| WO | WO 92/13629 | 8/1992 |
| WO | WO 93/09668 | 5/1993 |
| WO | WO 93/14108 | 7/1993 |
| WO | WO 94/03774 | 2/1994 |
| WO | WO 94/11529 | 5/1994 |
| WO | WO 94/11530 | 5/1994 |
| WO | WO 94/11735 | 5/1994 |

(56) References Cited

FOREIGN PATENT DOCUMENTS

| WO | WO 94/16101 | 7/1994 |
|---|---|---|
| WO | WO 94/21822 | 9/1994 |
| WO | WO 94/27719 | 12/1994 |
| WO | WO 95/04524 | 2/1995 |
| WO | WO 95/11755 | 5/1995 |
| WO | WO 95/13538 | 5/1995 |
| WO | WO 95/25116 | 9/1995 |
| WO | WO 95/25175 | 9/1995 |
| WO | WO 95/30773 | 11/1995 |
| WO | WO 95/35505 | 12/1995 |
| WO | WO 96/02836 | 2/1996 |
| WO | WO 96/19587 | 6/1996 |
| WO | WO 96/29431 | 9/1996 |
| WO | WO 96/32504 | 10/1996 |
| WO | WO 96/36731 | 11/1996 |
| WO | WO 97/08306 | 3/1997 |
| WO | WO 97/16699 | 5/1997 |
| WO | WO 97/33000 | 9/1997 |
| WO | WO 97/37041 | 10/1997 |
| WO | WO 97/42348 | 11/1997 |
| WO | WO 97/43617 | 11/1997 |
| WO | WO 98/03257 | 1/1998 |
| WO | WO 98/05965 | 2/1998 |
| WO | WO 98/12355 | 3/1998 |
| WO | WO 98/20019 | 5/1998 |
| WO | WO 98/20020 | 5/1998 |
| WO | WO 98/20166 | 5/1998 |
| WO | WO 98/22541 | 5/1998 |
| WO | WO 98/26179 | 6/1998 |
| WO | WO 98/34116 | 8/1998 |
| WO | WO 98/39481 | 9/1998 |
| WO | WO 99/12040 | 3/1999 |
| WO | WO 99/36760 | 7/1999 |
| WO | WO 99/57318 | 11/1999 |
| WO | WO 00/08474 | 2/2000 |
| WO | WO 00/25923 | 5/2000 |
| WO | WO 00/56446 | 9/2000 |
| WO | WO 00/60361 | 10/2000 |
| WO | WO 01/19518 | 3/2001 |
| WO | WO 02/055199 | 7/2002 |
| WO | WO 03/087410 | 10/2003 |

OTHER PUBLICATIONS

Sequenom Inc. MassARRAY System Promotional Folder 2007.
Ardrey, "Electrospray mass spectrometry", Spectroscopy Europe 4(4):10-18 (1992).
Arshady, Reza. Beaded polymer supports and gels: I. Manufacturing techniques, Journal of Chromatography, 586:181-197 (1991).
Arshady. Reza, Beaded polymer supports and gels: II. Physicochemical criteria and functionalization, Journal of Chromatography, 586:199-219 (1991).
Asseline et al. "New Solid-Phase for Automated Synthesis of Oligonucleotides Containing an Amino-Alkyl Linker at Their 3'-End," Tetrahedron Letters 31(1: 81-84 (1990).
Batista-Viera et al., A new method for reversible immobilization of thiol biomolecules based on solid-phase bound thiolsulfonate groups, App. Biochem and Biotech,31 :175-195 (1991).
Beattie et al., "Synthesis and use of oligonucleotide libraries," Chemical Abstracts 123: 1172 (1995).
Berkenkamp et al., "Infrared MALDI Mass Spectrometry of large Nucleic Acids" Science 281:260-262 (1998).
Bonftls, E. and N.T. Thuong. "Solid Phase Synthesis of 5', 3'Bifunctional Oligodeoxyribonucleotides Bearing a Masked Thiol Group at the 3'-End," Tetrahedron Letters 32(26): 3053-3056 (1991).
Braun et al., "Improved Analysis of Microsatellites Using Mass Spectrometry", Genomics 46:18-23 (1997).
Broach et al., "High Throughput Screening for Drug Discovery", Nature, 384(Suppl 7):14-16, 1996.
Brown et al., "A single-bead decode strategy using electrospray ionization mass spectrometry and a new photo labile linker: 3-amino-3-(2-nitrophenyl) propionic acid", Mol. Diversity 1:4-12 (1995).

Brummel et al. "Evaluation of mass spectrometric methods applicable to the direct analysis of non-peptide bead-bound combinatorial libraries", Anal. Chem., 1996, v. 68, pp. 237-242.
Burbaum et al., "New Technologies for High-Throughput Screening" Curro Opin Chem. Biol. 1:72-78, 1997.
Chrisey et al., Covalent attachment of synthetic DNA to self-assembled monolayer films, Nucl. Acids Res. 24:3031-3039 (1996).
Chrisey et at, Fabrication of patterned DNA surfaces, Nucl. Acids. Res. 24:3040-3047 (1996).
Church et al., "Multiplex DNA Sequencing", Science 240:185-188 (1988).
Crain, "Mass spectrometric techniques in nucleic acid research", Mass Spectr. Rev. 9:505-554 (1990).
Dai, Yugin, et al., Two-Layer Sample Preparation: A Method for MALDJ-MS Analysis of Complex Peptide and Protein Mixtures, Analytical. Chemistry, (1999), 1087-1097 71(5), American Chemical Society.
Day et al., "Immobilization of polynucleotides on magnetic particles," Biochem. J. 278: 735-740 (1991).
Debitsudo, A. "121 :83891 9 Preparation of nucleotide thioalkyl esters and monomolecular membrane" Chemical Abstracts 121: 1166 (1994).
Debitsudo, A. "121:109581 h Preparation of oligonucleotide monolayer," Chemical Abstracts 121: 1163:1163 (1994).
Debitsudo, A. "122:291447q Organic super-thin fim of oligonucleotide derivative and method for its preparation," Chemical Abstracts 122: 1100 (1995).
Ehring, H. et al., "Photochemical versus thermal mechanisms in matrix-assisted laser desorption/ionization probed by back side desorption", Rapid Comm. in Mass Spect. 10:821-824 (1996).
Emmett, M.R. and R.M. Caprioli. "Micro-Electrospray Mass Spectrometry: Ultra-High-Sensitivity Analysis of Peptides and Proteins," J. Am. Soc. Mass Spectrometry 5: 605-613 (1994).
Fast Evaporation, http://www.chemistry.wustl.edu/-msf/damon/samp_fast13 evap.html, pp. 1-2, Sample Preparation—Fast Evaporation. Downloaded Dec. 8, 2004.
Fernandes. P.R. "Letter from the Society President", J Biornol. Screening, 2(1): 1-9, 1997.
Frank and Koster, DNA chain length and the influence of base composition on electrophoretic mobility of oligodeoxyribonucleotides in polyacrylamide-gels, Nucl. Acids Res. 6:2069-2087 (1979).
Greene and Wuts, Protective Groups in Organic Synthesis, 2nd Edition, Wiley & Sons (1991).
Hayashi et al., Immobilization of thiol proteases onto porous poly-(vinyl alcohol) beads, Polymer Journal, 25:5,489-497(1993).
Hillenkamp and Ehring, Laser desorption mass spectrometry Part 1: Basic mechanisms and techniques, Mass Spectrometry in the Biological Sciences: A tutorial, pp. 165-179 (1992).
Hillenkamp et al., Matrix assisted UV-laser desorption lionization: A new approach to mass spectrometry of large biomolecules, Bio mass Spectr., Burlingame and McCloskey (eds.), pp. 49-61, Elsevier Science Publishers B.V., Amsterdam (1989).
Hofstadler et al. "Capillary Electrophoresis—Electrospray Ionization Fourier Transform Ion Cyclotron Resonance Mass Spectrometry for Direct Analysis of Cellular Proteins," Anal. Chem. 67: 1477-1480 (1995).
IUPACE-IUB Commission on Biochemical Nomenclature Symbols for Amino-Acid Derivatives and Peptides Recommendations (1971), Biochemistry, 1972 11(9):1726-1731.
Janzen et al., High Throughput Screening as a Discovery Tool in the Pharmaceutical Industry, Lab Robotics Automation (LRA), 8:261-265, 1996.
Jespersen et al. "Attomole Detection of Proteins by Matrix-assisted Laser Desorption/Ionization Mass Spectrometry with the Use of Picolitre Vials," Rapid Communications in Mass Spectrometry 8(8): 581-584 (1994).
Jett et al., "High-Speed DNA Sequencing: An Approach Based Upon fluorescence Detection of Single Molecules" J. Bio Strut & Dynam. 7(2):301-09 (1989).
Koster et al., "A strategy for rapid and efficient DNA sequencing by mass spectrometry", Nature Bio 14:1123-1128 (1996).

(56) References Cited

OTHER PUBLICATIONS

Koster et al., "Well-Defined Insoluble Primers for the Enzymatic Synthesis of Oligo and Polynucleotides", Hoppe-Seyler's Z. Physiol. Chern. 359:1579-1589 (1978).

Koster et at. N-acyl protecting groups for deoxynucleotides: A quantitative and comparative study, Tetrahedron 37:363-369 (1981).

Koster et at. Oligonucleotide synthesis and multiplex DNA sequencing using chemiluminescent detection, Nucl. Acids Res .• Symposium Series No. 24:318-321, (1991).

Kozal et al., "Extensive Polymorph isms Observed in HIV-1 Clade B Protease Gene Using High-Density Oligonucleotide Arrays," Nature Medicine, vol. 2, No. 7, pp. 753-759, (1996).

Landegren et al.. "DNA Diagnostics-Molecular techniques and automation", Science 242:229-237 (1988).

Lee, et al., Direct Measurement of the Forces Between Complementary Strands of DNA, Science, vol. 266, Nov. 4, 1994, 771-773.

Lennon, J. and Glish, G., "A transmission geometry probe for MALDI", Poster Abstract.

Li et al., "High-Resolution MALDI Fourier Transform Mass Spectrometry of Oligonucleotides", Anal Chem. 68(13):2090-2096 (1996).

Li et al. "Analysis of Single Mammalain Cell Lysates by Mass Spectrometry," J. Am. Chem. Soc. 118: 11662-11663 (1996).

Little et al., "Direct detection of synthetic and biologically generated double stranded DNA by MALDI-TOF MS", J. Mass Spec 17:1-8 (1997).

Little et al., "MALDI on a Chip: Analysis of Arrays of Low-Femtomole to Sub-femto-mole Quantities of Synthetic Oligonucleotides and DNA Diagnostic Products Dispensed by a Piezoelectric Pipet", Anal Chem. 69:4540-4546 (1997).

Little et al., "Mass spectrometry from miniaturized arrays for full comparative DNA analysis", Nature Med 3(12):1413-1416 (1997).

Lyttle et al., "Versatile Linker Chemistry for Synthesis of 3'-Modified DNA", Chem. Abst., 128(18):314 (1997).

M.C. Fitzgerald et al., "The promise of matrix-assisted laser desorption-ionization (MALDI) mass spectrometry," Annu. Rev. Biophys. Biomol. Struct. 24: 117-140 (1995).

Manoharan et al., "A 2'-O-thiol Tether in the Ribose Moiety of Nucleic Acids for Conjugation Chemistry", Gene, 149: 147-156 (1994).

Martin, "New technologies for large-genome sequencing", Genome 31:1073-1080 (1969).

McCray and Trentham, "Properties and uses of photo reactive caged compounds", Annu. Rev. Biophys. Biophys. Chern. 18:239-270 (1989).

Microdrop Gmbh. Nordersted. Germany, Autodrop system.

Moini et al., "A moving belt device to couple high-performance liquid chromatography and chemical reaction interface mass spectrometry", Bio Mass Spect 20:308-312 (1991).

Nelson et al., Time-of-flight mass spectrometry of nucleic acids by laser ablation and ionization from a frozen aqueous matrix, Rapid Communications in Mass Spectrometry 4:348-351 (1990).

Nelson et al., "Volatilization of high molecular weight DNA by pulsed laser ablation of frozen aqueous solutions", Science 246: 1585-1587 (1989).

Nicola, Anthony J., et al., Application of the Fast-evaporation Sample Preparation Method for improving Quantification of Angiotensin II by Matrix-assisted Laser Desorption/Ionization, Rapid Communications in Mass Spectrometry, (1995), 1164-1171, 9, John Wiley & Sons, Ltd.

Nordhoff et al., "Ion stability of nucleic acids in infrared matrix-assisted laser desorption/ionization mass spectrometry", Nuc Acids Res. 21(15):3347-3357 (1993).

Nordhoff et al., "Matrix-assisted laser desorption/ionization mass spectrometry of nucleic acids with wavelength in the ultraviolet and infrared", Rapid Comm. Mass Spectrom. 6:771-776 (1992).

O'Donnell et al., "Mass Array as an enabling technology for the industrial-scale analysis of DNA", Genetic Engineering News 17(21) (1997).

O'Donnell et al., "High-Density, Covalent Attachment of DNA to Silicon Wafers for Analysis by MALDI-TOF Mass Spectrometry", Analytical Chemistry 69(13):2438-2443 (1991).

O'Donnell-Maloney et al., "The development of micro fabricated arrays for DNA sequencing and analysis" TIBTECH 14:401-407 (1996).

O'Donnell-Maloney et al.. "Micro fabrication and array technologies for DNA sequencing and diagnostics", Genetic Analysis: Bimolecular Engineering 13:151-157 (1996).

On-Probe Decontamination for MALDI Samples, pp. 1-2, http://www.chemistry.msu.edu/faculty/bruening/onprobepurification.htm, Matrix. Downloaded Dec. 8, 2004.

Overberg et al., "Laser desorption mass spectrometry: part II performance and applications of matrix-assisted laser desorption/ionization of large biomolecules", Mass Spect in the Biolog Science: A Tutorial 181-197 (1992).

Pon et al., "Derivatization of Controlled Pore Glass Beads for Solid Phase Oligonucleotide Synthesis" Bio Technique 6{8}: 768-770 773-775 (1988).

Product brochure for LAMMA 500 Laser Microprobe Mass Analyzer, (Leybold-Heraeus GMBH), 3-15 (1983).

Rolfs et al., PCR: Clinical Diagnostics and Research. Springer-Verlag (1992).

Ruppert et al., "A rapid and high throughput method for plasmid isolations". Presented: Automation in Mapping and DNA Sequencing Conference. Aug. 31-Sep. 2, 1994.

Ruppert et al.. "Preparation of plasmid DNA as Sequencing Templates in a Microtiter Plate Format", Paper presented. Cold Spring Harbor Laboratory 1995.

Schober, et al., Accurate High-Speed Liquid Handling of Very Small Biological Samples, BiotechniQues, (1993) 15(2):324-329.

Schram. Karl H., "Mass spectrometry of nucleic acid components", Bio Appl of Mass Spect. 34:203-287 (1990).

Sequenom Advances the Industrial Genomics Revolution with the Launch of Its DNA MassArmy.TM. Automated Process Line, Press Release: Sep. 28, 1998. http://www.seQuenom.com|pressrelease.com.

Sequenom Reports DNA MassArray.TM. Technology More Sensitive Than Electrophoretic Methods in Detecting Gene Mutations: Automated DNA Analysis System Can Speed Up Microsatellite Analyses. Press Release: Dec. 15. 1997, http://www.sequenom.com|pressrelease.htm.

Sequenom Reports on Use of Its DNA MassArray.TM. Technology to Analyze Genes Associated with Alzheimer's Disease and Arteriosclerosis: Technology Has Applications in Drug Development. Press Release: Sep. 22, 1997, http://www.sequenom.com|pressrelease.htm.

Sequenom Signs Agreement With Bruker-Franzen Analytik to Develop Mass Spectrometer for DNA Massarray Analysis•. Press Release: Jan. 12, 1998. http://www.sequenom.com|pressrelease.htm.

Sequenom Uses DNA MassArray.TM. To Sequence Section of Human Cancer-Related p53 GeneM, Press Release: Mar. 27, 1998. http://www.sequenom.com|pressrelease.htm.

Shaler et al.. "Effect of Impurities on the matrix-Assisted Laser Desorption Mass Spectra of Single-Stranded Oligodeoxynucleotides". Anal. Chem. 68:576-579 (1996).

Siuzdak. Gary. "The emergence of mass spectrometry in biochemical research", PNAS USA 91:11290-11297 (1994).

Smith R. D., "New developments in biochemical mass spectrometry: Electrospray Ionization", Anal. Chem. 62:882-899(1990).

Smith. Cassandra L., "cDNA Fingerprinting of Breast Cancer Tumor Cells", Boston Univ., MA. 3-12, (1996).

Solouki et al. "Attomole Biomolecule Mass Analysis by Matrix-Assisted Laser Desorption/Ionization Fourier Transform Ion Cyclotron Resonance," Anal. Chem. 67:4139-4144 (1995).

Stults and Marsters, "Improved electrospray ionization of synthetic oligodeoxynucleotides", Rapid Comm. Mass Spectrom. 5:359-363 (1991).

Tang et al., "Matrix-assisted laser desorption/ionization mass spectrometry of immobilized duplex DNA probes", Nucleic Acids Research 23:3126-3131 (1995).

(56) References Cited

OTHER PUBLICATIONS

Tomer et al., "Coaxial Continuous Flow Fast Atom Bombardment for Higher-Molecular-Weight Peptides: Comparison with Static Fast Atom Bombardment and electrospray Ionization", Bio Mass Spect 20:783-788 (1991).

Trainor, "DNA Sequencing, Automation, and the Human Genome", Anal. Chern. 62:418-426 (1990).

Valaskovic et al. "Attomole Protein Characterization by Capillary Electrophoresis—Mass Spectrometry," Science 273: 1199-1202 (1996).

Valaskovic et al. "Attomole-Sensitivity Electrospray Source for Large-Molecule Mass Spectrometry," Anal. Chem. 67: 3802-3805 (1995).

Vertes A. et al., "Matrix-assisted laser desorption of peptides in transmission geometry", Rapid Comm. in Mass Spect. 4(7):263-266 (1990).

Vorm, et al, Improved Mass Accuracy in Matrix-Assisted Laser Desorption/Ionization Time-Of-Flight Mass Spectrometry of Peptides. Journal of the American Society for Mass Spectrometry, Nov. 1994, V5(N11): 955-958.

Vorm, Ole, et al., Improved Resolution and Very High Sensitivity in MALDI TOF of Matrix Surface Made by Fast Evaporation, Analytical Chemistry, (1994), 3281-3287, 66(19), American Chemical Society.

Wahl et al. "Use of small-diameter capillaries for increasing peptide and protein detection sensitivity in capillary electrophoresis-mass spectrometry," Electrophoresis 14: 448-457 (1993).

Wallace, "Ink-Jet Based Fluid Micro dispensing in Biochemical Applications," Microfab Technologies Inc., Laboratory Automation News, vol. 1, No. 5 pp. 6-9, (1996).

Weiler et al., "Hybridization Based DNA Screening on Peptide Nucleic Acid (PNA) Oligomer Arrays" Nucleic Acids Research, 25(14):2792-2799 1997.

Williams, Time of flight mass spectrometry of DNA laser-ablated from frozen aqueous solutions: applications to the Human Genome Project, Inti. J. Mass Spectrom. and Ion Processes 131 :335-344 {1994}.

Wilm et al. "Electrospray and Taylor-Cone theory, Dole's beam of macromolecules at last," International Journal of Mass Spectrometry and Ion Processes 136: 167-180 (1994).

Wu et al., Matrix-assisted Laser Desorption Time-ot-flight Mass Spectrometry of Oligonucleotides Using 3-Hydroxypicolinic Acid as an Ultraviolet-sensitive Matrix, Rapid Comm Mass Spec 7:142-146 (1993).

Wu et al., "Time-of-Flight Mass Spectrometry of Underivatized Single-Stranded DNA Oligomers by Matrix-Assisted Laser Desorption", Anal. Chem. 66:1637-1645 (1994).

Zhang et al. "Micro-preparation Procedure for High-sensitivity Matrix-assisted Laser Desorption Ionization Mass Spectrometry," Journal of Mass Spectrometry 30: 1768-1771 (1995).

Zhang et al. "Capillary electrophoresis combined with MALDI-MS spectrometry: continuous deposition on a matrix-precoated membrane target", J. Mass Spectr.,1996, v. 31, No. 9, pp. 1039-1046.

Zuckerman et al., Efficient methods for attachment of thiol specific probes to the 3'-ends of synthetic oligodeoxyribonucleotides, Nucleic Acids Research, 15:13, 5305-5321 (1987).

Office Action Mailed: Mar. 19, 1998 for U.S. Appl. No. 08/786,988, filed Jan. 23, 1009 now issued U.S. Patent No. 7,285,422 issued on Oct. 23, 2007.

Office Action Mailed:Dec. 15, 1998 for U.S. Appl. No. 08/786,988, filed Jan. 23, 1009 now issued U.S. Patent No. 7,285,422 issued on Oct. 23, 2007.

Office Action Mailed: Mar. 17, 1999 for U.S. Appl. No. 08/786,988, filed Jan. 23, 1009 now issued U.S. Patent No. 7,285,422 issued on Oct. 23, 2007.

Office Action Mailed: Dec. 7, 1999 for U.S. Appl. No. 08/786,988, filed Jan. 23, 1009 now issued U.S. Patent No. 7,285,422 issued on Oct. 23, 2007.

Office Action Mailed: Feb. 8, 2001 for U.S. Appl. No. 08/786,988, filed Jan. 23, 1009 now issued U.S. Patent No. 7,285,422 issued on Oct. 23, 2007.

Office Action Mailed: May 22, 2002 for U.S. Appl. No. 08/786,988, filed Jan. 23, 1009 now issued U.S. Patent No. 7,285,422 issued on Oct. 23, 2007.

Office Action Mailed: Mar. 18, 2003 for U.S. Appl. No. 08/786,988, filed Jan. 23, 1009 now issued U.S. Patent No. 7,285,422 issued on Oct. 23, 2007.

Office Action Mailed: Nov. 17, 2003 for U.S. Appl. No. 08/786,988, filed Jan. 23, 1009 now issued U.S. Patent No. 7,285,422 issued on Oct. 23, 2007.

Office Action Mailed: Jun. 9, 2004 for U.S. Appl. No. 08/786,988, filed Jan. 23, 1009 now issued U.S. Patent No. 7,285,422 issued on Oct. 23, 2007.

Office Action Mailed: Jan. 14, 2005 for U.S. Appl. No. 08/786,988, filed Jan. 23, 1009 now issued U.S. Patent No. 7,285,422 issued on Oct. 23, 2007.

Office Action Mailed: Nov. 30, 2005 for U.S. Appl. No. 08/786,988, filed Jan. 23, 1009 now issued U.S. Patent No. 7,285,422 issued on Oct. 23, 2007.

Office Action Mailed: Jul. 21, 2006 for U.S. Appl. No. 08/786,988, filed Jan. 23, 1009 now issued U.S. Patent No. 7,285,422 issued on Oct. 23, 2007.

Office Action Mailed: Jun. 13, 2007 for U.S. Appl. No. 08/786,988, filed Jan. 23, 1009 now issued U.S. Patent No. 7,285,422 issued on Oct. 23, 2007.

Office Action Mailed: Feb. 23, 2001 for U.S. Appl. No. 09/364,774, filed Jul. 30, 1999 and published as US 2003-0096426 on May 22, 2003, now issued U.S. Patent No. 7,232,688 issued on Jun. 19, 2007.

Office Action Mailed: Oct. 1, 2002 for U.S. Appl. No. 09/364,774, filed Jul. 30, 1999 and published as US 2003-0096426 on May 22, 2003, now issued U.S. Patent No. 7,232,688 issued on Jun. 19, 2007.

Office Action Mailed: Feb. 25, 2003 for U.S. Appl. No. 09/364,774, filed Jul. 30, 1999 and published as US 2003-0096426 on May 22, 2003, now issued U.S. Patent No. 7,232,688 issued on Jun. 19, 2007.

Office Action Mailed: Aug. 13, 2003 for U.S. Appl. No. 09/364,774, filed Jul. 30, 1999 and published as US 2003-0096426 on May 22, 2003, now issued U.S. Patent No. 7,232,688 issued on Jun. 19, 2007.

Office Action Mailed: Nov. 18, 2003 for U.S. Appl. No. 09/364,774, filed Jul. 30, 1999 and published as US 2003-0096426 on May 22, 2003, now issued U.S. Patent No. 7,232,688 issued on Jun. 19, 2007.

Office Action Mailed: Sep. 24, 2004 for U.S. Appl. No. 09/364,774, filed Jul. 30, 1999 and published as US 2003-0096426 on May 22, 2003, now issued U.S. Patent No. 7,232,688 issued on Jun. 19, 2007.

Office Action Mailed: Apr. 13, 2005 for U.S. Appl. No. 09/364,774, filed Jul. 30, 1999 and published as US 2003-0096426 on May 22, 2003, now issued U.S. Patent No. 7,232,688 issued on Jun. 19, 2007.

Office Action Mailed: Dec. 22, 2005 for U.S. Appl. No. 09/364,774, filed Jul. 30, 1999 and published as US 2003-0096426 on May 22, 2003, now issued U.S. Patent No. 7,232,688 issued on Jun. 19, 2007.

Office Action Mailed: Jul. 27, 2006 for U.S. Appl. No. 09/364,774, filed Jul. 30, 1999 and published as US 2003-0096426 on May 22, 2003, now issued U.S. Patent No. 7,232,688 issued on Jun. 19, 2007.

Office Action Mailed: Jan. 29, 2007 for U.S. Appl. No. 09/364,774, filed Jul. 30, 1999 and published as US 2003-0096426 on May 22, 2003, now issued U.S. Patent No. 7,232,688 issued on Jun. 19, 2007.

Office Action mailed: Oct. 10, 2013 for U.S. Appl. No. 12/123,378, filed May 19, 2008 and published as US 2008-024896 on Oct. 9, 2008.

Office Action mailed: Mar. 28, 2013 for U.S. Appl. No. 12/123,378, filed May 19, 2008 and published as US 2008-024896 on Oct. 9, 2008.

Office Action mailed: Oct. 6, 2009 for U.S. Appl. No. 12/123,378, filed May 19, 2008 and published as US 2008-024896 on Oct. 9, 2008.

Office Action mailed: Mar. 31, 2009 for U.S. Appl. No. 12/123,378, filed May 19, 2008 and published as US 2008-024896 on Oct. 9, 2008.

Office Action Mailed: Jan. 30, 2008 for U.S. Appl. No. 11/764,711, filed Jun. 18, 2001 and published as US 2008-0008874 on Jan. 10, 2008, now issued U.S. Patent No. 7,390,672 issued on Jun. 24, 2008.

(56) References Cited

OTHER PUBLICATIONS

Office Action Mailed: Apr. 2, 2008 for U.S. Appl. No. 11/764,711, filed Jun. 18, 2001 and published as US 2008-0008874 on Jan. 10, 2008, now issued U.S. Patent No. 7,390,672 issued on Jun. 24, 2008.
Office Action Mailed: May 11, 2004 for U.S. Appl. No. 10/037,356, filed Oct. 24, 2001, published as US 2002-0142483 on Oct. 3, 2002, now abandoned.
Office Action Mailed: Sep. 1, 2004 for U.S. Appl. No. 10/037,356, filed Oct. 24, 2001, published as US 2002-0142483 on Oct. 3, 2002, now abandoned.
Office Action Mailed: Apr. 4, 2005 for U.S. Appl. No. 10/037,356, filed Oct. 24, 2001, published as US 2002-0142483 on Oct. 3, 2002, now abandoned.
Office Action Mailed: Oct. 23, 2008 for U.S. Appl. No. 11/243,113, filed Oct. 4, 2005 published as US 2006-0024841 on Feb. 2, 2006.
Office Action Mailed: Jun. 29, 2009 for U.S. Appl. No. 11/243,113, filed Oct. 4, 2005 published as US 2006-0024841 on Feb. 2, 2006.
Office Action Mailed: Jan. 5, 2010 for U.S. Appl. No. 11/243,113, filed Oct. 4, 2005 published as US 2006-0024841 on Feb. 2, 2006.
Office Action Mailed: Jul. 8, 2010 for U.S. Appl. No. 11/243,113, filed Oct. 4, 2005 published as US 2006-0024841 on Feb. 2, 2006.
Office Action Mailed: Jan. 18, 2011 for U.S. Appl. No. 11/243,113, filed Oct. 4, 2005 published as US 2006-0024841 on Feb. 2, 2006.
Office Action Mailed: Aug. 19, 2011 for U.S. Appl. No. 11/243,113, filed Oct. 4, 2005 published as US 2006-0024841 on Feb. 2, 2006.
Office Action Mailed: Jan. 23, 2012 for U.S. Appl. No. 11/243,113, filed Oct. 4, 2005 published as US 2006-0024841 on Feb. 2, 2006.
Office Action Mailed: Jun. 26, 2012 for U.S. Appl. No. 11/243,113, filed Oct. 4, 2005 published as US 2006-0024841 on Feb. 2, 2006.
Office Action dated: Apr. 23, 2004 in U.S. Appl. No. 10/117,558, filed Apr. 3, 2002 and published as: 2002/0109085 on: Aug. 15, 2002 and issued as: U.S. Patent No. 6,812,455 on: Nov. 2, 2004.
Office Action dated: Jan. 14, 2004 in U.S. Appl. No. 10/117,558, filed Apr. 3, 2002 and published as: 2002/0109085 on: Aug. 15, 2002 and issued as: U.S. Patent No. 6,812,455 on: Nov. 2, 2004.
Office Action dated: Aug. 7, 2003 in U.S. Appl. No. 10/117,558, filed Apr. 3, 2002 and published as: 2002/0109085 on: Aug. 15, 2002 and issued as: U.S. Patent No. 6,812,455 on: Nov. 2, 2004.
Office Action Mailed: Sep. 12, 2011 for U.S. Appl. No. 12/211,796, filed Sep. 16, 2008 and published as: 2009/0180931 on Jul. 16, 2009.
Office Action Mailed: Apr. 26, 2012 for U.S. Appl. No. 12/211,796, filed Sep. 16, 2008 and published as: 2009/0180931 on Jul. 16, 2009.
International Search Report and Written Opinion dated: Apr. 13, 2009 in International Application No. PCT/US2008/076567 filed: Sep. 16, 2008 and published as: WO/2009/039122 on: Mar. 26, 2009.
International Preliminary Report on Patentability dated: Apr. 1, 2010 in International Application No. PCT/US2008/076567 filed: Sep. 16, 2008 and published as: WO/2009/039122 on: Mar. 26, 2009.
International Search Report and Written Opinion Report dated: Feb. 2, 2003 in International Application No. PCT/US2001/45123 filed Oct. 24, 2001 and published as: WO/2002/055199 on: Jul. 18, 2002.
International Preliminary Examination Report dated: Apr. 4, 2003 in International Application No. PCT/US2001/45123 filed Oct. 24, 2001 and published as: WO/2002/055199 on: Jul. 18, 2002.
Office Action dated Nov. 7, 2013 in U.S. Appl. No. 13/683,214, filed Nov. 21, 2012 and published as US 2013-0079247 on Mar. 28, 2013.
Office Action dated Apr. 18, 2014 in U.S. Appl. No. 12/123,378, filed May 19, 2008 and published as US 2008-0248968 on Oct. 9, 2008.
Office Action dated Jun. 19, 2014 in U.S. Appl. No. 13/683,214, filed Nov. 21, 2012 and published as US 2013-0079247 on Mar. 28, 2013.

\* cited by examiner

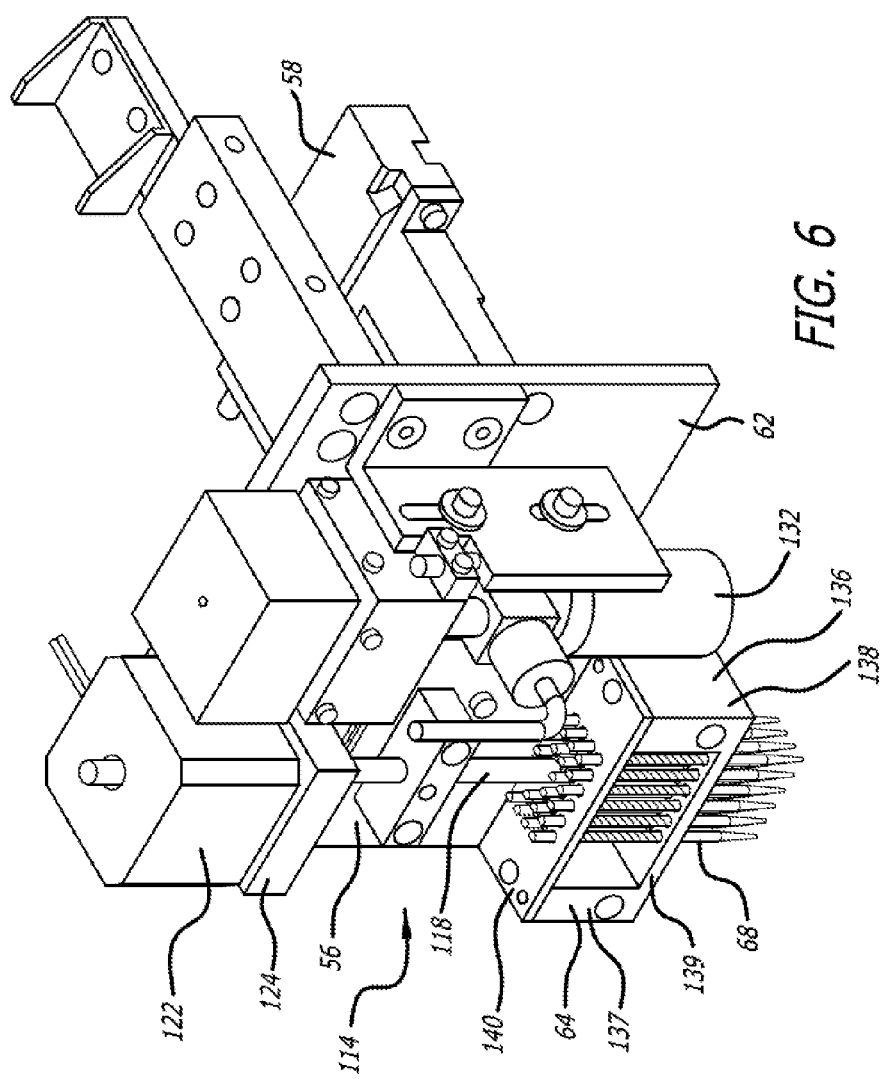

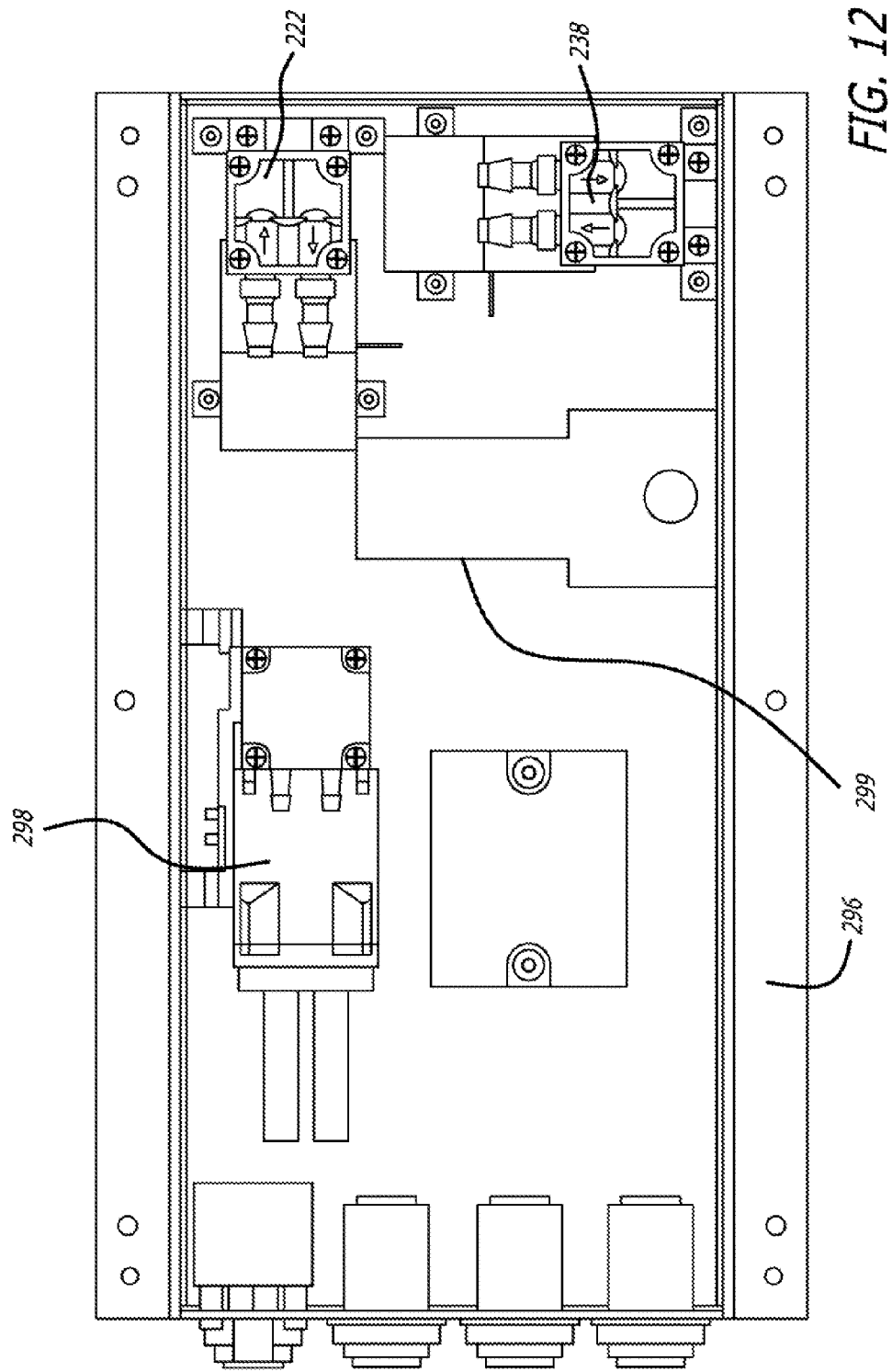

FIG. 28

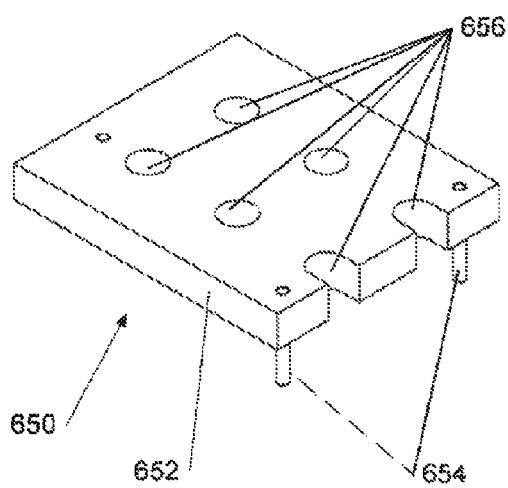
FIG. 41A
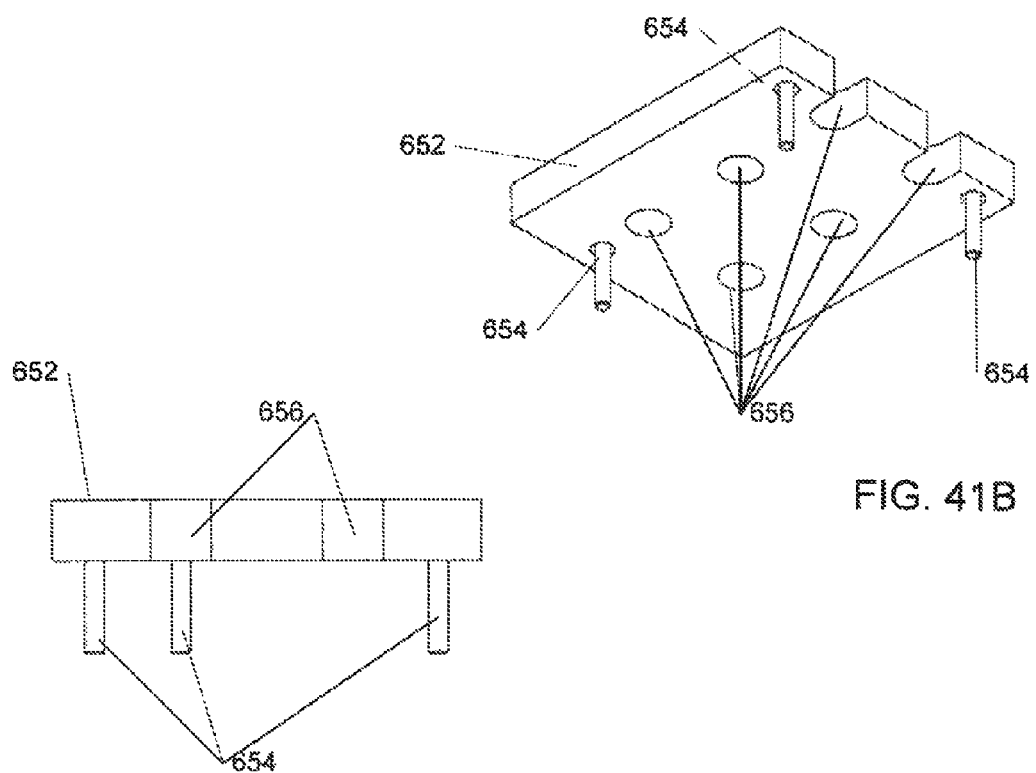
FIG. 41B
FIG. 41C

INTEGRATED ROBOTIC SAMPLE TRANSFER DEVICE

RELATED APPLICATIONS

This patent application is a continuation application of U.S. patent application Ser. No. 12/211,796, filed on Sep. 16, 2008, naming Rolf Silbert, Richard Capella, and Justin Cuzens as inventors, which claims the benefit of U.S. provisional application No. 60/972,879, filed on Sep. 17, 2007, naming Rolf Silbert, Richard Capella, and Justin Cuzens as inventors. The entire content of the foregoing patent applications is incorporated herein by reference, including all text, tables, and drawings.

FIELD OF THE INVENTION

Embodiments of the present invention generally relate to robotic sample transfer devices and methods which may be used for reliably and consistently transferring large numbers of small samples of material from one registered position to another registered position. Such transfers of material may be carried out by a single pin tool or an array of regularly spaced pin tools on a pin tool head assembly. Some embodiments include automated cleaning of the pin tools used to transfer the sample material between sample transfer steps.

BACKGROUND

In recent years, developments in the field of life sciences have proceeded at a very rapid pace. Universities, hospitals and newly formed companies have made groundbreaking scientific discoveries and advances that promise to reshape the fields of medicine, agriculture, and environmental science. However, the success of these efforts depends, in part, on the development of sophisticated laboratory tools that will automate and expedite the testing and analysis of biological samples. Only upon the development of such tools can the benefits of these recent scientific discoveries be fully achieved.

At the forefront of these efforts to develop better analytical tools is an effort to expedite the analysis of complex biochemical structures. This is particularly true for human genomic DNA, which is comprised of at least about one hundred thousand genes located on twenty four chromosomes. Each gene codes for a specific protein, which fulfills a specific biochemical function within a living cell. Changes in a DNA sequence are known as mutations and can result in proteins with altered or in some cases even lost biochemical activities; this in turn can cause a genetic disease. More than 3,000 genetic diseases are currently known. In addition, growing evidence indicates that certain DNA sequences may predispose an individual to any of a number of genetic diseases, such as diabetes, arteriosclerosis, obesity, certain autoimmune diseases and cancer. Accordingly, the analysis of DNA is a difficult but worthy pursuit that promises to yield information fundamental to the treatment of many debilitating and life threatening diseases.

Analysis of DNA is made particularly cumbersome due to size and the fact that genomic DNA includes both coding and non-coding sequences (e.g., exons and introns). As such, traditional techniques for analyzing chemical structures, such as the manual pipeting of source material to create samples for analysis, are of little value. To address the scale of the necessary analysis, scientists have developed parallel processing protocols for DNA diagnostics.

Robotic pin tool devices used for the accurate and efficient transfer of materials from sample wells to sample test sites have been used for the processing of materials for a great variety of applications. Such devices are frequently used for the processing of fluid DNA samples for mass spectrometry, including MALDI mass spectrometry, genotyping, quantitative gene expression including PCR methods, methylation analysis and SNP discovery. For such processes, a small amount of fluid is taken up by a pin tool from a pre-determined well of a microtiter plate and mapped and deposited to a pre-determined location on another surface, such as a mass spectrometry chip. The control software for the robotics of the robotic pin tool generally will track the transfer of samples from each well of the microtiter plate to the corresponding location on the chip such that a comprehensive mapping of samples is maintained. Once a set of samples have been transferred, the pins may undergo a washing process and may then be used to transfer another set of samples. Such tools and processes greatly enhance the efficiency and reliability of sample handling and processing where a large number of small volume samples need to be processed.

Current devices that perform these procedures are useful, but are generally large, heavy and expensive machines that require the use of large external fluid storage tanks, external computing devices, including desktop units with corresponding keyboard and monitor devices, external plumbing to facility utilities and the like. As a result, a standard pin tool sample transfer machine may take up a large amount of space within a laboratory in which it is being used. In addition, standard pin tool sample transfer devices may be inconvenient to operate and maintain. What has been needed is a robotic sample transfer machine that is small in size and weight relative to existing machines and less expensive than the currently available sample transfer devices. What has also been needed is a robotic sample transfer device that is user friendly, easy and reliable to operate and economical to maintain.

SUMMARY

Some embodiments of robotic sample transfer devices include a substantially horizontal work surface and a three axis robotic positioning assembly. The three axis robotic positioning assembly has a fixed mount portion secured in fixed relation with the work surface, a translatable carrier configured to be translatable in three different axes with respect to the fixed mount portion and working surface. The three axis robotic positioning assembly has a stepper motor and corresponding linear encoder assembly for at least one axis. A controller is in communication with the stepper motor of each of the three axes and linear encoder of the three axis robotic positioning assembly.

Some embodiments of a robotic sample transfer device include a housing, a substantially horizontal work surface disposed within the housing and a three axis robotic positioning assembly disposed within the housing having a fixed mount portion secured in fixed relation with the work surface and a translatable carrier member translatable in three different axes with respect to the fixed mount portion and work surface. The robotic sample transfer device also includes at least one pin tool coupled to the translatable carrier having a shaft and a sample reservoir in a distal end of the shaft. A plurality of functional elements may be disposed on the work surface having a nominal upper surface at substantially the same z-axis height. The robotic sample transfer assembly may also include a controller operatively coupled to the three axis robotic positioning assembly.

For some embodiments, the functional elements disposed on the work surface include a vacuum drying station, a fluid rinse station, a self-leveling ultrasonic cleaning well, a microtiter plate having an array or regularly space sample supply wells and a chip having an array of regularly spaced sample deposition sites. For some embodiments, the controller of the robotic sample transfer device includes at least one processor which is disposed within the housing at a level which is above the level of the work surface.

Some embodiments of an integrated robotic sample transfer device include a housing, a substantially horizontal work surface and a three axis robotic positioning assembly disposed within the housing. The three axis robotic positioning assembly may include a fixed mount portion, a translatable carrier which is translatable in three different axes with respect to the fixed mount portion, and a stepper motor for each axis. Some embodiments may include a linear encoder for at least one of the axes. A pin tool head assembly may be secured to the translatable carrier member and have an array of regularly spaced pin tools which have sample reservoirs disposed in the distal ends thereof and which are configured for axial displacement relative to a pin head body secured to the translatable carrier of the three axis robotic positioning assembly. The substantially horizontal work surface is disposed within the housing and is secured in fixed relation to the fixed mount portion of the three axis positioning assembly. The work surface may have a plurality of functional components disposed thereon which may include a fluid rinse station, a vacuum drying station including a plurality of regularly spaced vacuum drying ports corresponding to the regular spacing of the array of pin tools, a self-filling ultrasonic cleaning well and a microtiter plate mount block. The microtiter plate mount block is configured to releasably secure a pre-selected microtiter plate sample well thereto. A chip mount block may also be disposed on the work surface and have a nominal upper surface at substantially the same level as at least one or more of the functional components. A controller including a processor is disposed within the housing at a position which is above the level of the work surface. A rinse fluid supply tank is in fluid communication with the fluid rinse station and disposed within the housing. A waste water tank is in fluid communication with an overflow basin of the fluid rinse station and disposed within the housing. A vacuum source is in fluid communication with the vacuum drying station and an ultrasonic cleaning fluid supply reservoir is in fluid communication with the self-filling ultrasonic cleaning well.

Some embodiments of a method of registering a position of a pin tool head assembly of a robotic sample transfer device relative to sample deposition sites on a chip include providing a robotic sample transfer device having a work surface with a plurality of functional elements, at least two of which have a nominal upper surface at substantially the same level. For some embodiments, a nominal upper surface of all the functional elements may be at the same z-axis level. For some embodiments, the functional elements that require a substantially precise positional alignment of pin tools being used at the functional element may be at substantially the same z-axis level. The robotic sample transfer device may also have a three axis positioning system with a camera secured to a translatable carrier thereof and the pin tool head assembly secured to a translatable carrier thereof. The nominal upper surfaces of functional components disposed on work surface are imaged by the camera and the image data of the nominal upper surfaces of the functional elements processed by an image processor to determine the approximate position of the pin tool head assembly relative to the functional elements.

The approximate position data is then used to move the field of view of the camera to a first chip having an array of regularly spaced sample deposition sites and an array of regularly spaced fiducial marks disposed between the sample deposition sites. The fiducial marks on the first chip are imaged by the camera and the image data of fiducial marks on the first chip processed by an image processor. Feedback may then be obtained regarding a position of the pin tool head assembly from one or more linear encoders of three axes of a three axis robotic positioning system. Linear encoder feedback may then be compared with image processing feedback and look up table data to determine the precise position of the pin tools of the pin tool head assembly with respect to the sample deposition sites on the first chip. For some embodiments, the process may be repeated for two or more chips to determine the position of the pin tools of the pin tool head assembly with respect to sample deposition sites of the two or more chips.

Some embodiments of a method of dispensing calibration material onto a chip include providing a chip having a first array of regularly spaced sample deposition sites disposed on a substantially flat working surface thereof and at least one sample deposition site for receiving calibration material which is also disposed on the flat working surface of the chip and which is off pitch with respect to the regular spacing of the array of regularly spaced sample deposition sites of the chip. A robotic sample transfer device is provided which has a pin tool head assembly with an array of regularly spaced pin tools having distal ends which are substantially coplanar with each other in a relaxed state. The regular spacing of the pin tools corresponds to the regular spacing of the first array of sample deposition sites or an integer multiple thereof and is configured to align with the array of regularly spaced sample deposition sites of the chip or a subset thereof. Sample reservoirs of the pin tools of the array of regularly spaced pin tools of the robotic sample transfer device are loaded with calibration material. Calibration material is dispensed from the pin tools of the robotic sample transfer device to the at least one sample deposition site for receiving calibration material such that the pin tools which are not aligned with sample deposition sites for receiving calibration material are off pitch with respect to the first array of regularly spaced sample deposition sites of the chip and do not contact any of the regularly spaced sample deposition sites of the first array. For some embodiments, the chip may include a second array of regularly spaced sample deposition sites for receiving calibration material sample which are off pitch with respect to the first array of regularly spaced sample deposition sites. For such embodiments, calibration material from sample reservoirs of the pin tools of the robotic sample transfer device may be dispensed to the second array of sample deposition sites for receiving calibration material such that the pin tools which are not aligned with sample deposition sites for receiving calibration material of the second array are off pitch with respect to the first array of regularly spaced sample deposition sites of the chip and do not contact any of the regularly spaced sample deposition sites of the first array.

Some embodiments of a pin tool displacement block for selectively displacing at least one pin tool of a pin tool head assembly of a robotic sample transfer device include a block body portion having a top surface and a bottom surface which is substantially parallel to the top surface and a plurality of parallel slots formed into the block body portion. The pin tool displacement block also includes one or more relieved portions in the slots corresponding to the location of pins that are to remain in use when the pin tool displacement block is engaged with the pin tools of the pin tool head. For some embodiments, the parallel slots formed into the body portion have a width to allow passage and movement of a pin tool shafts but not a collar member secured to the pin tool shaft so as to displace the pin in a retracted position. Relieved portions in the slots are configured to allow passage and movement of the collar members so as not to displace the corresponding pin tools in a retracted position located in positions corresponding to pin tools which are to remain usable after deployment of the block in a pin tool head assembly. Some embodiments of the pin tool displacement block have a reversible configuration wherein when the block is oriented in a first direction a first set of pins or pin is active and oriented a second way a second set of pins or pin is active which is different from the first set.

Some embodiments of a method for selectively displacing at least one pin tool of a pin tool head assembly of a robotic sample transfer device, include providing a pin tool displacement block with a block body portion having a top surface and a bottom surface which is substantially parallel to the top surface, a plurality of parallel slots formed into the block body portion and one or more relieved portions in the slots corresponding to the location of pins that are to remain in use when the pin tool displacement block is engaged with the pin tools of the pin tool head. An array of pin tools of a pin tool head assembly are displaced by depressing the pin tools against a flat surface. The pin tool displacement block is deployed into the pin tool head assembly such that the parallel slots of the pin tool displacement block slide over rows of the array of pin tools of the pin tool head assembly and the pin tools are allowed to return to a relaxed state by retracting the pin tool head assembly from the flat surface.

Some embodiments of a method of dispensing calibration material onto a chip may include providing a chip having an array of regularly spaced sample deposition sites disposed on a substantially flat working surface thereof. The chip may also have at least one sample deposition site for receiving calibration material which is also disposed on the flat working surface of the chip. A robotic sample transfer device may be provided having a pin tool head assembly with an array of regularly spaced pin tools having distal ends which are substantially coplanar in a relaxed state and which have a regular spacing which is the same as the regular spacing of the first array of sample deposition sites or an integer multiple thereof. The pin tools of the pin tool head assembly may be configured to align with the array of regularly spaced sample deposition sites of the chip or a subset thereof. At least one of the pin tools of the pin tool head assembly may be axially displaced with a pin tool displacement block and a sample reservoir of at least one un-displaced pin tool of the robotic sample transfer device loaded with calibration material. Calibration material may be dispensed from the at least one un-displaced pin tool of the robotic sample transfer device to the at least one sample deposition site for receiving calibration material such that the pin tools which are displaced by the pin tool displacement block do not contact the chip.

These features of embodiments will become more apparent from the following detailed description when taken in conjunction with the accompanying exemplary drawings.

BRIEF DESCRIPTION OF THE DRAWINGS

FIG. 6 is a perspective view of the y-axis carrier and z-axis carrier of the three axis positioning system.

FIG. 12 is an elevation view of a pump housing with a rear cover of the housing not shown for clarity of illustration.

FIGS. 26-34 show screen image representations of a graphic user interface embodiment for communicating instructions and information to a controller of a robotic sample transfer device.

FIGS. 41A-41C illustrate an embodiment of a dry station plate assembly, six pin configuration.

DETAILED DESCRIPTION

Figure 1:
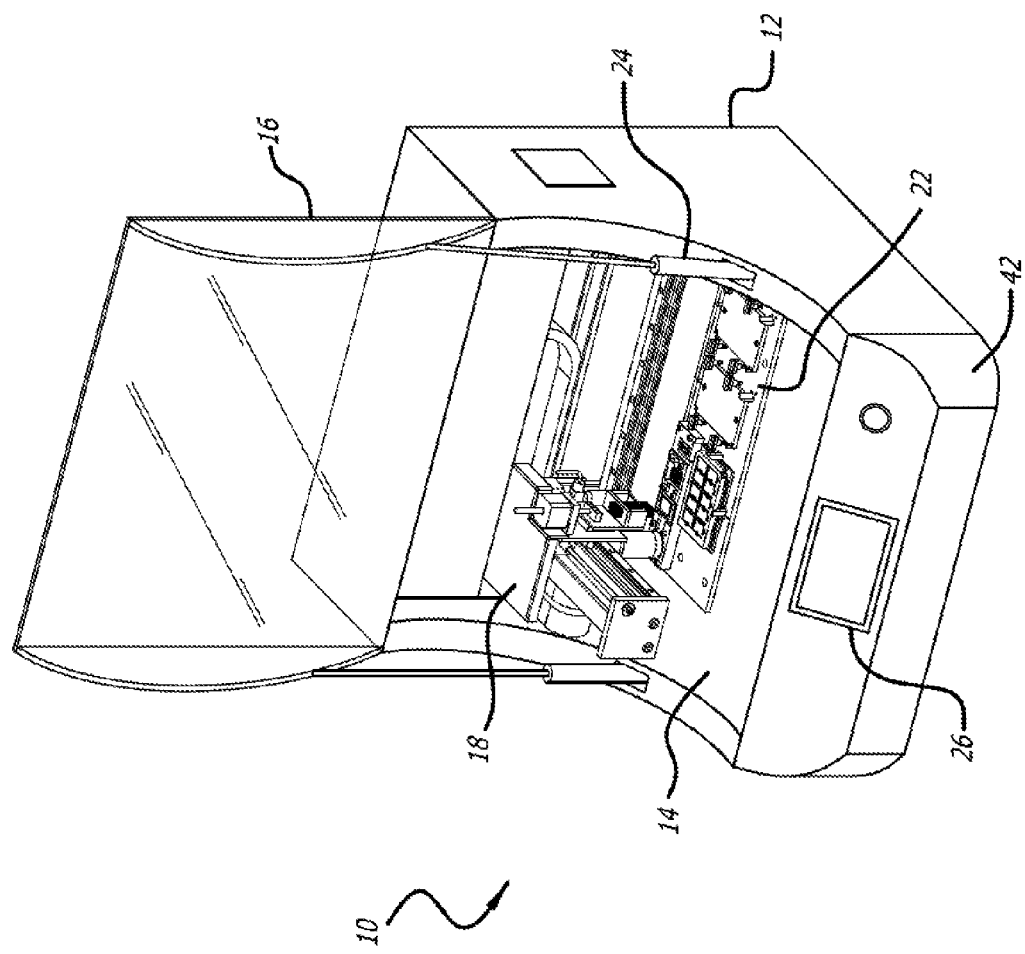
FIG. 1 is a perspective view of an embodiment of a robotic sample transfer device.

As discussed above, currently available robotic sample transfer devices are generally large, heavy and expensive machines that require the use of large external fluid storage tanks, external computing devices, including desktop units with corresponding keyboard and monitor devices, external plumbing to facility utilities and the like. As a result, a standard pin tool sample transfer machine may take up a large amount of space within a laboratory in which it is being used. In addition, standard pin tool sample transfer devices may be inconvenient and expensive to operate and maintain.

As such, a robotic sample transfer device that is relatively small in size and weight may be particularly useful. In addition, a robotic sample transfer device that is user friendly, easy and reliable to operate and can be simply maintained may also be particularly useful. Embodiments of robotic sample transfer devices described herein may be directed to integrated configurations that have a relatively small footprint with internal storage tanks, internal controllers and processors, internal plumbing all disposed within a housing that encloses a processing chamber. Such embodiments take up less laboratory space and are easy to use and maintain.

A graphic user interface may be disposed on an outer surface of the housing of some embodiments which allows a user to easily program and use the robotic sample transfer device while keeping the processing chamber closed. Embodiments of the graphic user interface may include touch screen displays allowing intuitive user input without the need for a computer keyboard or mouse, although such alternative interface tools may be supported in some embodiments via USB ports or the like. A substantially horizontal work surface may include a plurality of functional elements with two or more of the functional elements having nominal upper surfaces at approximately the same level which allows an imaging camera to easily image the functional elements of the work surface as well as providing a work surface at a consistent level for easy access and navigation. Such imaging of the functional elements may be used or otherwise processed in some embodiments to quickly determine the position of pin tools or pin tool head assemblies with respect to the functional elements with a high degree of precision.

Some robotic sample transfer device embodiments may be used for the accurate and efficient transfer of materials from one position to another position may be useful for the processing of samples and the like for a great variety of applications. Some embodiments may be used for the processing of fluid DNA samples for mass spectrometry, including MALDI mass spectrometry, genotyping, quantitative gene expression including PCR methods, methylation analysis and SNP discovery. Commonly owned U.S. Pat. No. 6,730,517, filed Oct. 5, 2000 by Koster et al., issued May 4, 2004, titled "Automated Process Line", describes automated modular analytical systems and methods of analysis of samples and is hereby incorporated by reference herein in its entirety. Some or all of the robotic sample transfer device embodiments discussed herein may be configured to perform some or all of the analytical processes discussed in U.S. Pat. No. 6,730,517. Embodiments of the robotic sample transfer device may be used to transfer samples that include liquids, solids, gels and the like, or any combination thereof.

Some robotic sample transfer device embodiments may include a substantially horizontal work surface that has a plurality of functional elements disposed on the work surface. The functional elements may be configured for the processing of small samples of material. A three axis robotic positioning assembly may have a fixed mount portion which is secured in a fixed relation with the work surface to provide mobility of tools and other devices over and in contact with the work surface and functional elements thereof. The three axis robotic positioning assembly may include one or more translatable carriers, at least one of which may be configured to be translatable in three different axes with respect to the fixed mount portion and working surface. For some embodiments, the three different axes of the translatable carrier may be substantially orthogonal to each other. Certain tools or other devices may be secured to the translatable carrier in order to provide high precision mobility of the tools and other devices with respect to the work surface and functional elements on the work surface. Some of the tools and devices that may be coupled to the translatable carrier include pin tools, pin tool head assemblies, cameras, bar code readers and the like. For some embodiments, upper nominal surface or surfaces of the functional elements may form the work surface.

While some translatable carrier embodiments may be movable and be positioned in three axes, the three axis robotic positioning assembly may include other translatable carrier embodiments, to which these same tools and devices may be coupled, that are moveable and may be positioned in only one axis or two axes. The three axis robotic positioning assembly may include a stepper motor for imparting motion and a corresponding linear encoder assembly for providing positional feedback or information for one or more of the three axes of the three axis robotic positioning assembly. As discussed above, one of the tools that may be moved in three axes above the work surface is a pin tool which may be coupled to the translatable carrier of the three axis robotic positioning assembly. The pin tool may be coupled to the translatable carrier such that the pin tool is substantially perpendicular to the work surface. For embodiments that include a pin tool head assembly, multiple pin tools of a pin tool head assembly which is coupled to a translatable carrier may also be oriented substantially perpendicular to the work surface.

A controller may be used in communication, such as electrical or optical communication, with the stepper motor and the linear encoder assembly of one or more of the axes of the three axis robotic positioning assembly in order to provide controllable movement to the one or more pin tools or other devices coupled to the translatable carrier or carriers. Such a controller may include one or more processors and data storage units in communication with the processor or processors. Some controller embodiments may also include one or more data input ports or terminals which allow a user to input data or other programming information in order to have the controller carry out desired instructions or processing protocols. A graphic user interface on a housing of the device may be in communication with such a terminals or ports of the controller. Some embodiments of the robotic sample transfer device may have the controller and associated components and electronics of the controller disposed above the vertical level of the work surface to avoid damage to these components from spillage of liquids on or around the work surface and associated functional components.

The controller may receive position data from the linear encoder assemblies as well as other sources and provide actuation signals and power to the stepper motors of the three axes in order to produce predetermined motion and positioning of the translatable carrier and tools coupled thereto with respect to the work surface and functional elements and with a high degree of precision. Position data generated by one of the linear encoder assemblies may include the position of a translatable carrier relative to a corresponding rail member upon which the translatable carrier moves. For such embodiments, an optical linear encoder strip may be disposed on the rail member and be positioned to be read by a linear encoder reader disposed on the corresponding translatable carrier.

Sometimes a housing may be disposed about the work surface, three axis robotic positioning assembly and controller as well as other components of robotic sample transfer device embodiments. Embodiments of the housing may include a skin material disposed on a frame structure. The skin material may be made of suitable polymers, composites, metals or the like in order to provide an enclosed controlled processing chamber and to protect the components of the robotic sample transfer device disposed therein. As discussed above, a graphic user interface may be disposed on or otherwise accessible from an exterior of the housing and be operatively coupled to the controller for providing user input, instructions, data or the like to the controller.

Some embodiments of a robotic sample transfer device may include a housing and a substantially horizontal work surface disposed within the housing. A three axis robotic positioning assembly may also be disposed within the housing for such embodiments and have a fixed mount portion secured in fixed relation with the work surface. The three axis robotic positioning assembly may include one or more translatable carrier members, including a translatable carrier member that is translatable in three different axes with respect to the fixed mount portion and work surface. At least one pin tool is coupled to the translatable carrier. The pin tool has a shaft and a sample reservoir in a distal end of the shaft. A variety of suitable reservoir embodiments may be used which may be configured to draw and store small volume liquid samples, generally in the nanoliter range of volume, into the reservoir by capillary action or other suitable mechanisms.

A plurality of functional elements may be disposed on the work surface with each functional element having a nominal upper surface. For some embodiments, an upper nominal surface or surfaces of the functional elements may form the work surface. For some embodiments, two or more of the nominal upper surfaces the functional elements may be disposed at substantially the same z-axis level or height. Such a configuration may be useful in order to facilitate imaging of the functional elements and positioning of the pin tool with respect to the nominal upper surface of each functional element. This may be particularly true in embodiments wherein an imaging camera is disposed on one or more of the translatable carriers of the robotic positioning assembly and is used for imaging the functional elements disposed on the work surface.

For such embodiments, it may be useful to have the imaging camera disposed on a translatable carrier embodiment that is translatable only in the X-Y plane, substantially parallel to the work surface. For such a camera with a fixed Z-axis position, the distance between the camera lens and the work surface or upper nominal surfaces of functional elements disposed on the work surface may be substantially fixed. Thus, camera embodiments having a fixed focal length and narrow range of focus may be positioned on the translatable carrier at the appropriate focal distance from the work surface for consistent focused imaging of the upper nominal surfaces of the functional elements. In this way, the upper nominal surfaces of the functional elements disposed at substantially the same z-axis level will remain in focus and be clearly imaged as the translatable carrier moves about over the work surface. The pin tool or other devices coupled to a translatable carrier which may be positioned in three axes may be moved independently of the camera in the Z-axis direction.

For some embodiments, the functional elements disposed on the work surface may include a vacuum drying station, a fluid rinse station, a self-leveling gravity fed ultrasonic cleaning well, a microtiter plate having an array or regularly space sample supply wells and a chip having an array of regularly spaced sample deposition sites. A controller may be operatively coupled to the three axis robotic positioning assembly as well as any of the functional elements on the work surface or components thereof. Such a controller may include one or more processors and data storage units in communication with the processor or processors which are disposed within the housing at a level which is above the level of the work surface.

For some embodiments, the pin tool which is coupled to the translatable carrier may be part of a pin tool head assembly having an array of regularly spaced pin tools which is secured or otherwise coupled to the translatable carrier. For some embodiments, the vacuum drying station may include a plurality of regularly spaced vacuum drying ports corresponding to the spacing of the pin tools of the pin tool head assembly. For some embodiments, the fluid rinse station may include individual rinse tubes corresponding to each of the pin tools of the array of regularly spaced pin tools of the pin tool head assembly.

For some embodiments, an ultrasonic cleaning fluid reservoir may be disposed in fluid communication with the ultrasonic cleaning well. The ultrasonic cleaning fluid reservoir may have an enclosed and fluid tight interior volume in fluid communication with a supply port configured to couple in fluid communication to an inlet port of the ultrasonic cleaning well. For some embodiments of such a configuration, the supply port of the ultrasonic cleaning fluid reservoir may be open to fluid flow when coupled into fluid communication with the inlet port of the ultrasonic cleaning well and be substantially sealed when the removed from the inlet port of the ultrasonic cleaning well. Some particular embodiments may include a ball valve which is configured to seal the supply port when the fluid reservoir is removed from the inlet port of the ultrasonic cleaning well.

Some embodiments of an integrated robotic sample transfer device may include a housing and a three axis robotic positioning assembly disposed within the housing having a fixed mount portion and a translatable carrier which is translatable in three axes with respect to the fixed mount portion and a substantially horizontal work surface. A stepper motor and corresponding linear encoder assembly may be included for one or more of the axes of the three axis robotic positioning assembly. Each stepper motor may be configured to provide motion in the direction of each respective axis and each linear encoder assembly may be used to provide position data in the direction of each respective axis. A pin tool head assembly may be secured to the translatable carrier member which has an array of regularly spaced pin tools with sample reservoirs disposed in the distal ends thereof. The pin tools may be configured for axial displacement relative to a pin head body which is secured to the translatable carrier of the three axis robotic positioning assembly. Some embodiments of the robotic sample transfer device may also include a door on the housing which is configured to cover an opening to a processing chamber disposed within the housing.

The substantially horizontal work surface may be disposed within the housing and secured in fixed relation to the fixed mount portion of the three axis robotic positioning assembly. The work surface may have one or more functional elements which may include a fluid rinse station, a vacuum drying station including a plurality of regularly spaced vacuum drying ports corresponding to the regular spacing of the array of pin tools, a self-leveling ultrasonic cleaning well and a microtiter plate mount block configured to releasably secure a sample well disposed thereon. For some embodiments, the upper nominal surfaces of two or more of the functional elements may form the work surface. For some of these embodiments, a nominal upper surface of the fluid rinse station, nominal upper surface of the vacuum drying station, nominal upper surface of the ultrasonic cleaning well, nominal upper surface of a chip disposed in the chip mount block and microtiter plate/sample well mounted in the sample well mount blocks are all disposed at substantially the same z-axis level. For some embodiments of the robotic sample transfer device, the entire dry weight of the device is less than about 150 pounds. For some embodiments, functional elements such as the ultrasonic cleaning well that do not require precise alignment in the x-y plane may be disposed at a z-axis level that differs from the z-axis level of the remaining functional elements or subset of functional elements having an upper nominal surface disposed at substantially the same z-axis level.

A controller may be disposed within the housing. Such a controller may include one or more processors and data storage units in addition to an assembly of other electronics and logic circuits in communication with the processor or processors which may be disposed within the housing at a level which is above the level of the work surface. The controller, electronics associated with the controller as well as other components of the robotic sample transfer device may be powered by a universal power supply in communication with the controller that produces a constant or substantially constant output voltage with varied input voltages. Such a universal power supply may allow the robotic sample transfer device to operate in a variety of countries with little or no modification.

Embodiments of the robotic sample transfer device may include a humidity sensor disposed within the processing chamber of the device in communication with the controller which is configured to sense the humidity within the processing chamber. For some of these embodiments, a closed loop feedback of sensed humidity levels within the processing chamber may be used in conjunction with a humidity control device for maintaining a substantially constant humidity within the processing chamber.

Embodiments of the robotic sample transfer device may include a temperature sensor disposed within the processing chamber of the sample transfer device in communication with the controller which is configured to sense the temperature within the processing chamber. For some of these embodiments, a closed loop feedback of sensed temperature levels within the processing chamber may be used in conjunction with a temperature control device for maintaining a substantially constant temperature within the processing chamber.

A graphic user interface may be disposed on an outer surface of the housing or in another convenient location and in communication with the controller. Some embodiments of the robotic sample transfer device may include an imaging camera which may be coupled to an image processing controller, a bar code reader head and bar code reader processor in communication with the bar code reading head and controller.

The fluid rinse station may include an array of regularly spaced individual rinse tubes having a regular spacing corresponding to the regular spacing of the pin tools of the pin tool head assembly. A rinse fluid supply tank may be disposed within the housing and in fluid communication with the fluid rinse station. Some embodiments of the sample transfer device may include a rinse fluid supply pump disposed within the housing, in fluid communication with the rinse fluid supply tank and fluid rinse station and configured to pump rinse fluid from the rinse fluid supply tank to the fluid rinse station. Some embodiments of the sample transfer device include a rinse fluid supply tank fluid level indicator. Such an indicator may be used to provide users with information with regard to the fluid level within the rinse fluid supply tank so the tank may be refilled prior to running out of rinse fluid.

A waste fluid tank may be disposed within the housing in fluid communication with an overflow basin of the fluid rinse station. Some embodiments of the sample transfer device may include a waste fluid tank fluid level indicator. Such an indicator may be used to provide users with information with regard to the waste fluid level within the waste fluid supply tank so the tank may be emptied prior to overflowing with waste fluid.

An ultrasonic cleaning fluid reservoir may be disposed within the housing in fluid communication with the self-leveling ultrasonic cleaning well. For some embodiments, the ultrasonic cleaning fluid reservoir includes a gravity feed reservoir having a supply port configured to couple into fluid communication with an inlet port of the ultrasonic cleaning well. The supply port may be configured to allow fluid flow when coupled to the inlet port of the ultrasonic cleaning well and be substantially sealed when the removed from the inlet port of the ultrasonic cleaning well.

A vacuum source may be disposed within the housing in fluid communication with the vacuum drying station. Some embodiments of the sample transfer device may also include a vacuum drying supply tank in fluid communication with the vacuum drying ports of the vacuum drying station. The vacuum drying supply tank may be a gas tight pressure vessel having an interior volume that may be partially emptied of air so as to provide a large volume of low pressure which can be used to draw air through the vacuum tubes of the vacuum drying station. Some of these embodiments may include a vacuum pump in fluid communication with the vacuum drying supply tank.

FIGS. 1-14 illustrate an embodiment of an integrated robotic sample transfer device 10 that may have features, dimensions and materials which are similar to or the same as the features, dimensions and materials of the robotic sample transfer device embodiments discussed above. The integrated robotic sample transfer device 10 may be used for reliably transferring large numbers of samples from one position on a work surface of the device to second position on the work surface of the device. The integrated robotic sample transfer device embodiment 10 shown includes a compact and user friendly configuration in that it does not require any external tanks or other major peripheral equipment in order to operate. The ultrasonic wash station, rinse station and vacuum drying station are all supplied by tanks that are disposed within the housing of the transfer device. In addition, any waste fluid generated by these stations drains to a waste fluid tank also disposed within the housing. Although the wash fluid and waste tanks include coupling ports to allow a user to connect the tanks to larger external tanks if desired, having these primary wash fluid supply and waste tanks disposed within the housing allows a user having minimum work space to efficiently and effectively use the sample transfer device.

The transfer device 10 includes a housing 12 having an outer sheathing that provides an enclosed processing chamber 14 that may be accessed by a hinged lid or door 16. The door may include a window with transparent sheathing material to allow a user to view the processes taking place within the processing chamber 14 while keeping the processing chamber enclosed and substantially isolated from the outside environment. The transparent sheathing of the window of the door 16 may include materials such as acrylic, PVC, polycarbonate and the like and have a thickness of about 0.1 inches to about 0.4 inches, for some embodiments. Such a configuration may allow the transparent material of the door 16 to be somewhat flexible and take on a curved shape or configuration. A safety interlock device (not shown) may include an interlock switch that is coupled between the door 16 and the remainder of the housing 12. The interlock device may be configured to detect when the door 16 is open or closed in order to prevent operation of the device 10, and particularly a robotic positioning system 18 of the device, while the door 16 is open. The sheathing or skin of the housing 12 may be formed from multiple panels of thin materials such as polymers, composites, metals, such as aluminum, and the like and may be secured to a frame structure of the housing 12. For some embodiments, the side panels of the housing 12 may be removable in order to provide greater access to the processing chamber 14 during the loading and unloading of samples or devices from within the processing chamber 14. An air port (not shown) may also be disposed on one or more of the panels, such as the side panels, of the housing 12 in order to provide an access port into the interior of the housing 12 and processing chamber 14. Such an air port may be used to force conditioned air into the processing chamber in order to control the temperature and humidity within the processing chamber 14.

The processing chamber 14 may be sized adequately to house the three axis robotic positioning system, work surface 22 and functional elements of the work surface 22. In addition, it may be desirable to have access by a user to some or all of these components in order to facilitate loading and unloading of samples, microtiter plates, chips, cleaning fluids and the like. The outer shape of the housing 12 is generally rectangular, with a sloping front surface formed by the door 16 that is hinged across the top edge of the door 16 which is configured to swing up and down. One or more pressurized gas damping pistons 24 may pivotally secured between the door 16 and a portion of the housing 12 beneath the door. The damping pistons 24 may be configured to offset the weight of the door 16 and provide damping of movement between the door 16 and the remainder of the housing 12 to prevent rapid movement of the door 16 and keep the door 16 open until manually closed by a user. Some embodiments of the housing 12 may have a height of about 12 inches to about 30 inches, more specifically, about 20 inches to about 26 inches, a width of about 20 inches to about 40 inches, more specifically, about 25 inches to about 30 inches, and a depth of about 12 inches to about 30 inches, more specifically, about 20 inches to about 26 inches.

Figure 2:
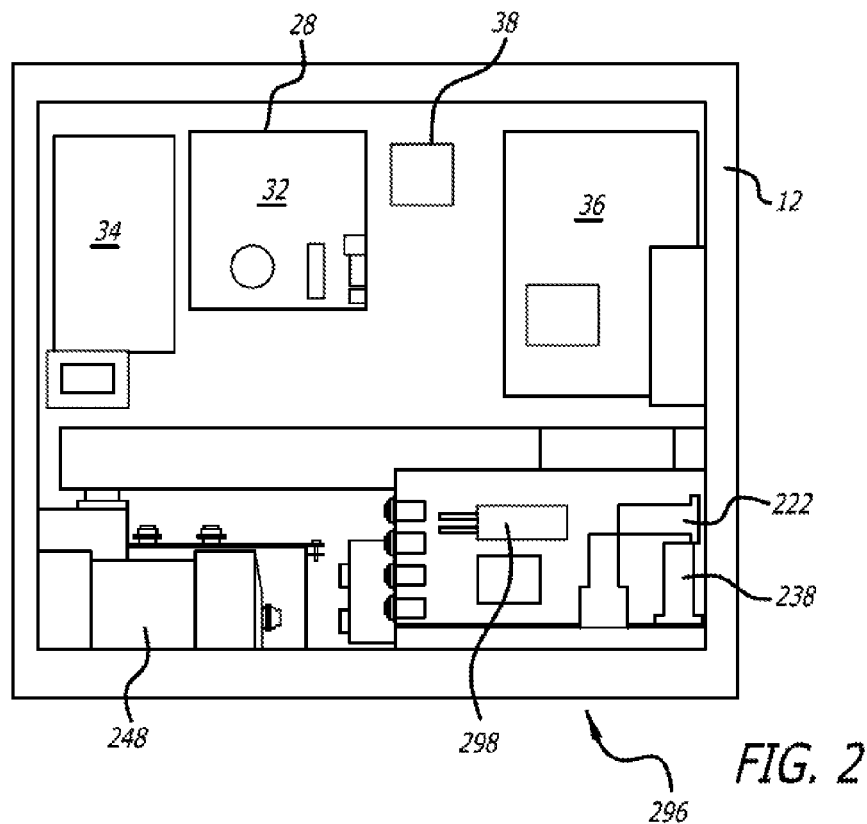
FIG. 2 is a rear elevation view with a rear panel of the housing not shown.

A graphic user interface 26 that includes a touch screen user interface is disposed on an outside surface of the housing 12. The touch screen user interface 26 may be a graphic screen coupled to a controller 28 which is shown in FIG. 2. The touch screen user interface 26 allows a user to turn on, program, turn off and generally interact with the controller 28 and other features of the device through a menu driven interface that is displayed on the touch screen. The controller 28 may be used or programmed generally to control the use, motion or both of the active components of the sample transfer device 10. In particular, the controller may be used or otherwise programmed to control the use of the functional elements and supporting element or components of the functional elements of the work surface 22. For example, the controller 28 may be used or otherwise programmed to control the movement of fluids, such as rinse water supply and waste, pressurized gases, vacuum sources, such as drying vacuum sources, and the administration of cleaning energy, such as ultrasonic cleaning energy for cleaning the pin tools of a pin tool head assembly and the like. The controller 28 may be used to control the movement of the translatable carriers of the three axis robotic positioning system 18 and the use and control of imaging devices secured to or otherwise associated with the translatable carriers, such as imaging cameras, bar code readers and the like. FIG. 2 is a rear elevation view of the sample transfer device embodiment 10 with a rear panel of the housing 12 not shown for purposes of illustration. With the rear panel of the housing removed, the controller 28 and some of the associated electronics thereof are visible.

The controller 28 may include a processor 32, such as a computer processor, a memory storage unit and suitable accompanying circuitry such as logic circuits and the like. Some embodiments include a universal power supply 34 coupled to the controller 28 and other electrical components of the sample transfer device that is configured to supply a substantially constant operating voltage to the controller 28 and other electrical components of the device for a variety of input voltages. Such a universal power supply 34 allows embodiments of the robotic sample transfer device 10 to be used with a variety of input power supply voltages without the need for modification. A customized PCB board 36 that includes signal routing switches, motor controllers, an amplifier for ultrasonic energy generation, as well as other components is mounted adjacent the processor 32. A cooling fan 38 is disposed between the PCB board 36 and processor 32 for cooling the portion of the housing 12 that houses the controller 28.

Figure 3:
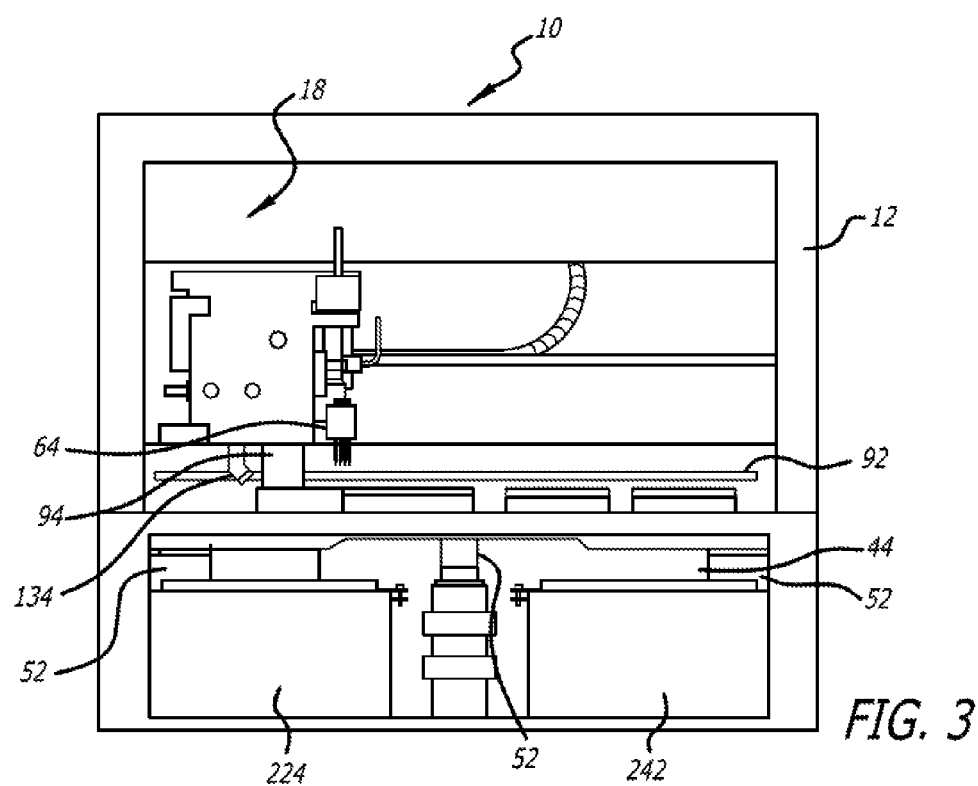
FIG. 3 is a front elevation view of the robotic sample transfer device of FIG. 1 with the processing chamber cover and tank chamber front cover not shown.

The touch screen feature 26 allows a user to interact and make menu selections directly on the touch screen 26. For the embodiment shown, the touch screen user interface 26 is disposed on a hinged cover or door that is disposed over the front of a lower storage tank chamber 44 which is shown in FIG. 3. The lower storage tank chamber 44 is a volume disposed within the housing below a work surface 22 of the sample transfer device 10. FIG. 3 shows a front elevation view of the sample transfer device 10 with the hinged cover 42 of the lower storage tank chamber 44 removed for purposes of illustration.

Figure 4:
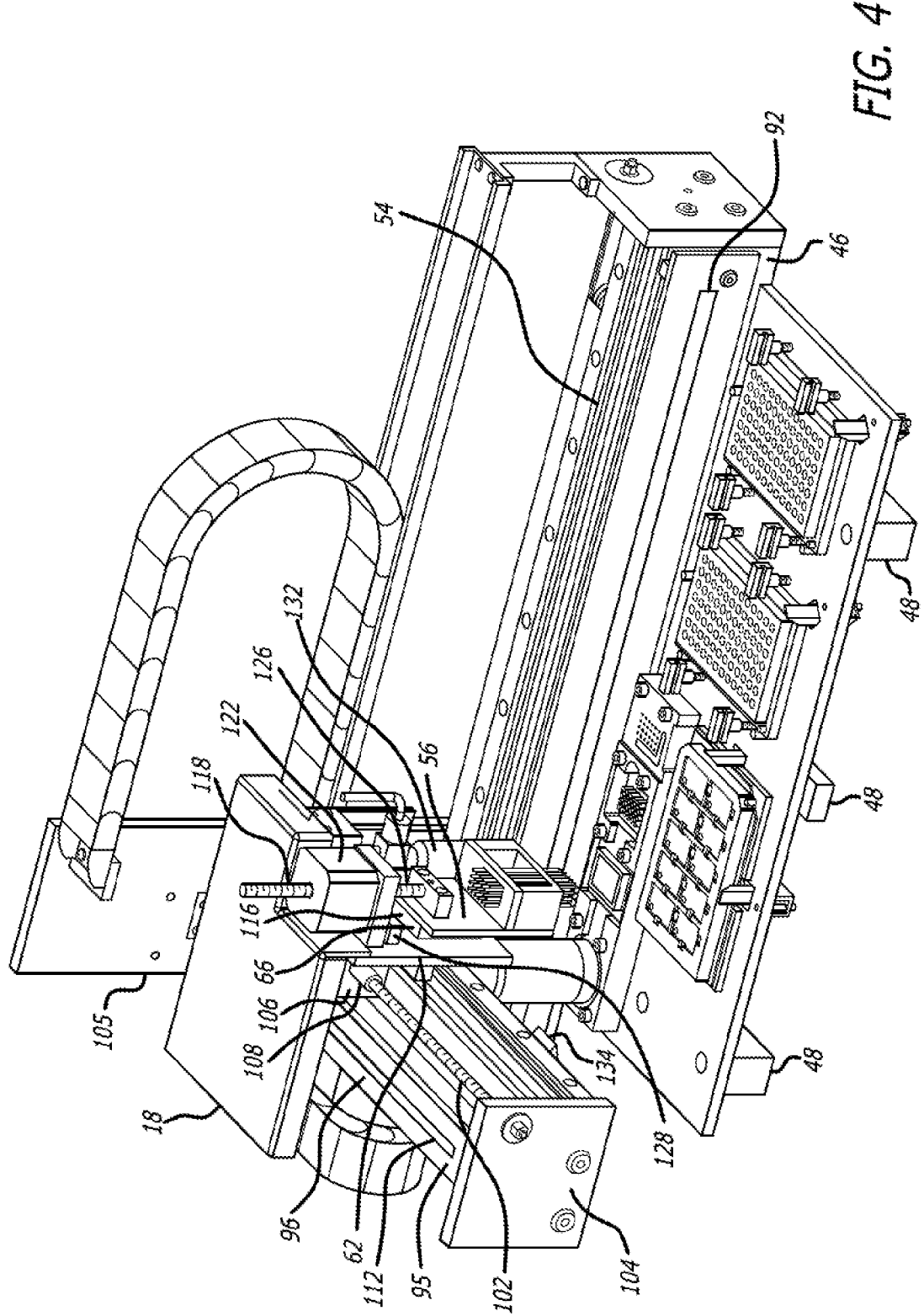
FIG. 4 is a perspective view of a three axis positioning system and work surface of the robotic sample transfer device of FIG. 1.

FIG. 4 illustrates an enlarged perspective view of some of the active processing components disposed within the processing chamber 14 of the sample transfer device embodiment 10. These active processing components are shown in an isolated view without the housing or other components for clarity. Generally, the work surface 22 and functional elements disposed on the work surface 22 provide locations to secure samples and other materials in a first registered position so that they can be moved or moved in part to a second registered position, for example, moving a portion of a sample fluid from a known well of a microtiter plate to a sample deposition site of a spectrometry chip with a pin tool. The three axis robotic positioning system 18 provides the system for generating precise motion relative to the registered positions of the work surface 22, such as by providing precise known motion and positioning of a pin tool relative to the work surface 22 and functional elements thereof. The work surface 22 and functional elements may also provide the necessary tools to clean the pin tool or other transfer devices such that they may be used for many consecutive transfer cycles.

Figure 5:
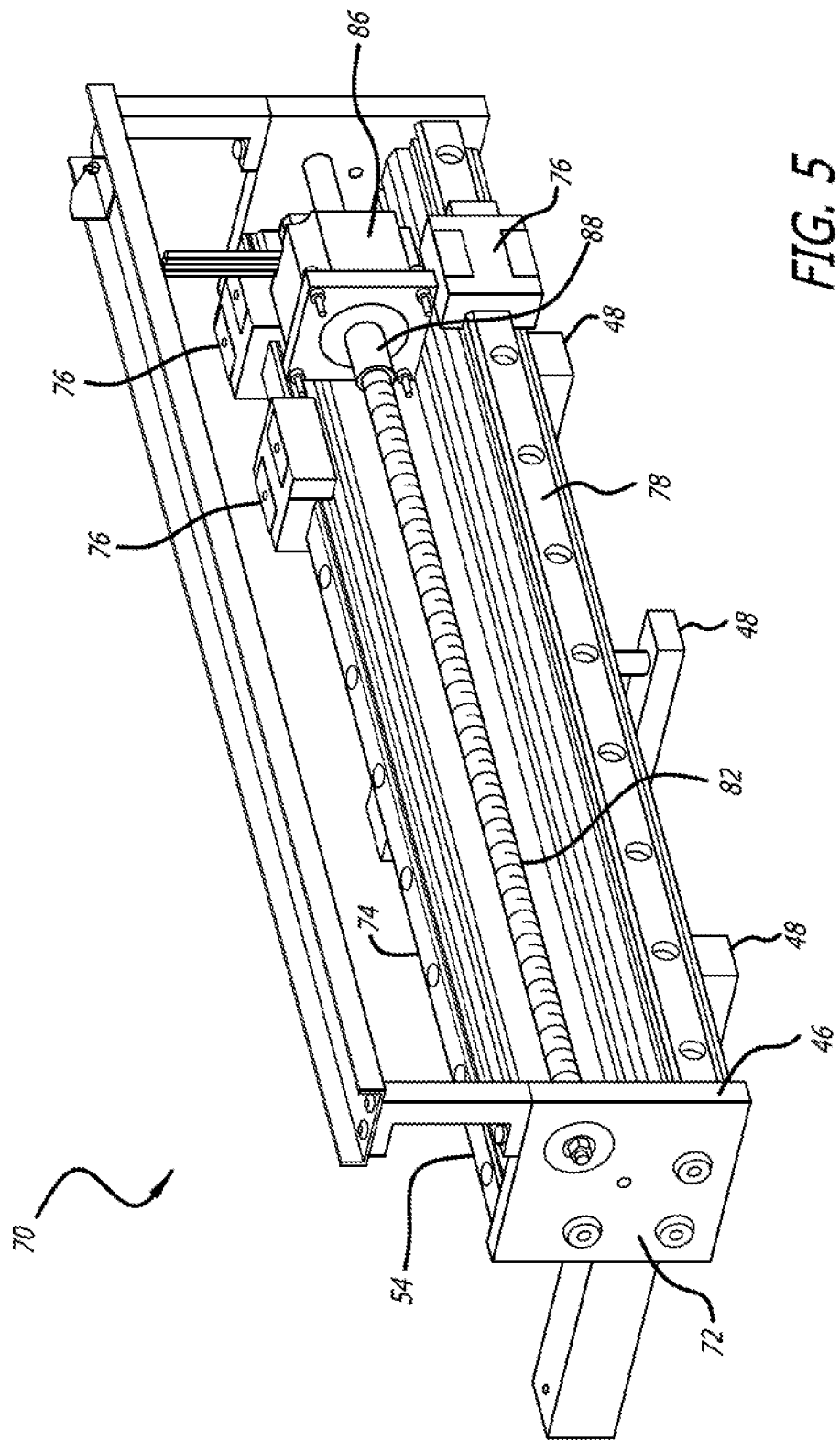
FIG. 5 is a perspective view of an x-axis translation assembly of the three axis positioning system.
Figure 6A:
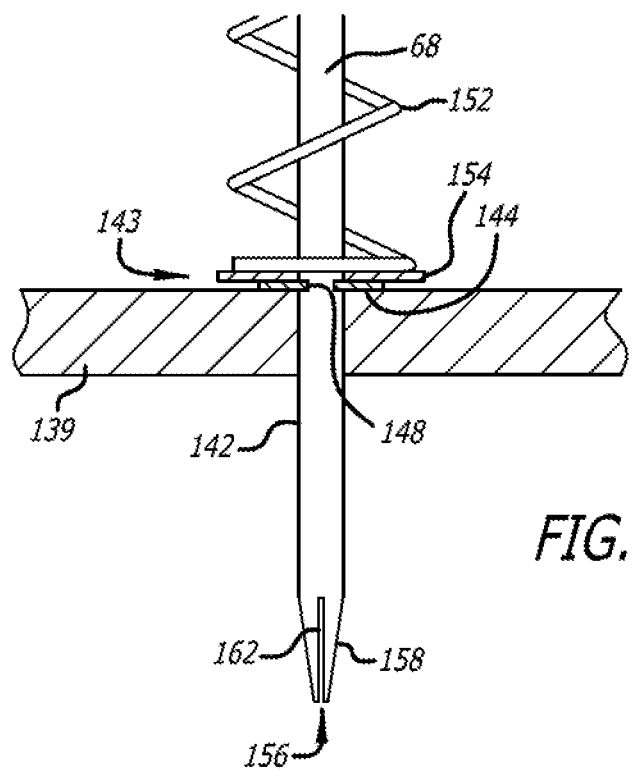
FIG. 6A is an enlarged view in partial section of a bottom plate, pin tool shaft, helical spring clip and washer of a pin tool head assembly embodiment.
Figure 6B:
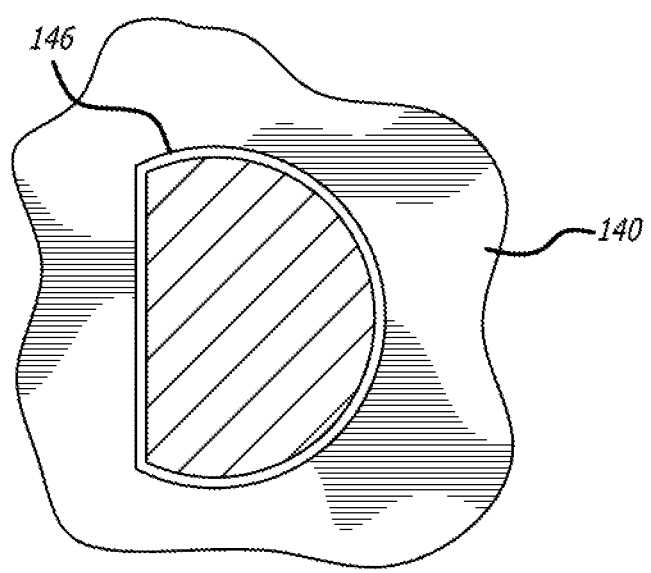
FIG. 6B is a top view in partial section of a shaft of a pin tool in sliding engagement with a cover plate.

FIGS. 5 and 6 illustrate components of the three axis robotic positioning system 18 in more detail. As shown, the three axis robotic positioning system 18 is disposed substantially above the work surface 22 and includes a fixed mount portion 46 which is secured in a fixed relation with the work surface 22. Both the fixed mount portion 46 and the horizontal work surface 22 may be secured in fixed relation to each other on a frame structure 48 which may, in turn, be secured to or otherwise mounted to the housing 12 or frame structure of the housing 12. For the embodiment shown, the frame structure 48 of the work surface 22 and three axis robotic positioning system 18 is mounted to the housing 12 with vibration isolating rubber mounts 52. Also for the embodiment shown, a base portion of the x-axis rail 54 serves as the fixed mount portion 46 of the three axis robotic positioning system 18.

The three axis robotic positioning system 18 includes a z-axis translatable carrier 56 which is disposed above the work surface 22 and which may be controllably positioned in three different axes relative to the work surface 22. The z-axis translatable carrier 56 is coupled to the fixed mount portion 46 of the system or base of the x-axis rail 54 through two other translatable carriers that provide the x-axis and y-axis components of the three axis motion. The three axes of translation of the translatable carrier of the three axis positioning system shown are substantially orthogonal to each other, however, some embodiments may use non-orthogonal axes. The z-axis translatable carrier 56 may be translated in either direction along each of the three axes independently. The movement of the translatable carrier in either direction along each axis may be actuated by a stepper motor actuator which is configured to impart linear motion along the direction of each respective axis.

Position information regarding the position of the translatable carrier along one or more of the three axes may be measured by a linear encoder assembly, such as an optical linear encoder assembly, corresponding to one or more of the axes or by any other suitable method. A linear encoder assembly may include a linear encoder reader head such as an optical linear encoder reader head and a linear encoder strip such as an optical linear encoder strip that are coupled to the controller and may provide position feedback to the controller. A homing switch system may also be used to facilitate the determination of position of the translatable carriers along each of their respective axes. Such a homing switch may be mounted at or near an end of the length of travel or motion of a respective translatable carrier such that the homing switch is activated to open or close an electrical loop, optical loop or the like as the translatable carrier reaches the end of travel at a pre-determined and repeatable position. The electrical or optical loop of the homing switch may be coupled to the controller 28 such that the controller 28 may be programmed to move a translatable carrier to the "home" position which mechanically activates the homing switch at the beginning of a transfer cycle or at any other desired time. For some embodiments, the controller 28 may home one or more of the translatable carriers by sending a home command to one or more motor controllers corresponding to each of the respective stepper motors. Such motor controllers may be located on board 36 or in any other suitable location. Once the home position has been determined, the controller 28 may use the stepper function of the stepper motor actuator to track the number of motion pulses in each direction along the axes in order to calculate or otherwise track the position along each of the axes.

The x-axis rail 54 of the three axis robotic positioning system 18 extends across the processing chamber 14 and is coupled to an x-axis carrier 58 which is coupled to a y-axis carrier 62 which is coupled to the z-axis carrier. The x-axis carrier is configured to translate on the x-axis rail, the y-axis carrier 62 is configured to translate relative to the x-axis carrier in a y-axis direction and the z-axis carrier is configured to translate in a z-axis direction relative to the y-axis carrier 62. All three of the carriers and corresponding carrier rails upon which the carriers move may be respectively coupled together by high precision bearings that are configured to promote low friction linear movement with high precision. The z-axis carrier 56 may be positioned in three axes which are substantially orthogonal to each other for such a configuration. The pin tool head assembly 64 is secured to the z-axis carrier 56 and may also be positioned in the three substantially orthogonal axes. Various embodiments of the rails of the three axis robotic positioning system 18 may include models SR20, RSR12W and HSR20, manufactured by THK Company, Japan.

As discussed above, the z-axis translatable carrier 56 is translatable in the x, y and z axes and is coupled to the fixed mount portion 46 (or base of the x-axis rail) through the y-axis translatable carrier 62 and the x-axis translatable carrier with each translatable carrier configured to move independently of the other carriers in its respective direction. The pin tool head assembly 64 is secured directly to the z-axis translatable carrier 56 which moves up and down on the z-axis rail 66 relative to the y-axis translatable carrier 62 and horizontal work surface 22. The y-axis translatable carrier 62 moves in a y-axis direction front to back on a y-axis track relative to the x-axis translatable carrier 58 and the horizontal work surface 22. The x-axis translatable carrier 58 moves in an x-axis direction side to side relative to the fixed mount portion 46 on the x-axis rail 54. The superposition of movement in each of the x-axis, y-axis and z-axis directions allows the z-axis translatable carrier 56 and pin tool head assembly 64 secured directly thereto to be positioned in three dimensions with respect to the horizontal work surface 22 and functional components disposed on the work surface 22. There may be no need for movement in a rotational orientation as the pin tools 68 of the pin tool head assembly 64 are generally applied at a right angle or perpendicular to nominal upper surfaces of the functional components of the work surface 22. However, an additional axis or axes of motion could be added to the robotic positioning system 18. In addition, although the base portion of the x-axis rail 54 serves as the fixed mount portion 46 and the z-axis translatable carrier 56 serves as a three axis translatable carrier, the various carriers may be mixed and matched as desired in order to achieve the three axes of movement. For example, a base portion of a rail of either the x, y or z axis of a robotic positioning system could serve as the fixed mount portion 46 that is mounted in fixed relation to the work surface 22. Also, either the x, y or z translatable carrier may serve as the three axis translatable carrier of a robotic positioning system 18, so long as the three axis translatable carrier is coupled to the fixed mount portion through translatable carriers of the other two axes.

Referring to FIG. 5, the x-axis rail assembly 70 includes a frame 72 that includes a bottom portion which is secured in fixed relation to the frame structure 48 beneath the rail assembly 70. The work surface 22 is also secured in fixed relation to the same frame structure 48. As such, the bottom of the x-axis rail assembly 70 serves as the fixed mount portion 46 of the three axis robotic positioning system 18. The x-axis rail assembly 70 includes a first x-axis rail 74 upon which bearing cars 76 are slidingly engaged and free to translate along the x-axis direction. The x-axis rail assembly 70 includes a second x-axis rail 78 upon which a bearing car 76 is slidingly engaged and free to translate along the x-axis direction. The x-axis translatable carrier 58 is secured to the bearing cars of the x-axis rail assembly 70 and thus the x-axis translatable carrier 58 is free to move along the x-axis direction riding on the multiple bearing cars 76. A threaded rod 82 is secured between end plates 84 and 85 of the x-axis rail assembly 70. X-axis stepper motor 86 has a threaded collar 88 that is in threaded engagement with the threaded rod 82. The threaded collar 88 is configured to rotate with a rotor of the stepper motor 86 but remain stable in an axial direction relative to the stepper motor body. The stepper motor 86 thus moves along and relative to the threaded rod 82, frame 70 and x-axis when the stepper motor 86 drives the threaded collar 88 which rotates relative to the threaded rod 82. The x-axis stepper motor 86 is also secured in fixed relation to the x-axis translatable carrier 58 and thus drives the x-axis translatable carrier 58 along the x-axis direction when actuated. For such an arrangement, the threaded collar 88 of the stepper motor 86 may include an anti-backlash device in order to maintain high precision linear movement of the x-axis translatable carrier 58. An linear encoder strip 92 is disposed on a front surface of the rail assembly 70 as shown in FIG. 4, which may be read by an encoder head 94 which is secured to the x-axis translatable carrier as shown in FIG. 3. The linear encoder strip 92 may include model RGS40S, manufactured by Renishaw Corporation located in Gloucestershire, England. The linear encoder reader head 94 may include model RGH41, also manufactured by Renishaw Corporation. The linear encoder systems may have a resolution of about 0.5 microns to about 5 microns, more specifically, about 0.8 microns to about 1.5 microns, for some embodiments. The various stepper motor embodiments may include model series 57000, size 23, and model series 43000, size 17, manufactured by Hayden Switch and Instrument Company, Waterbury, Conn.

Referring to FIG. 4, a y-axis rail assembly 96 is secured to the x-axis translatable carrier 58. The y-axis rail assembly 96 includes a frame 95 y-axis rail 98 upon which a bearing car (not shown) is slidingly engaged and free to move along the y-axis direction. The y-axis translatable carrier 62 is secured to the bearing car of the y-axis rail assembly 96 and thus the y-axis translatable carrier 62 is free to move along the y-axis direction riding on the bearing car. A threaded rod 102 is secured between end plates 104 and 105 of the y-axis rail assembly 96. Y-axis stepper motor 106 has a threaded collar 108 that is in threaded engagement with the threaded rod 102. The threaded collar 108 is configured to rotate with a rotor of the stepper motor 106 but remain stable in an axial direction relative to the stepper motor body. The stepper motor 106 thus moves along and relative to the threaded rod 102, frame 95 and y-axis when the stepper motor drives the threaded collar 108 which rotates relative to the threaded rod 102. As with the x-axis assembly 70, the threaded collar 108 of the stepper motor 106 may include an anti-backlash device in order to maintain high precision linear movement of the y-axis translatable carrier 62. A y-axis linear encoder strip 112 is disposed along a top portion of the y-axis rail assembly 96. A y-axis linear encoder reader head (not shown) may be disposed on the y-axis translatable carrier 62 and configured to read the y-axis linear encoder strip 112. The encoder strip 112 and reader head may be the same as or similar to the x-axis encoder strip 92 and reader head 94 discussed above.

A z-axis rail assembly 114 is secured to the y-axis translatable carrier 62 to provide controllable high precision movement along the z-axis direction in combination with x-axis and y-axis movement provided by the respective translatable carriers 58 and 56 in those axes. The z-axis rail assembly 114 includes a z-axis rail 116 upon which one or more bearing cars (not shown) are slidingly engaged and free to translate along the z-axis direction with high precision. The z-axis translatable carrier 56 is secured to the bearing car of the z-axis rail assembly 114 and thus the z-axis translatable carrier 56 is free to move along the z-axis direction riding on the bearing cars. A threaded rod 118 is secured to the z-axis translatable carrier. Z-axis stepper motor 122 is secured to the y-axis translatable carrier 62 by a mount bracket 124 and includes a threaded collar 126 that is in threaded engagement with the threaded rod 118. Thus, when the z-axis stepper motor 122 is actuated and the threaded collar 126 rotated, the threaded rod 118 and z-axis translatable carrier 56 is moved along z-axis relative to the y-axis translatable carrier 62. As with the x-axis and y-axis assemblies, the threaded collar 126 of the stepper motor 122 may include an anti-backlash device 56 in order to maintain high precision linear movement of the z-axis translatable carrier 56.

The positioning of the z-axis translatable carrier 56 along the z-axis direction may be determined by the use of a homing switch as discussed above. For the embodiment shown, a homing switch 128 is disposed in fixed relation to the y-axis translatable carrier 62 near the top end of the z-axis motion of the z-axis carrier 56 such that the z-axis carrier 56 activates the homing switch 128 at the top of the z-axis travel. The homing switch 128 is coupled to the controller 28 which may then "home" the z-axis translatable carrier 56 at the beginning of each sample transfer cycle, or at any other desired time, in order to determine the position of the z-axis translatable carrier 56 thereafter. Such a homing position determination process may also be manually selected by a user. The z-axis rail assembly 114 may also optionally include a linear encoder assembly, such as the linear encoder assemblies discussed above with regard to the x-axis rail assembly 70 and y-axis rail assembly 96, if greater precision is desired for the determination of the position of the z-axis translatable carrier 56.

The x-axis rail 54 and translatable carrier 58 may be configured to provide about 10 inches to about 30 inches of travel in the x-axis direction, more specifically, about 20 inches to about 25 inches of travel in the x-axis direction. The y-axis rail 98 and translatable carrier 62 may be configured to provide about 8 inches to about 16 inches of travel in the y-axis direction, more specifically, about 10 inches to about 12 inches of travel in the y-axis direction. The z-axis rail 116 and translatable carrier 56 may be configured to provide about 2 inches to about 10 inches of travel in the z-axis direction, more specifically, about 3 inches to about 5 inches of travel in the z-axis direction.

As shown in FIG. 6, an imaging camera 132 is secured to the y-axis translatable carrier 62. The imaging camera 132 may be configured to have a focal length or range of focus that matches the distance from the imaging camera 132 to a plane below the camera 132 that is substantially at the level or plane of nominal upper surfaces of the functional elements of the work surface 22. For some embodiments, the work surface 22 may be configured such that some or all of the functional components thereof have a nominal upper surface that is at substantially the same z-axis level or position. This configuration may serve to simplify the programming of the controller 28 for sample transfer procedures. This configuration may also allow the imaging camera 132 in a fixed z-axis position to remain in focus while imaging a nominal upper surface of the functional components in order to better control the sample transfer process. A bar coder reader head 134, as shown in FIG. 2, may be secured to the y-axis translatable carrier 62, y-axis rail 98 or any other suitable portion of the robotic positioning system 10. The same arrangement may be desirable for easy scanning of bar codes disposed on chips, microtiter plates or the like that are placed on mount blocks of the work surface 22 for easy identification and obtaining accurate position data of such components. The bar code reader head 134 may include model NLV-1001, manufactured by Opticon Corporation, Japan.

Referring to FIG. 6, the pin tool head assembly 64 is secured to the z-axis translatable carrier 56 by fasteners such as screws or bolts and is movable and may be positioned in all three x, y and z axes. The pin tool head assembly 64 includes a substantially rigid frame structure 136 having a first vertical support plate 137 and a second vertical support plate 138 spaced laterally from the first vertical support plate 137 and disposed substantially parallel to the first vertical support plate 137. A bottom plate 139 is secured at a first end to the first vertical support plate 137 and secured at a second end to the second vertical support plate 138. The bottom plate 139 has a top surface and a bottom surface that is substantially parallel to the top surface. The bottom plate 139 may have a thickness of about 0.05 inches to about 0.5 inches, more specifically, about 0.1 inches to about 0.2 inches, for some embodiments. The bottom plate 139 may be oriented substantially perpendicular to both the first and second vertical support plates 137 and 138. A cover plate 140 is disposed opposite and spaced vertically from the bottom plate 139. The cover plate 140 is secured to top surfaces of upper ends of the first and second vertical support plates 137 and 138 in an orientation that is substantially perpendicular to both the first and second vertical support plates. The cover plate 140 may have a thickness of about 0.05 inches to about 0.5 inches, more specifically, about 0.1 inches to about 0.2 inches, for some embodiments. An open cavity or window is formed in the middle of the rigid frame 136 between the upper surface of the bottom plate 139, a lower surface of the cover plate 140, and interior surfaces of both the first and second vertical support plates 137 and 138.

An array of pin tools 68 is mounted on the bottom plate 139 and cover plate 140 with a configuration that allows axial translation of the pin tools 68 relative to the frame structure 136 in an upward direction. The pin tools 68 have an elongate shaft 142, a nominal shaft portion and an enlarged portion of the shaft 142 that may include an enlarged portion 143 in the form of a collar member 144 to stop axial movement of the pin tool shaft 142 against either the bottom plate 137 or cover plate 140 of the frame structure 136. For the embodiment shown, the pin tools 68 are disposed in a 4 by 6 pin array with spacing or pitch between adjacent pin tools of about 3 mm to about 10 mm, more specifically, about 4 mm to about 5 mm. The pin tools 68 are disposed in close fitting holes in the bottom plate 139 that have an inside diameter or transverse dimension that corresponds to an outer transverse dimension or diameter of the nominal shaft portion of the elongate shaft 142 of each respective pin tool 68. The amount of clearance between an outer surface of each pin tool 68 and an insider surface of the respective hole in the bottom plate may be about 0.0002 inches to about 0.001 inches. Each pin tool 68 is also disposed in a mating hole or slot in the cover plate 140 which may have similar clearance and may provide additional longitudinal stability for axial movement of the pin tool shaft 142 within the frame structure 136.

Either or both of the pin tool shaft holes or slots in the bottom plate 139 or cover plate 140 may have a keyed configuration that matches a keyed configuration of an outside surface of the pin tool shaft 142 so as to prevent rotation of the pin tool shafts 142 relative to the frame structure 136, but allow unimpeded axial movement of the pin tool shafts 142 relative to the frame structure 136. A top portion 146 of the pin tool shafts 142 shown have a "D" shaped transverse cross section which mates with a respective "D" shaped hole in the cover plate 140. Although the pin tool head assembly 64 embodiment shown has a 4 by 6 pin tool array, other configurations are also contemplated. For example, some arrays of pin tools 68 of a pin tool head assembly 64 may have a row of about 1 pin tool to about 15 pin tools in conjunction with columns of about 2 pin tools to about 30 pin tools, for some embodiments. Some embodiments may have a row of about 3 pin tools to about 10 pin tools in conjunction with columns of about 2 pin tools to about 15 pin tools.

For some embodiments, an enlarged portion 143 of the pin tool shaft 142 may be integrally formed into the shaft 142. For the pin tool embodiments shown, an enlarged portion 143 of the elongate shaft 142 of the pin tools 68 is formed by the separate collar member 144 which may be secured to the elongate shaft 142 by a variety of suitable methods such as a compression fit, adhesive, solder or the like. The collar members 144 shown are clips that are secured by compression fit into circumferential slots or grooves 148 formed into the shafts 142 of the pin tools 68. As the collar member 144 is larger than the pin tool shaft holes in the bottom plate, the enlarged portion or collar member 144 comes to a hard stop against the upper surface of the bottom plate 139 at the end of downward axial translation of the pin tool shaft 142. The enlarged portion 143 of the elongate shafts 142 of the pin tools 68 may be biased in an axial direction against the bottom plate 139 of the frame structure 136 by gravity, a resilient bias member, such as a helical spring 152, or by any other suitable device or method. For the embodiment shown, each pin tool 68 is biased against the bottom plate 139 by a helical spring 152 which is disposed over each elongate shaft 142 between the lower surface of the cover plate 140 and an upper surface of the collar member 142 of each pin tool. A washer or bushing may be disposed adjacent the collar members 144 between the collar member 144 and spring 152 to provide a uniform surface for the spring 152 to push against. The helical spring 152 may have a length in a relaxed uncompressed state that is longer than the distance between the upper surface of the bottom plate 139 and lower surface of the cover plate 140 so as to provide continuous resilient bias against upward axial translation of the pin tool 68. The bias against upward axial translation may also increase as the spring member 152 becomes compressed.

For some embodiments, the pin tool shafts 142 may have a length of about 1 inch to about 4 inches, more specifically, about 2 inches to about 3 inches. The elongate shafts 142 of the pin tools 68 may have an outer transverse dimension or diameter of about 0.03 inches to about 0.1 inches, more specifically, about 0.05 inches to about 0.07 inches, for some embodiments.

Sample reservoirs 156 may be disposed in distal ends or portions 158 of the elongate shafts 142 of the pin tools 68, distal of the enlarged portion 143 of the shaft 142 such which may include the collar member 144. The collar member 144 is disposed and mechanically captured in the window of the frame structure 136 with the distal end 158 of the pin tool shafts 142 extending below the pin tool shaft holes in the bottom plate 139. In this way, the distal ends 158 and sample reservoirs 156 of the pin tools 68 extend below the bottom plate 139 and may be used to access samples, such as arrays of samples disposed in vessels such as microtiter plates. The distal ends and sample reservoirs 156 of the pin tools 68 may also be used to access sample deposition sites, such as arrays of sample deposition sites disposed on a spectrometry chip. For some embodiments, the width of a slot 162 of the sample reservoir of the pin tools may be sized to be greater than an outer lateral transverse dimension of a matrix deposit of a sample deposition site of a spectrometry chip. In this way, a sample from the sample reservoir of the pin tool may be deposited onto the matrix deposit of the chip without the pin tool structure making contact with the matrix material. In other words, the slot of the sample reservoir may be configured to straddle the matrix material of the sample deposition site.

Some embodiments of the sample reservoir 156 may include a thin slot 162 having a width of about 0.2 mm to about 0.5 mm, more specifically, about 0.25 mm to about 0.4 mm, and may have a length of about 0.1 inches to about 0.5 inches, more specifically, about 0.18 inches to about 0.22 inches, depending on the desired amount of liquid volume to be delivered. The frame structure 136 and pin tools 68 may be configured, particularly with regard to the placement of the collar member 144 relative to the distal end 158 of the pin tools 68, such that the distal ends 158 of the pin tools 68 of a pin tool array are coplanar and all lie substantially in a plane that is substantially parallel to the work surface 22. Each pin tool 68 of the array may also be substantially perpendicular to the work surface 22.

Figure 7:
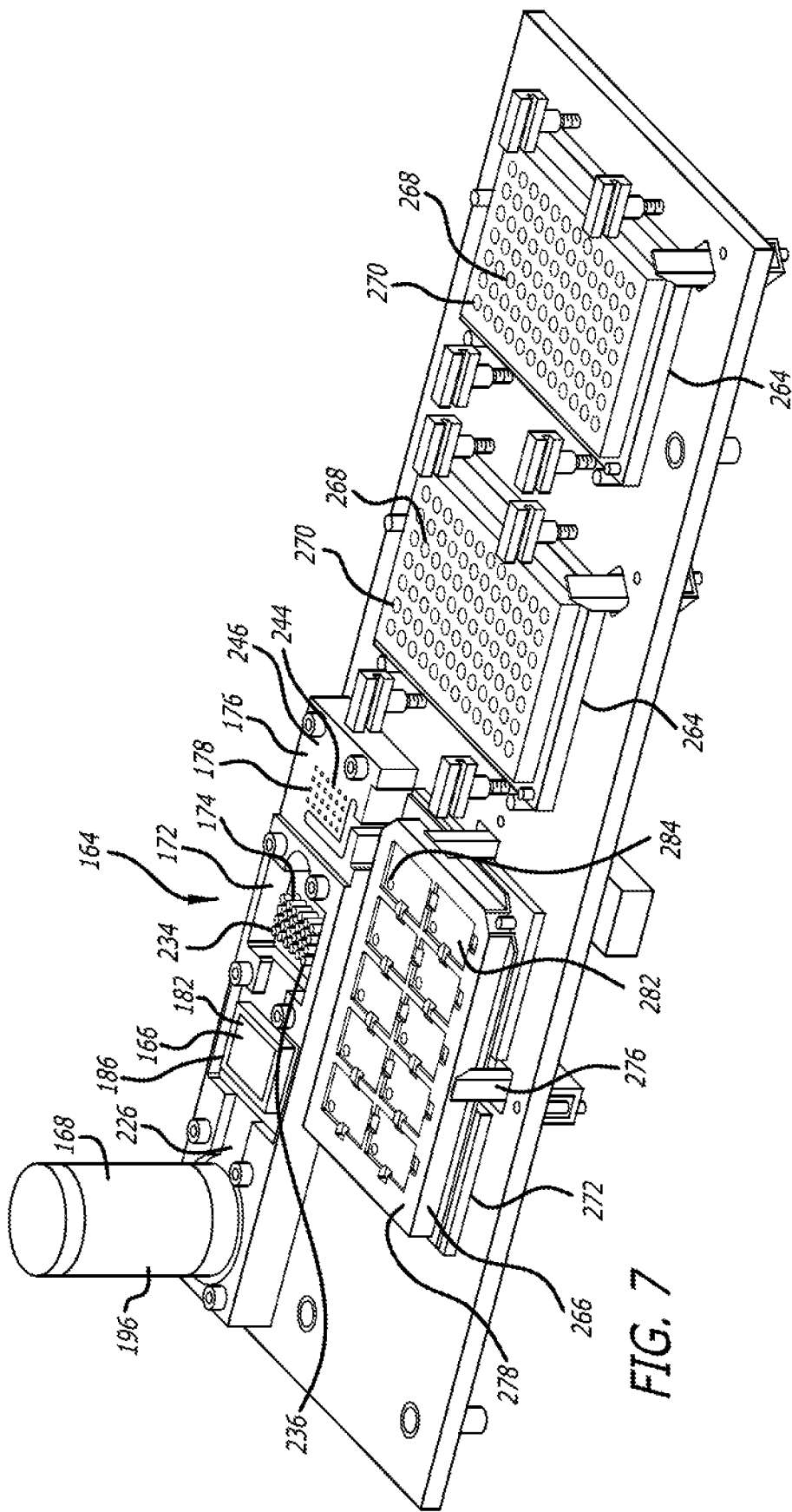
FIG. 7 is a perspective view of a work surface and functional components of the robotic sample transfer device of FIG. 1.

The work surface 22 is generally configured to be disposed in a substantially horizontal orientation and may include one or more functional elements disposed thereon. Because some of the functional elements of the work surface 22 may include fluids disposed in enclosures, the substantially horizontal orientation of the work surface 22 may serve to prevent spillage of the fluids and provide more consistent operation and sample transfer generally. FIG. 7 shows an enlarged perspective view of a work surface embodiment 22 and functional elements disposed thereon. FIGS. 8-11 show additional views and details of the work surface 22 and functional element embodiments associated therewith.

The controller 28 as well as other electronics that control the movement of the pin tool head assembly 64 (that may include a controller with a processor and other sensitive electronic components) as well as control and operation of other components of the transfer device 10 may be disposed above the level of the work surface 22 of the transfer device. With such a configuration, any accidental spills of fluid that occur on the work surface 22 will not compromise the integrity of such electronics.

For the embodiment shown, the work surface 22 is disposed beneath the three axis translatable carrier 56 of the three axis robotic positioning assembly 18 and includes a substantially flat rectangular surface of a rectangular plate upon which the functional elements may be directly or indirectly secured or otherwise mounted. For some embodiments, the work surface 22 itself may be formed from one or more upper nominal surfaces of one or more functional elements discussed herein without the inclusion of a separate flat rectangular surface or plate. For some embodiments, the rectangular plate of the work surface 22 may have a width of about 4 inches to about 16 inches, more specifically, about 5 inches to about 10 inches and may have a length of about 10 inches to about 30 inches, more specifically, about 15 inches to about 20 inches. The plate of the work surface 22 may be secured to frame members 48 which may in turn be secured to the frame of the housing 12 or other structural members of the sample transfer device 10 with solid mounts or vibration absorbing mounts 52 such as the rubber mounts shown.

Referring to FIG. 7, a cleaning block assembly 164 is disposed on and secured to the work surface plate. The cleaning block assembly 164 may have one or more functional elements which are configured to clean each pin tool of a pin tool 68 array of a pin tool head assembly 64 simultaneously. The cleaning block assembly embodiment 164 may be machined from a monolithic block of a strong stable material, such as polymers, such as Delrin®, composites and metals, such as stainless steel, aluminum, which may be anodized, and the like. The cleaning block assembly 164 may include functional elements in the form of a self-filling ultrasonic wash station 166 that is self-filled by a gravity feed supply reservoir 168, pin tool wash or rinse station 172 that includes an array of regularly spaced rinse tubes or fountains 174 that may correspond to each pin tool 68 of the pin tool head assembly 64. The rinse station 172 is disposed between the ultrasonic wash station 166 and a vacuum drying station 176.

The vacuum drying station 176 includes an array of regularly spaced vacuum drying orifices 178 that may correspond to each pin tool of the pin tool 68 head assembly 64. Although not necessary, it may be desirable for the rinse station 172 and vacuum drying station 176 to have an array of rinse tubes 174 or vacuum ports or orifices 178 with a regular spacing that corresponds to the regular spacing of the pin tool array of a pin tool head assembly 64 to be used with these stations and an array size at least as big as the array of pin tools 68 of the pin tool head assembly 64. Even though it may be acceptable for some pin tools 68 of an array which are laterally displaced from a functional element of the cleaning block 164 to press against a surface adjacent a rinse tube 174 or vacuum orifice 178, it may be desirable for all pin tools 68 of an array to be cleaned simultaneously. As such, it may also be desirable for an ultrasonic bath 182 to have inner transverse dimensions that are greater than corresponding outer transverse dimensions of an array of pin tools to be washed in the ultrasonic wash station 166. It may also be desirable for the rinse station 172 and vacuum drying station 176 to have at least as many rinse tubes 174 and vacuum drying orifices 178 as there are pin tools 68 in a pin tool head assembly 64 to be cleaned.

In general, a pin tool array that has been used for transferring samples, such as liquid samples, may then be moved over the work surface 22 so as to align the array with the ultrasonic bath 182 of the ultrasonic wash station 166. The sample reservoirs 156 and distal sections 158 of the pin tools 68 generally, may then be lowered into the ultrasonic bath 182 such that any portion of the pin tools 68 that have been exposed to sample material, will be submerged in the ultrasonic bath 182. An ultrasonic actuator 184 disposed below the ultrasonic bath 182 and cleaning block 164 may be activated to as to emit ultrasonic energy into the bath 182 and promote cleaning and rinsing of each pin tool 68 of the array. The pin tools 68 may be soaked in the ultrasonic bath 182 with ultrasonic energy agitating the water and surface of the pin tool 68 for about 1 second to about 2 minutes, more specifically, about 5 seconds to about 30 seconds, for some process embodiments. The ultrasonic energy emitted into the bath 182 may have a power of about 10 watts to about 100 watts, more specifically, about 20 watts to about 40 watts, and a frequency of about 20 kHz to about 60 kHz, more specifically, about 30 kHz to about 50 kHz, and even more specifically, about 35 kHz to about 45 kHz. The ultrasonic wash fluid used in the ultrasonic bath 182 may include de-ionized water, alcohol, and the like in a volume of about 10 ml to about 1000 ml, more specifically, about 20 ml to about 100 ml.

Figure 10:
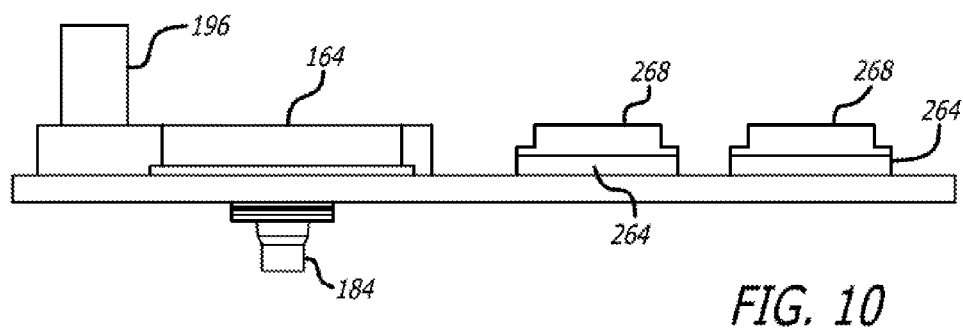
FIG. 10 is an elevation view of the work surface and functional components of the robotic sample transfer device of FIG. 1.

Referring to FIGS. 7 and 10, an upper nominal surface 186 of the ultrasonic wash bath 182 is disposed evenly with a nominal upper surface 188 of the cleaning block assembly 164. The wash bath is disposed below the upper nominal surface 186 between side walls formed into the cleaning block and a top actuator surface 192 of an ultrasonic energy generator or transducer 194. The ultrasonic energy generator 194 interior volume 182 is disposed below the ultrasonic bath 182 and secured thereto by multiple fasteners in a sealed arrangement such that the ultrasonic generator 194 is coupled directly to the wash fluid within the ultrasonic bath 182.

Figure 7A:
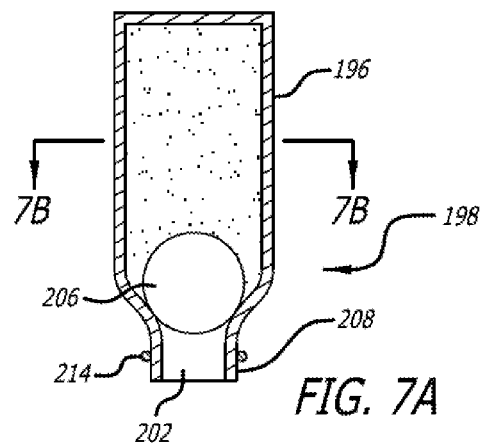
FIG. 7A is an elevation view in partial section of an embodiment of a wash fluid reservoir.
Figure 7B:
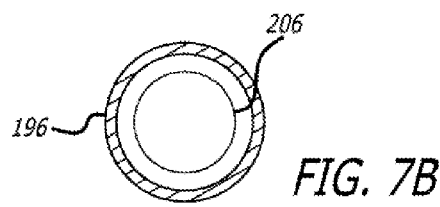
FIG. 7B is a transverse cross section of the wash fluid reservoir of FIG. 7A taken along lines 7B-7B in FIG. 7A.

The ultrasonic wash bath 182 of the ultrasonic wash station 166 is self-filled by a self-leveling gravity feed system supplied by a wash fluid reservoir 168. The wash fluid reservoir 168, as seen in FIG. 7A, may include a generally cylindrical bottle 196 having a ball valve 198 that allows a user to refill the reservoir 168 and couple an outlet port 202 of the reservoir to an inlet port 204 of the ultrasonic wash station 166 without spilling a significant amount of the wash fluid. The wash fluid reservoir 168 is shown tipped up with the outlet port of the reservoir 168 coupled into the inlet port 204 of the wash station 166. The inlet port 204 of the wash station 168 is in fluid communication with the ultrasonic wash bath 182 via a fluid tight conduit (not shown) that extends between the inlet 204 port and wash bath 182 underneath the upper nominal surface 188 of the cleaning block 164. The ball valve 198 may include a spherical ball 206 made of an inert material such as Viton® rubber or the like which is configured to seal against an inside lip of the reservoir bottle 196 and provide a seal. It may be important for the ball 206 of the ball valve 198 to have an overall density which is greater than the density of the cleaning fluid to be used in the reservoir 168. As such, it may be desirable for the ball 206 to have a density which is greater than water, ethanol alcohol, and other suitable cleaning fluids. The outlet port 202 of the wash fluid reservoir 168 may include a cylindrically shaped portion 208 extending from a bottom surface 212 of the reservoir 168. The cylindrically shaped portion 208 may also have an o-ring or similarly configured resilient seal 214 that may seal between the cylindrically shaped portion 208 and an inside surface 216 of the inlet port 204 of the ultrasonic wash station 166. The wash fluid reservoir 168 may have a capacity of about 20 ml to about 1 liter, more specifically, about 40 ml to about 60 ml, for some embodiments.

After the ultrasonic wash bath fluid has been used one or more times, and the operator determines that the wash fluid needs to be changed, the used wash fluid may then be drained through a drain port 218 in the ultrasonic wash bath 182 that is in communication with a flexible fluid tight tube that is coupled to an optional pump 222. When the pump 222 is activated by the controller 28 or other user input, the fluid in the ultrasonic wash 182 shown in FIGS. 2 and 12 may be actively drained from the wash bath 182 through the pump 222 and into a waste fluid tank 224 which is disposed below the processing chamber 14 and shown in FIG. 2. The drainage of the wash bath 182 may also be controlled by a solenoid valve or the like which may optionally be coupled to and controlled by the controller 28.

Thus, the controller 28 may be programmed to drain the ultrasonic wash bath 182 fluid after a predetermined number of uses. As the wash bath 182 is being drained, new clean ultrasonic wash fluid begins to refill the wash bath 182 by force of gravity from the wash fluid reservoir 168 through the fluid tight conduit and into the wash bath 182. As the wash bath 182 begins to fill, the back pressure on the outlet port 202 of the reservoir 168 increases until equilibrium is achieved within the interior volume of the reservoir 168 and wash fluid ceases to flow from the reservoir 168 into the wash bath 182. When the wash fluid becomes dirty again after use, the cycle may be repeated until the reservoir 168 runs out of wash fluid. As such, it may be desirable to construct the bottle 196 of the reservoir 168 from a transparent or translucent material or materials that will make the fluid level within the reservoir 168 visible to a user of the sample transfer device 10. The fluid reservoir 168 also serves to maintain the ultrasonic bath 182 at a desired pre-determined level during use and can be used to automatically add additional cleaning fluid to replace cleaning fluid lost through evaporation, adherence to pin tools 68 and pin tool sample reservoirs 156 after a cleaning cycle or the like.

An optional overflow channel 226 is disposed around the inlet port 204 of the wash fluid reservoir 168, the ultrasonic wash bath 182 and the rinse tubes 174 of the rinse tube station 172. The overflow channel 226 may serve to confine any spilled cleaning fluid to the channel 226 and allow the spilled cleaning fluid to drain down the rinse station drain 228 by force of gravity. The overflow channel 226 may be cut into the upper nominal surface 188 of the cleaning block 164 to a depth of about 0.05 inches to about 0.4 inches, more specifically, about 0.1 inches to about 0.2 inches. A lip 232 of the upper nominal surface 188 of the cleaning block 164 surrounds the ultrasonic bath cavity 182 and forms the upper nominal surface of the ultrasonic wash station 166.

The rinse station 172 includes a plurality of rinse tubes 174 arranged with a regular pre-determined spacing that may be configured to match the regular spacing of the pin tools 68 of a pin tool array to be used with the rinse station 182. The upper ends 234 of the rinse tubes 178 may lie substantially in a plane disposed at substantially the same z-axis level. The upper ends 234 of the rinse tubes 174 may also be at substantially the same z-axis level as the nominal upper level 188 of the cleaning block 164 and form the nominal upper surface of the rinse tube station 172. The rinse tubes 174 may be elongate hollow tubes having an inner lumen 236 with an inner transverse dimension or diameter of about 0.05 inches to about 0.2 inches, more specifically, about 0.07 inches to about 0.1 inches. The inner lumens 236 of the rinse tubes 174 may be coupled by a manifold assembly to a fluid tight tube in fluid communication with a rinse pump 238 which is in turn in fluid communication with a wash fluid supply tank 242 shown in FIG. 3. Once the pin tool or pin tools 68 of a pin tool head assembly 64 are disposed within the rinse tubes 174, rinse fluid may then be expelled vertically from the rinse tubes 174 to provide a continuous flow of rinse fluid over the sample reservoirs 156 and distal section 158 generally of the pin tools 68. The flow of rinse fluid may be maintained for about 1 seconds to about 10 seconds, more specifically, about 3 seconds to about 5 seconds, for some embodiments. The amount of flow of rinse fluid through each individual rinse tube 174 may be about 20 ml per minute to about 100 ml per minute, more specifically, about 20 ml per minute to about 30 ml per minute.

The rinse fluid may include de-ionized water, alcohol including ethanol, or any other suitable cleaning fluid. After the rinse fluid has been expelled from the rinse tubes 174, it flows by force of gravity over the sides of the rinse tubes 174, into the overflow channel 226 discussed above and down the rinse station drain 228. The overflow channel 226 surrounding the rinse tubes 174 may have a depth of about 0.2 inches to about 1 inch, more specifically, about 0.3 inches to about 0.5 inches, for some embodiments. The rinse station drain 228 is a relatively large bore drain that is coupled to the waste fluid tank 224 by a flexible tubing. The bore of the rinse station drain 228 may have a transverse dimension or diameter of about 0.2 inches to about 1 inch, more specifically, about 0.3 inches to about 0.8 inches.

The vacuum drying station 176 includes a plurality of substantially parallel vertical holes 244 disposed in the cleaning block 164 arranged in a regularly spaced array that may be configured to match the regular spacing of the pin tools 68 of a pin tool head assembly 64 to be dried by the vacuum drying station 176. The vertical holes 178 are formed directly into the material of the cleaning block 164 having upper apertures or orifices 178 that lie in substantially the same plane as the upper nominal surface 246 of the vacuum drying station 176. The vertical holes 244 may have an inner transverse dimension or diameter that is larger or just slightly larger than an outer transverse dimension or diameter of the pin tools 68 to be used in the vacuum drying station 176. For some embodiments, the vertical holes 244 may have an inner transverse dimension or diameter of about 0.04 inches to about 0.1 inches, more specifically, about 0.07 inches to about 0.1 inches. The vertical holes 244 may have a depth of about 0.1 inches to about 1 inch, more specifically about 0.3 inches to about 0.5 inches.

A bottom end or bottom orifice (not shown) of each vertical hole 244 may be coupled to a manifold which is coupled to a vacuum holding tank 248, shown in FIG. 2, disposed below the work surface 22 in the lower chamber 44 by a length of flexible tubing (not shown). The flexible tubing may have a wall thickness and mechanical integrity suitable for holding a vacuum or partial vacuum for some embodiments. A valve, such as a solenoid valve (not shown), which may be coupled to and controlled by the controller 28, may be coupled to the flexible tubing in fluid communication with the vacuum storage tank 248 and vertical holes 244 in a configuration that allows the application of stored vacuum in the tank 248 to be applied to the vertical holes 244 when the pin tools 68 of a pin tool head assembly 64 are disposed within the vertical holes 244. If the vacuum storage tank 248 has been emptied of most of the air within the storage tank 248, air will be drawn through the vertical holes 244 at a high rate of flow and through the flexible tubing when the solenoid valve is opened in order to fill the vacuum within the vacuum storage tank 248. For some embodiments, the vacuum storage tank 248 may have an interior volume of about 1 liter to about 3 liters, more specifically, about 1.5 liters to about 2 liters. For some embodiments, the vacuum may be applied to the vertical holes 244 for drying pin tools 68 disposed therein for about 0.1 seconds to about 0.8 seconds, more specifically, about 0.2 seconds to about 0.4 seconds.

Figure 7C:
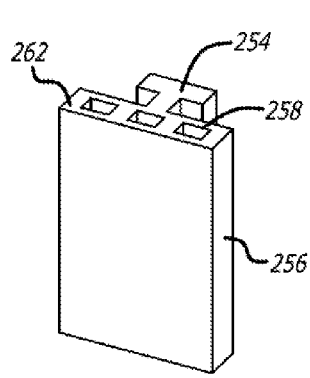
FIG. 7C is a perspective view of an embodiment of a calibration material supply vessel.
Figure 7D:
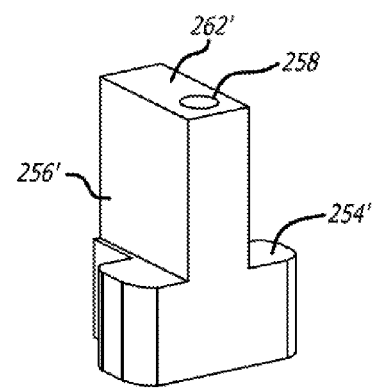
FIG. 7D is a perspective view of an embodiment of a calibration material supply vessel.
Figure 8:
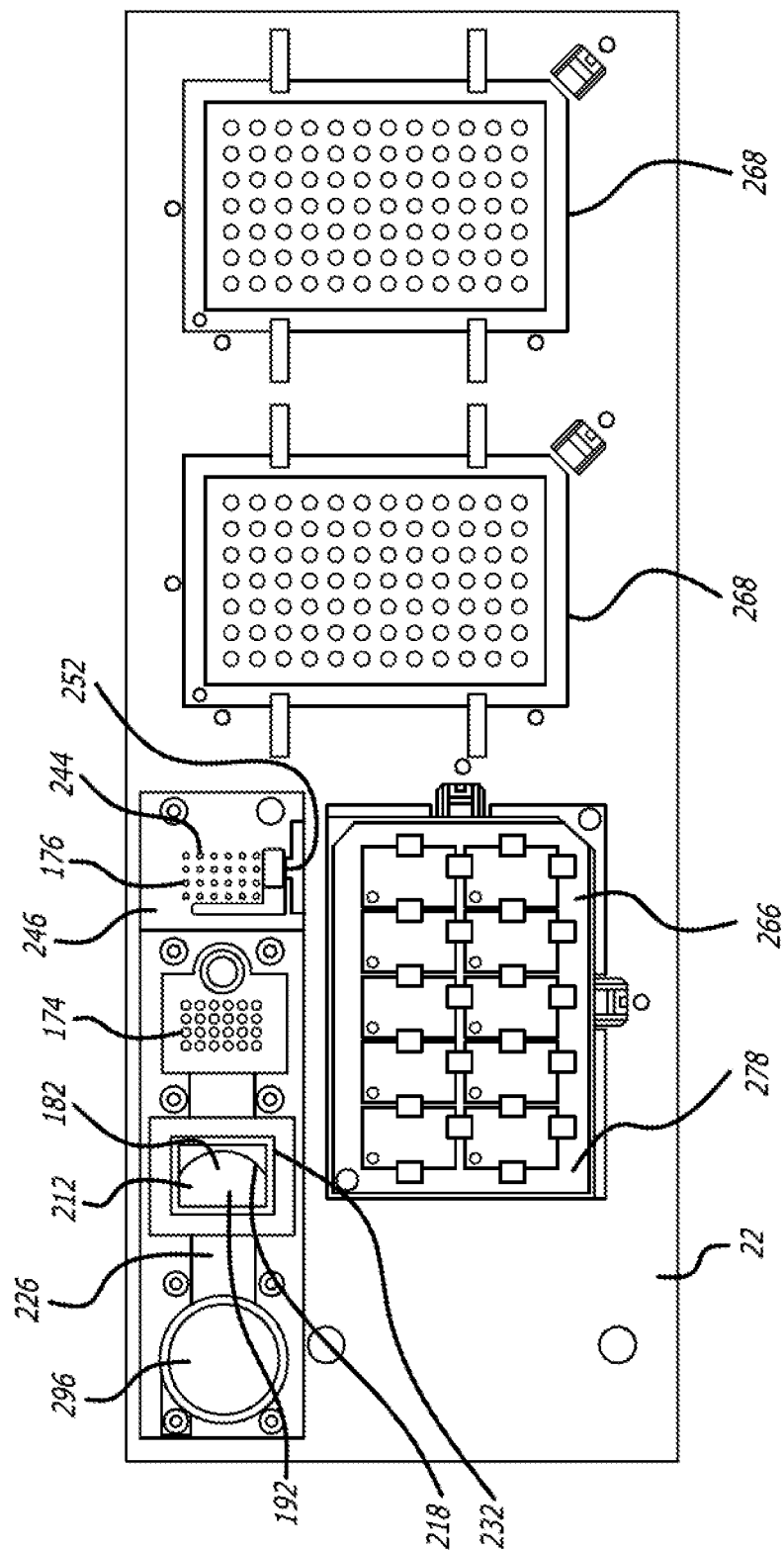
FIG. 8 is a top view of a work surface and functional components of the robotic sample transfer device of FIG. 1.
Figure 9:
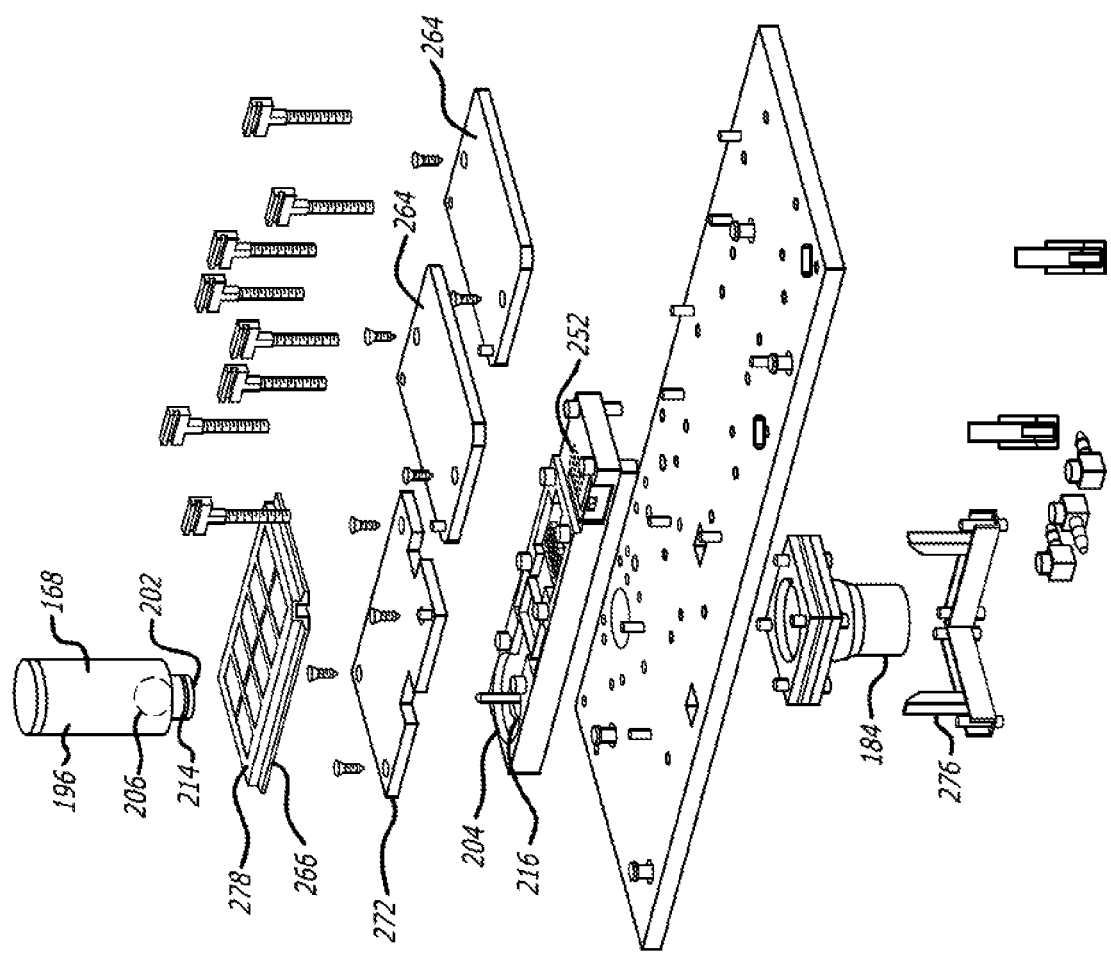
FIG. 9 is an exploded view of the work surface and functional components of the robotic sample transfer device of FIG. 1.

A relieved slot or channel 252 may be formed into a front surface of the cleaning block 164 in front of the vacuum drying station 176. The slot 252 may be configured to accept a rail feature 254 of a multi-well calibration material supply vessel 256 shown in FIG. 7C. The supply vessel 256 may be detachably disposed into the slot 252 by sliding the rail feature 254 of the supply vessel 256 vertically downward into the slot 252 until it hits a stop point. One or more calibration materials may be disposed in the individual wells 258 of the supply vessel and the supply vessel 256 then placed in the slot 252 of the cleaning block 164. The controller 28 may be programmed to dip one or more pin tools 68 to be used for calibration purposes into a pre-determined well of the supply vessel 256 in order to draw in calibration material into the sample reservoir 156 of the pin tool 68 to be used for calibration. Once the calibration material runs out or gets low, or the user decides to use another type of calibration material, the supply vessel 256 may be manually removed from the cleaning block 164 and replaced with another full supply vessel 256. For some embodiments, the supply vessel 256 may have about 1 well to about 10 wells, more specifically, about 2 wells to about 8 wells. FIG. 7D illustrates and embodiment of a supply vessel 256' having a single well 258' and a rail feature 254' that may also be configured to engage slot 252.

The slot 252 of the cleaning block 164 and rail feature 254 and 254' of the supply vessel embodiments 256 and 256' may be configured such that respective upper nominal surfaces 262 and 262' of the supply vessel embodiments are disposed above the upper nominal surface 188 of the cleaning block 164 for some embodiments. This allows the pin tools 68 to be used for calibration purposes to dip into the wells 258 of the supply vessels without the remainder of the pin tools 68 making contact with adjacent cleaning block elements or structures. As such, the rail feature embodiments 254 and 254' and slot 252 may be configured such that the height of the nominal surface 262 of the supply vessel 256 may be disposed above the nominal upper surface 188 of the cleaning block 164 by a distance that is at least the length of a pin tool 68 that needs to be inserted into the calibration material plus the distance below the upper nominal surface of the supply vessel embodiments of the calibration material.

Some of the functional elements of the work surface 22 may be secured to the plate by fasteners such as machine screws or the like and some functional elements, such as microtiter plates, chips and chip mount blocks may be releasably secured to the work surface, or mount block disposed thereon, with elements such as spring loaded toggles, clips, magnets or the like to allow the easy and convenient exchange of such functional elements. Functional elements such as microtiter plates, chips and chip mount blocks may contain samples to be transferred or sample deposition sites that need to be changed as processing takes place and progresses. The work surface shown in FIG. 7 includes two microtiter plate mount blocks 264 disposed adjacent a chip mount block 266. The microtiter plate mount blocks 264 are configured to releasably secure microtiter plates 268 having a uniform and standardized configuration with an array of sample wells 270. This allows such a standardized microtiter plate 268 to be easily mounted and removed from the work surface 22 with some of the important aspects of the microtiter plate 268 (such as sample well location and upper nominal surface location) disposed in a consistent position with respect to the work surface 22.

The chip mount block 266 may also be releasably secured to a mount platform 272 which is secured to the work surface 22 and configured to releasably secure the chip mount block 266 thereto with spring loaded toggles or the like. This allows the chip mount block 266 to be preloaded with one or more chips, such as the spectrometry chip 274 shown in FIGS. 11A and 11B, away from the work surface 22. The chip mount block 266 that has been preloaded with chips 274 may then be releasably secured to the mount platform 272 on the work surface 22 by the toggles 276. The mount platform 272 may be sized to have a thickness or otherwise be configured to position an upper nominal surface 278 of the chip mount block 266 (and chips 274 mounted thereto for some embodiments) at a level which is even with upper nominal surfaces 188 of the cleaning block 164 and other functional elements disposed on the work surface 22.

Figure 11:
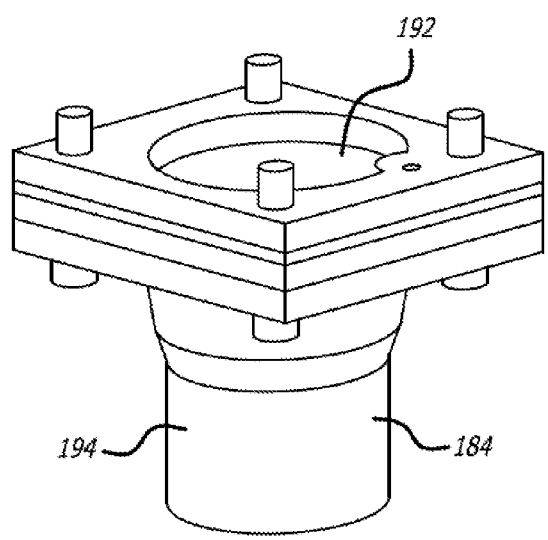
FIG. 11 is an enlarged perspective view of a ultrasound energy generator of the ultrasonic cleaning well disposed on the work surface.
Figure 11A:
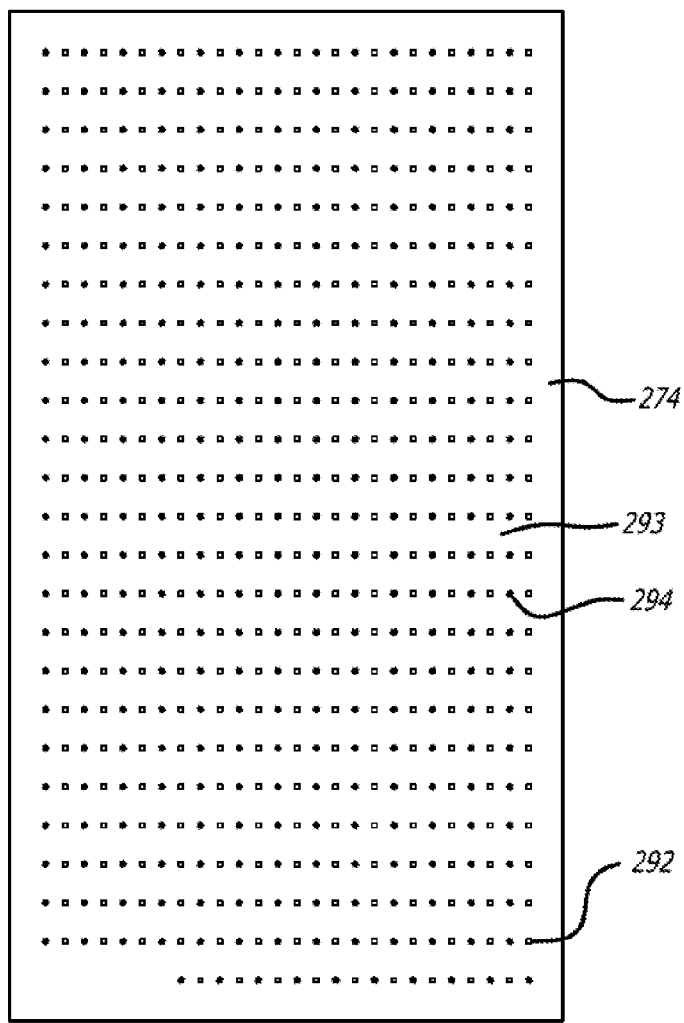
FIG. 11A is a top view of an embodiment of a chip having an array of sample deposition sites disposed thereon.
Figure 11B:
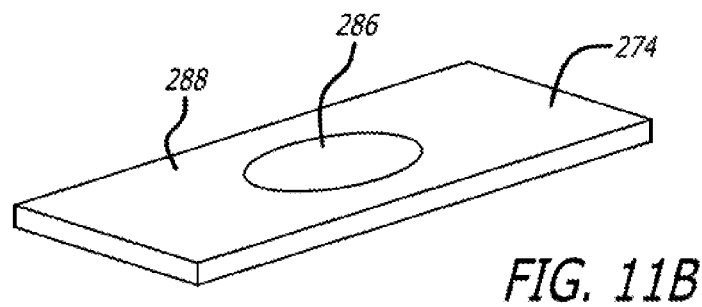
FIG. 11B is a bottom view of the chip of FIG. 11A.
Figure 13:
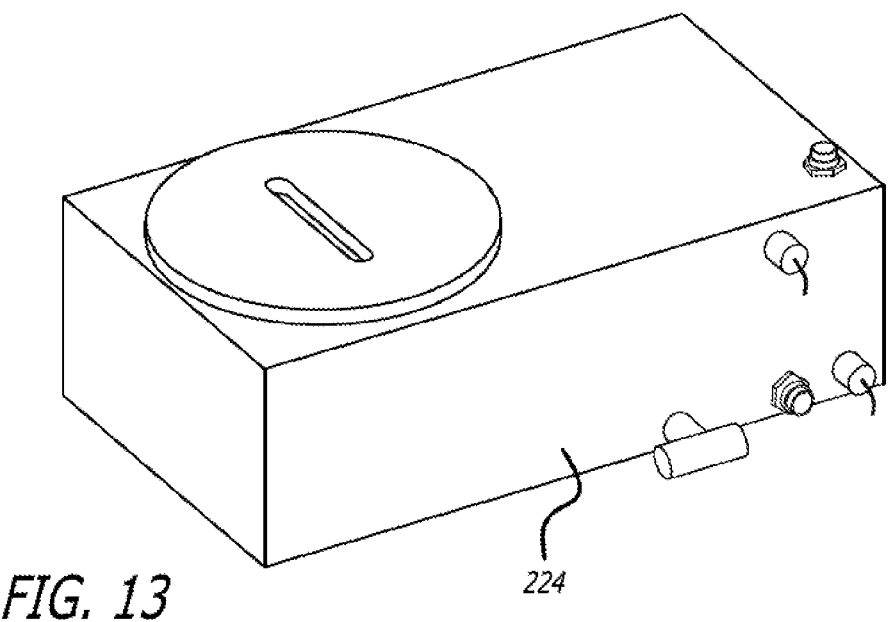
FIG. 13 is a perspective view of a waste fluid tank.
Figure 14:
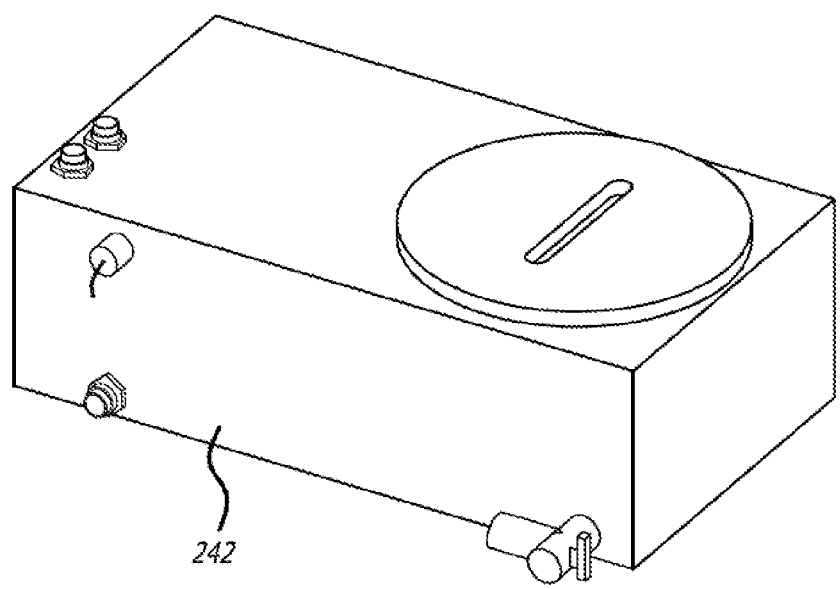
FIG. 14 is a perspective view of a fluid supply tank.

The chip mount block 266 may have one or more chip mount sites 288 or wells which are configured to releasably secure one or more chips 274, such as mass spectrometry chips, having at least one array of sample deposition sites disposed thereon. The chips 274 may be mounted to chip mount sites 282 the chip mount block 266 by gravity, friction, spring loaded toggles, magnets and the like. The chip mount block 266 may also secure the chips 274 thereto by having each chip 274 disposed within a cavity of the chip mount sites 282 formed in an upper surface of the chip mount block 266 which is sized to substantially conform to an outer edge of pre-selected embodiments of chips 274. Such cavities may be used to partially mechanically capture the mounted chips 274 and prevent lateral movement of the chips 274 relative to the chip mount block 266. For the embodiment shown, each chip mount cavity well 282 has a magnetic source, such as a ferrous magnet 284 disposed in a bottom surface of the chip mount well 282. Each chip 274 to be used for such an embodiment, may have a layer of ferrous metal, such as a disc 286 made of steel or the like, secured to a rear surface 288 of the chip 274 as shown in FIGS. 11A and 11B. When such a chip embodiment 274 is placed in a chip mount well 282, the magnet 284 of the chip mount well 282 attracts the disc 286 secured to the chip 274 and holds the chip 274 in the chip mount well 232. By having the magnet 284 of the chip mount well 282 offset from the position of the ferrous metal disc 286, the chip 274 may also be pulled laterally into a corner of the chip mount well 282 in order to register the position of the corner of the chip 274 to a known corner of the chip mount well 282 and provide a reliable positioning of the chip 274 within the chip mount well 282.

Referring to FIGS. 11A and 11B, each chip 274 may include one or more arrays of sample deposition sites 292 which are regularly spaced from each other at periodic intervals on a flat working surface 293 of the chip 274. Also, as discussed above, each chip 274 may have a ferrous metal disc or layer 286 disposed on the rear surface 288 of the chip 274 for releasable mounting purposes. For some embodiments, an array of sample deposition sites 292 on a chip 274 may be configured as a square orthogonal array of sample deposition sites 292 wherein each sample deposition site 292 is disposed an equal distance away from the adjacent sample sites 292 along orthogonal axes that transect the sample sites 292. Such an orthogonal array of sample sites 292 may have a spacing between adjacent sample sites of about 1 mm to about 3 mm, more specifically, about 1.1 mm to about 1.4 mm. For some embodiments, a chip 274 may include two, three or more arrays of sample deposition sites 292, each array having a regular spacing of sample deposition sites 292. Each of the multiple arrays of sample deposition sites 292 may be square orthogonal, linear or have any other desirable configuration. It may also be desirable for one or more arrays of sample deposition sites 292 to have a regular spacing that is different from one or more other arrays of sample deposition sites 292. It may also be desirable for one or more arrays of sample deposition sites 292 to have a regular spacing that is off pitch or out of phase from the pitch or phase one or more other arrays of sample deposition sites 292. For some embodiments, the ferrous metal disc 286 may be made from steel, stainless steel, nickel as well as other suitable ferrous metals. The disc 286 may have a thickness of about 0.01 inches to about 0.1 inches, and a surface area of about 0.08 square inches to about 0.15 square inches.

For some embodiments of the chips 274, the sample deposition sites 292 may include mass spectrometry sample deposition sites, such as MALDI sample deposition sites, which may be arranged in one or more regularly spaced patterns or arrays. For some embodiments, the chip 274 may include a first array of sample deposition sites 292 for sample processing and a second array of sample deposition sites 292 for calibration of the processing equipment. For some embodiments, the regular spacing of the second array of calibration sample deposition sites 292 may be off-pitch from the regular spacing of the first array, as will be discussed in more detail below.

For many of the applications of the robotic sample transfer device 10, it is very important to determine the position of the translatable carriers 56, 58 and 62, and particularly, the three axis translatable carrier 56 relative to the work surface 22 and functional elements of the work surface 22. This is very important so that each pin tool of the pin tool head assembly 64 may be moved to a known position relative to the functional elements with which it must interact in order to transfer samples from one location to another, as well as be moved to known positions of the elements of the cleaning block 164 for proper cleaning of the pin tools 68. For example, it may be important for some sample transfer methods to dip a particular pin tool 68 or set of pin tools 68 into sample wells 270 of a microtiter plate 268 to a pre-determined depth below the upper nominal surface of the microtiter plate 268 and take up a known amount of sample material. The pin tool 68 must then be accurately moved to a sample deposition site 292, such as a spectrometry sample deposition site on a chip 274, without hitting or otherwise interfering with any other elements or components on the work surface 22. The pin tool 68 be brought into precise contact with a pre-determined sample deposition site 292 of the chip 274 with a pre-determined amount of force to deposit a known amount of sample onto the sample deposition site 292. The pin tool 68 may then be precisely moved to the functional elements of the cleaning block 164 and be moved through the progression of cleaning functional elements including the ultrasonic bath 182, rinse station 172 and vacuum drying station 176. Each of these steps requires that the pin tool 68 be moved over the bath 182, respective rinse tube 174 and respective vertical hole or channel 244 of the vacuum drying station 176 and moved vertically downward into functional coupling with these elements without making contact with adjacent structures.

For some embodiments of chips 274, such as some of the spectrometry chip embodiments discussed above, it may be desirable to use features of the chip 274 to facilitate the process of locating or positioning the three axis translatable carrier with respect to the work surface 22 and functional elements of the work surface 22. Some methods of registering the position of a pin tool head assembly 64, and pin tools 68 thereof, of a robotic sample transfer device 10 relative to sample deposition sites 292 on a chip 274 include making use of functional elements having an upper nominal surface at the same z-axis level, for sample transfer device embodiments that have this feature. That is, some embodiments of robotic sample transfer devices 10 have a work surface 22 with a plurality of functional elements, at least two, three, four or more of which have nominal upper surfaces at substantially the same z-axis level. Such robotic sample transfer devices 10 may also have a three axis robotic positioning system 18 with an imaging camera 132 and pin tool head assembly 64 secured to a translatable carrier thereof. For such embodiments, the nominal upper surfaces of functional elements disposed on work surface 22 may be imaged with the camera 132 and the image data of the nominal upper surfaces of the functional elements from the camera processed by an image processor or the like to determine the approximate position of the pin tool head assembly 64 relative to the functional elements.

For some embodiments of the robotic sample transfer device 10, the controller 28 may include an image processor either as a separate component or built into the processor thereof which may be coupled to the imaging camera 132. The approximate position data obtained by the imaging camera 132 may be used to move the camera 132 to a first chip 274 having an array of regularly spaced sample deposition sites 292 and an array of regularly spaced fiducial marks 294 disposed between the sample deposition sites 292. Thereafter, the fiducial marks 294 on the first chip may be imaged with the imaging camera 132 and the image data of fiducial marks 294 on the first chip 274 processed by the image processor. As the fiducial marks 294 on the chip 274 are at known positions relative to the sample deposition sites 292 on the chip 274, the positions of the sample deposition sites 292 may then be determined to a high degree of accuracy. After the fiducial marks have been imaged, feedback regarding a position of the pin tool head assembly 64 may be obtained from one or more linear encoders of three axes of a three axis robotic positioning system. Position may also be obtained from the controller 28 which has tracked the movement of a translatable carrier, such as translatable carrier 56 after carrying out the homing procedure discussed above.

The position data feedback may then be compared with image processing feedback and look up table data to determine the precise position of the pin tools 68 of the pin tool head assembly 64 relative to the sample deposition sites 292 on the first chip 274. This process may then be repeated for one or more other chips 274. Such methods may be used to determine the precise position of the pin tools 68 of the pin tool head assembly 64 with respect to the sample deposition sites 292 on the first chip 274 is determined to within about 1 micron to about 10 microns for some embodiments.

For some embodiments, the location of one or more of the pin tools 68 of the pin tool head assembly 64 is known with respect to the position of the center of field of view or other reference point in the field of view of the imaging camera 132. This position information may be stored in a look up table or the like of the processor. For these embodiments, once the imaging camera 132 images a known feature of a functional element, for example a sample well in the "A-1" position of a microtiter plate, in the center of field of view of the camera the position information may then be used to calculate the position the one or more pin tools 68 in the center of the A-1 well for future processing methods. If the relative position or positions of other features on the work surface 22 are known relative to the imaged feature, then the position of these features may also be calculated. For example, once the position of the "A-1" sample well of a selected microtiter plate is known, then the relative positions of the remaining wells of the microtiter plate may also be calculated.

If the position of the other functional elements of the work surface 22, such as the ultrasonic bath 182, rinse tubes 174, vertical holes 244 of the vacuum drying station 176, microtiter places 268 mounted to microtiter plate mount blocks 264 in addition to the wells 270 of the plates 268 are known with respect to the position of the imaging camera center of field of view or some other reference position in the imaging camera field of view and this position data is stored in a look up chart, then the position of any of the functional elements relative to one or more of the pin tools 68 of the pin tool head assembly 64 can be determined by the controller 28. Thus, the controller may then use the position information to move one or more of the pin tools 68 or other devices secured to the z-axis translatable carrier to the functional elements for various processing methods. The initial positioning of the center of field of view or other reference point of the imaging camera 132 may be carried out manually in order to teach the controller with regard to the position of each of the functional elements. For some functional element embodiments, such as embodiments of the ultrasonic bath 182 of the ultrasonic wash station, precise position data may not need to be generated as the bath is sufficiently large to accommodate the pin tools 68 of the pin tool head assembly 64 with a relatively large amount of space around the pin tools 68

The wash fluid supply tank 242 may be disposed in the lower storage tank chamber 44 below the work surface 22 and processing chamber 14 as shown in FIG. 3. An external wash fluid supply tank coupling may be disposed on or in fluid communication with the wash fluid supply tank 242 for optionally coupling additional capacity to the internal wash fluid tank 242. As discussed above, the wash fluid tank 242 is coupled to the rinse tubes 174 of the rinse station 172 by flexible tubing through a fluid pump 238 shown in FIG. 12. The wash fluid supply tank 242, as shown in more detail in FIG. 14 may have a substantially rectangular shape having a length of about 10 inches to about 25 inches, a width of about 5 inches to about 10 inches, and a height of about 4 inches to about 8 inches. The wash fluid tank 242 may be made from lightweight durable polymer materials such as polyethylene, polypropylene and the like and may have a capacity of about 1 liter to about 10 liters, more specifically, about 2 liters to about 4 liters. The wash fluid tank 242 may include a liquid level sensor disposed in a wall of the tank 242 that is configured to measure the level of fluid disposed within the tank. The tank may also include a removable access cover or plate that is generally disposed on a top surface of the tank and configured to allow access by an operator to the interior volume of the tank for cleaning, maintenance etc. The tank may also include two or more orifices for fluid communication with fill tubes, drain tubes and the like.

The waste fluid storage tank 224 may also be disposed in the lower storage tank chamber 44 below the work surface 22 and processing chamber 14 adjacent the rinse fluid supply tank 242, as shown in FIG. 3. An external waste fluid storage tank coupling may be disposed on or otherwise in fluid communication with the waste fluid storage tank 224 for optionally coupling additional capacity to the internal waste fluid storage tank 224. As discussed above, the waste fluid tank 224 is in fluid communication with the gravity drain 228 of the rinse station 172 by flexible tubing. The waste fluid tank 224 is also in fluid communication with the ultrasonic wash bath 182 of the ultrasonic cleaning station 166 through a flexible tubing and fluid pump 222 that may be used to drain the ultrasonic bath 182. The waste fluid storage tank 224, as shown in more detail in FIG. 13 may have a substantially rectangular shape having a length of about 10 inches to about 25 inches, a width of about 5 inches to about 10 inches, and a height of about 4 inches to about 8 inches. The wash fluid tank 224 may be made from lightweight durable polymer materials such as polyethylene, polypropylene and the like and may have a capacity of about 1 liters to about 10 liters, more specifically, about 2 liters to about 4 liters. The waste fluid tank 224 may include a liquid level sensor disposed in a wall of the tank 224 that is configured to measure the level of fluid disposed within the tank. The tank may also include a removable access cover or plate that is generally disposed on a top surface of the tank and configured to allow access by an operator to the interior volume of the tank for cleaning, maintenance etc. The tank 224 may also include two or more orifices for fluid communication with fill tubes, drain tubes and the like. Either or both of the wash fluid supply tank 224 and waste fluid tank 242 may be coupled to visual tank fluid level indicators (not shown) on side walls of the housing 12 in order to allow an operator of the system to quickly and intuitively check the fluid levels of the tanks 224 and 242. For some embodiments, the visual indicators may include lengths of clear tubing coupled to the interior cavity of the tanks and extending along a vertical slot cut in the respective side wall of the housing with the end of the clear tubing extending to a location above the top of the tank to which it is coupled. The clear tubing disposed adjacent the vertical slot may also contain a floating ball to visually highlight the level of liquid in the clear tubing.

Referring again to FIG. 12, the pump housing assembly 296 is shown that includes the fluid pump 238 used for moving rinse fluid from the wash fluid supply tank to the rinse tubes 174 of the fluid rinse station 172. A vacuum pump 298 coupled to the vacuum storage tank 248 and configured to generate a vacuum within an interior volume of the vacuum storage tank 248 is also disposed within the pump housing 296. The fluid pump 222 coupled between the ultrasonic wash bath 182 and waste fluid storage tank 224 is also disposed within the housing 296. A solenoid valve 299 for coupling the vacuum within the interior volume of the vacuum storage tank 248 to the vacuum drying orifices 178 of the vacuum drying station 176 is also disposed in the pump housing assembly 296. The rinse fluid pump 238, vacuum pump 298, solenoid valve 299 and ultrasonic bath emptying pump 222 may all be coupled to and controlled by the controller 28 so as to be activated and stopped at appropriate times or intervals for proper cleaning of pin tools 68 or other end results.

For some applications of system calibration as well as other methods of use of the robotic sample transfer device embodiments 10, it may be desirable to have a single pin tool 68 of a pin tool array of a pin tool head assembly 64 deployed or otherwise configured for use. It may also be desirable to have a reduced number of pin tools 68 of a pin tool array configured for use, while the remaining pin tools of the pin tool array are disposed in a retracted state in an upward direction or otherwise deactivated from use. For some embodiments of pin tool head assemblies 64, a pin tool displacement block may be used to selectively retract one or more pin tools 68 of a pin tool array in a proximal or upward direction so as to leave only the desired active pin tools 68 extending downward and configured for use.

Some embodiments of a pin tool displacement block for selectively displacing at least one pin tool 68 of a pin tool head assembly 64 of a robotic sample transfer device 10 in an axial direction include a block body having a bottom surface and a plurality of parallel slots formed into the block body portion. The parallel slots may be substantially perpendicular to the bottom surface with a predetermined regular spacing configured to correspond to regular spacing of pin tools 68 of a pin tool head assembly 64. The parallel slots may have a transverse dimension which is sized to allow easy movement of a width of a nominal shaft of the pin tools in the slots but restrictive of movement of an enlarged portion of the shaft of the pin tools.

The block body portion may also include at least one relieved portion or channel that may extend from the top surface of the block body portion in a direction which is substantially perpendicular to the bottom surface in one or more of the parallel slots. The relieved portion may have a transverse dimension sized to allow easy movement in an axial downward direction of not only the nominal shaft portion of a respective pin tool 68 but also and enlarged portion of a pin tool shaft and be configured to mechanically capture the enlarged portion of a pin tool disposed therein in a lateral direction. The enlarged portion of the pin tool shaft may be greater in transverse dimension than the transverse dimension of the slot but less in transverse dimension than a transverse dimension or diameter of the relieved portion and which extends from a top surface of the block body towards the bottom surface. For some embodiments, the parallel slots may have a width of about 0.04 inches to about 0.2 inches, more specifically, about 0.07 inches to about 0.1 inches, and a spacing or pitch of about 0.1 inches to about 0.5 inches, more specifically, about 0.15 inches to about 0.2 inches. Some embodiments may have a slot length of about 0.2 inches to about 2 inches, more specifically, about 0.5 inches to about 1.2 inches, and even more specifically, about 0.7 inches to about 1 inch. For some embodiments, the relieved portion or channel may have a diameter or transverse dimension of about 0.1 inches to about 0.3 inches, more specifically, about 0.15 inches to about 0.25 inches, and even more specifically, about 0.18 inches to about 0.22 inches.

For some embodiments, the enlarged portion of a shaft of a pin tool 68 may include a collar member and the stop surface of the at least one relieved portion may be configured to prevent axial movement of the collar member and mechanically capture a collar disposed therein member to prevent lateral displacement of the block body when the block is deployed in a pin tool head assembly 64. If more than one relieved portions or channels are disposed in a single block body portion, it may be desirable for the relieved portions to have a regular spacing that corresponds to a regular spacing of the pin tools 68 of a pin tool head assembly 64 for which the block is to be used.

For some embodiments, the relieved portion or channel may extend either partially or completely from the top surface of the block body portion to the bottom surface of the block body portion. For some embodiments wherein the relieved portion extends only partially from the top surface of the block body portion, the relieved portion may terminate at a stop surface which is spaced from the bottom surface. The top surface and bottom surface of the block body portion may be substantially flat and substantially parallel to each other for some embodiments. Some embodiments of pin tool displacement blocks may have a reversible configuration wherein when the block is oriented in a first direction and deployed, a first pin or set of pins is active and when flipped over 180 degrees or otherwise oriented a second direction and deployed, a second pin or set of pins is active which is different from the first set. For such embodiments, it may be desirable for the relieved portions to extend only partially from a first surface to a second surface of the block body portion.

Embodiments of the block body portion may optionally include a handle member extending from and secured to the body portion for more convenient handling by a user of the device. The handle member may be a thin but rigid extension of the material of the block body portion that is easily gripped by a user and extends away from the block body portion with material relieved from both the top surface and bottom surface to allow easy access and gripping. The block body may be made from an inert material, such as Teflon®, Delrin® or the like and may have a width of about 0.4 inches to about 3 inches, more specifically, about 0.8 inches to about 1.2 inches, a length of about 0.5 inches to about 4 inches, more specifically, about 1.5 inches to about 2.5 inches, and a height or thickness of about 0.2 inches to about 1.5 inches, more specifically, about 0.3 inches to about 0.7 inches.

Figure 15:
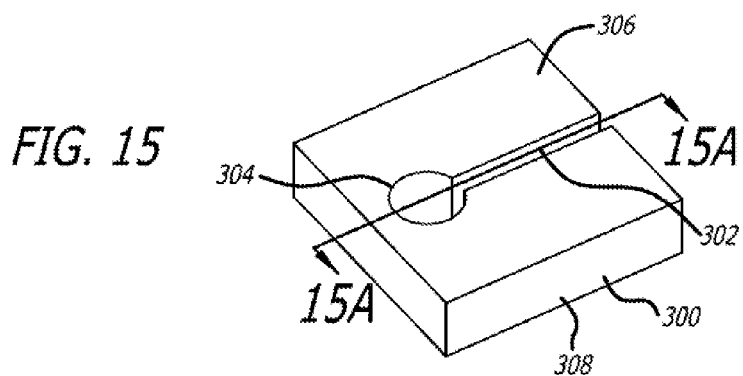
FIG. 15 is a perspective view of a pin tool displacement block for selectively displacing a pin tool of a pin tool head assembly.
Figure 16:
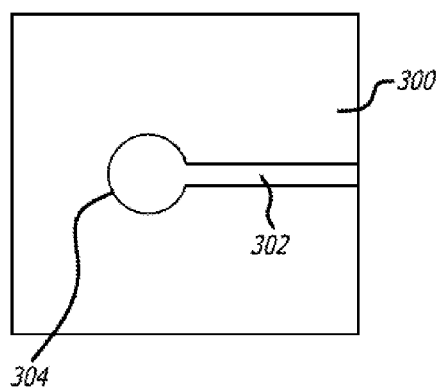
FIG. 16 is a top view of the pin tool displacement block of FIG. 15.
Figure 15A:
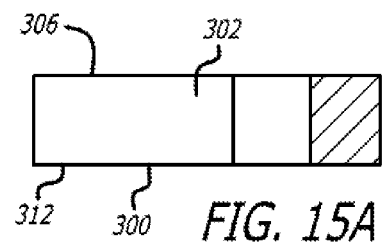
FIG. 15A is a sectional view of the block of FIG. 15 taken along lines 15A-15A.

FIGS. 15 and 16 illustrate a simplified pin tool displacement block 300 having a single slot 302 with a single relieved portion or channel 304 disposed in the slot 302. The relieved portion 304 extends from a top surface 306 of the block body 308 portion towards a bottom surface of the block body portion and extends through the block body portion 308 completely from the top surface 306 to a bottom surface 312, as shown in FIG. 16. The pin tool displacement block 300 may have the same or similar features, dimensions or materials as the features, dimensions or materials of the pin tool displacement block embodiments discussed above.

Figure 17A:
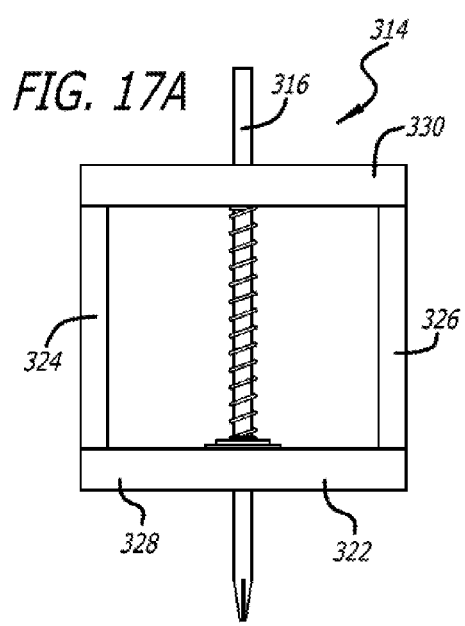
FIG. 17A is a front view of the pin tool head assembly of FIG. 17.
Figure 17:
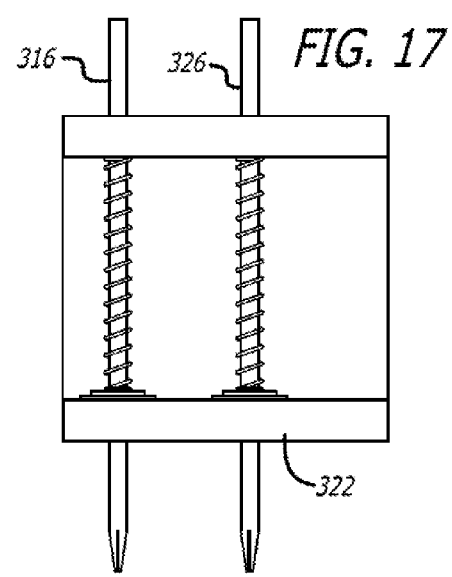
FIG. 17 is an elevation view of a pin tool head assembly embodiment including two spring loaded pin tools.

FIG. 17 is an elevation view of a simplified pin tool head assembly 314 having a first pin tool 316 and second pin tool 318 mounted in a frame 322 of the pin tool head assembly 314. The frame 322 includes a first side plate 324, a second side plate 326, a bottom plate 328 and a cover plate 330. All four plates are secured to adjacent plates at their ends in a perpendicular orientation. The first and second side plates 324 are substantially parallel to each other and the cover plate 328 and bottom plate 330 are substantially parallel to each other. The pin tools 316 and 318, which may have the same or similar features, dimensions or materials as the features, dimensions or materials of the pin tool embodiments 68 discussed above, have a "D" shaped transverse cross section in an upper portion that mates with a corresponding "D" shaped hole in the cover plate 330. A resilient member in the form of a helical spring 152 is disposed over each pin tool 316 and 318 between the cover plate 330 and washer 154 disposed towards the bottom of each pin tool 316 and 318. The washers 152 of the pin tools 316 and 318 are held axially in place by compression clips or collar members 144 that are secured to circumferential grooves 148 in an outer surface of each pin tool shaft 142. As such, each pin tool 316 and 318 is resiliently biased in a downward direction both by the weight of the pin tool itself and the helical spring 152. The helical springs 152 have an axial length in a relaxed uncompressed state that is longer than the distance between an inside surface of the cover plate 330 and inside surface of the bottom plate 328.

Figure 18:
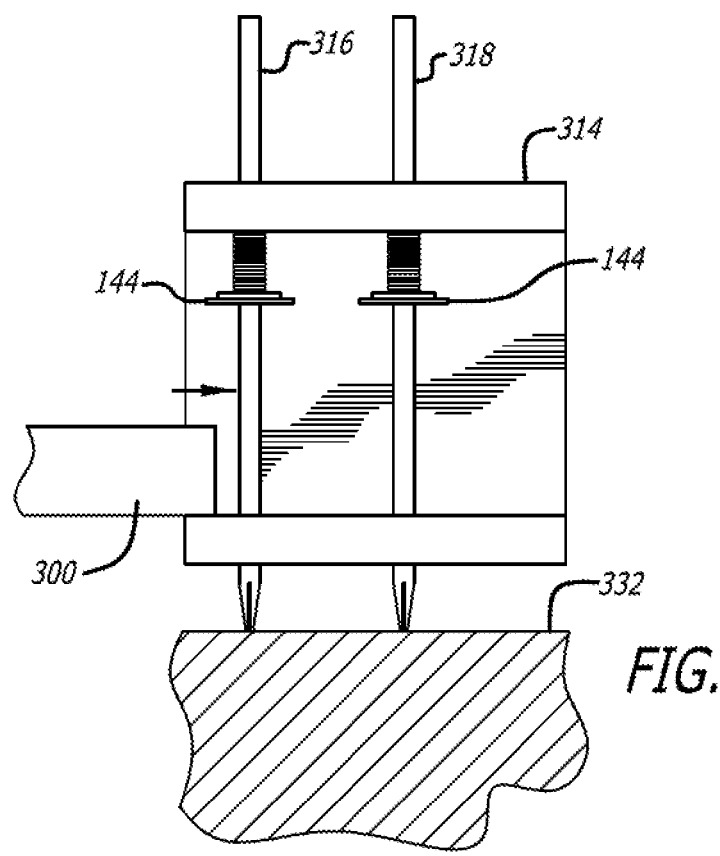
FIG. 18 is an elevation view of the pin tool head assembly of FIG. 17 with the pin tools displaced in a proximal direction.
Figure 19:
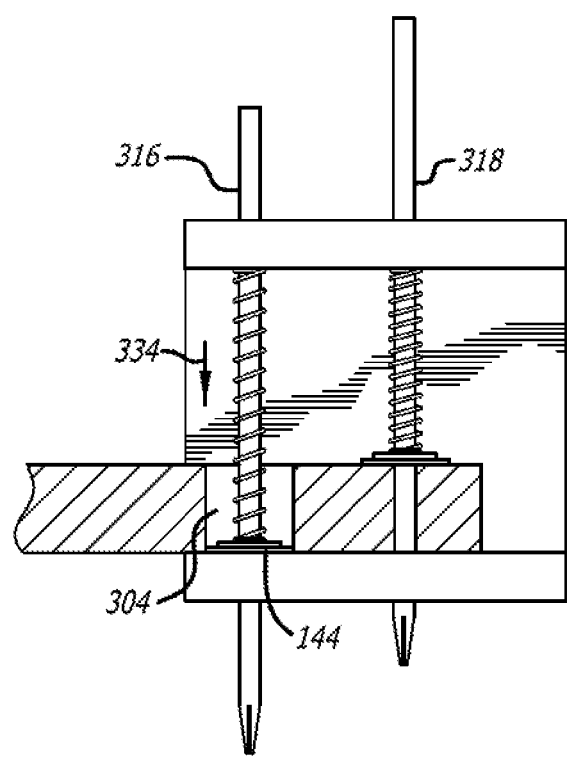
FIG. 19 is an elevation view of the pin tool head assembly with the pin tool displacement block engaged.
Figure 20A:
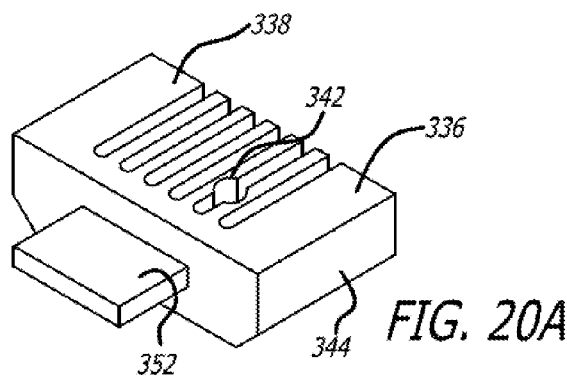
FIGS. 20A-20D illustrate an embodiment of a pin tool displacement block, single pin configuration.
Figure 20B:
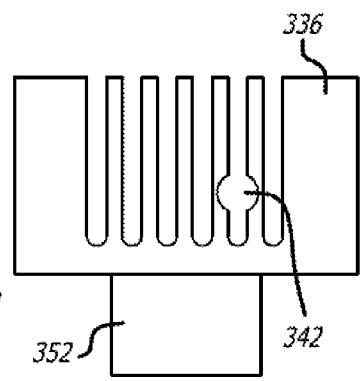
Figure 20C:
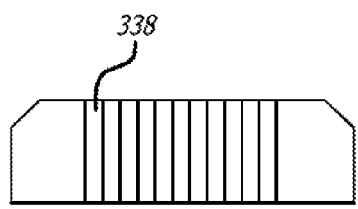
Figure 20D:
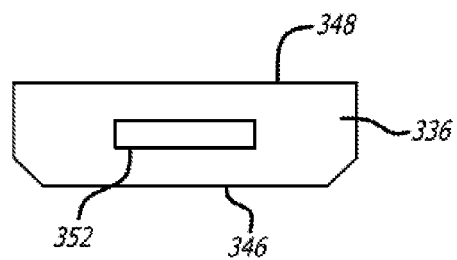
Figure 21A:
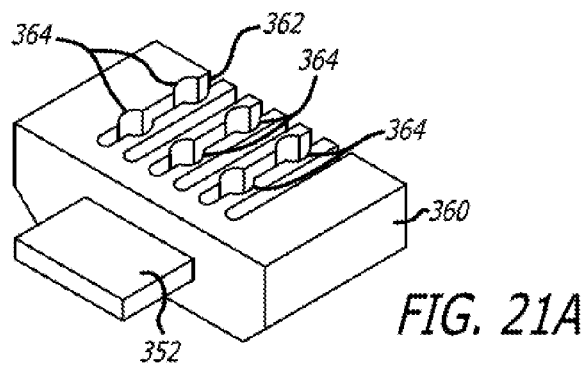
FIGS. 21A-21D illustrate an embodiment of a pin tool displacement block, six pin configuration.
Figure 21B:
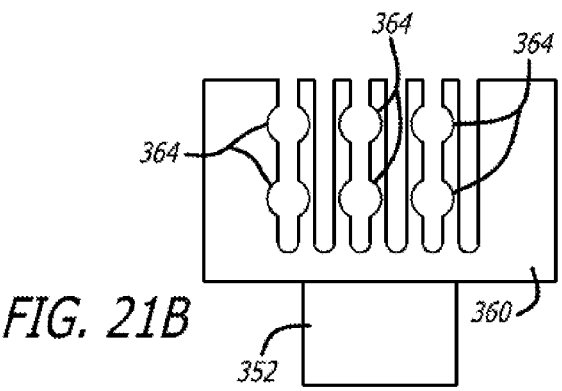
Figure 21C:
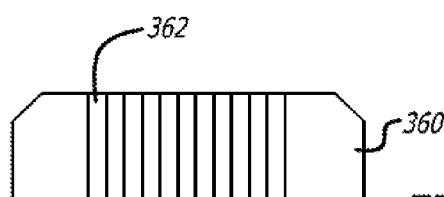
Figure 21D:
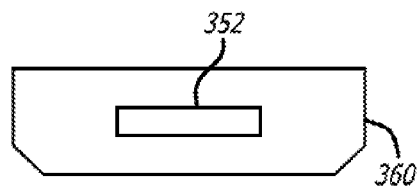

FIGS. 18 and 19 illustrate an embodiment of a method of displacing a pin tool of the pin tool head assembly 314 of a robotic sample transfer device with the pin tool displacement block 300 discussed above. As shown in FIG. 18, the pin tool head assembly 314 is brought down vertically into contact with a flat surface 332 in order to displace the pin tools 316 and 318 axially in an upward direction. In this position, the enlarged portions of the pin tool shafts or collar members are displaced axially from the inside surface of the bottom plate 328 as shown. The slot 302 of the pin tool displacement block 300 is then aligned with the row of pin tools 316 and 318 and advanced into the pin tool head assembly 314 as shown by arrow in FIG. 18. Once the relieved portion 304 in the slot 302 of the pin tool displacement block 300 is aligned coaxially in a vertical direction with the first pin too shaft 316, the pin tool head assembly 314 may then be raised and retracted from the flat surface 332 to allow the pin tools 316 and 318 of the pin tool head 314 assembly to resume a relaxed state. As the pin tool shafts 316 and 318 return to their nominal relaxed positions, the collar member 144 of the first pin tool 316 passes through the relieved portion 304 of the pin tool displacement block 144 and comes to rest on the inside surface of the bottom plate 328. However, the collar member 144 of the second pin tool 318 comes to rest on the upper surface of the pin tool displacement block 300 in an axially retracted state with the distal tip of the pin tool axially retracted from the plane of the first pin tool by a length, indicated by arrow 334, which is substantially equal to the thickness or height of the pin tool displacement block 300.

FIGS. 20A-20D illustrate an embodiment of a pin tool displacement block 336 for use with a 6×4 pin tool array of a pin tool head assembly 64. The pin tool displacement block 336 includes 6 parallel slots 338 that have a regular spacing that is configured to match that of an array of pin tools of a pin tool head assembly 64. A single relieved channel 342 is disposed in a second parallel slot 338 of the block 336 in order to allow a single pin tool in a 2-2 position of the array to be configured for use after deployment of the pin tool displacement block into the pin too head assembly. The pin tool displacement block 336 may have some or all of the features, dimensions or materials as the features, dimensions or materials of any of the pin tool displacement blocks discussed above. The pin tool displacement block 336 includes a first parallel slot, a second parallel slot, a third parallel slot, a fourth parallel slot, a fifth parallel slot and a sixth parallel slot. The pin tool displacement block includes a block body 334 having a bottom surface 346 with the 6 parallel slots formed into the block body portion 344 substantially perpendicular to the bottom surface 346 with a predetermined regular spacing that may be configured to correspond to regular spacing of pin tools 68 of a pin tool head assembly 64. The parallel slots 338 may have a transverse dimension which is sized to allow easy movement of a width of a nominal shaft of the pin tools 68 in the slots 338 but restrictive of movement of an enlarged portion 143 of the shaft of the pin tools 68. For some embodiments, the parallel slots 338 may have a width of about 0.04 inches to about 0.02 inches, more specifically, about 0.07 inches to about 0.1 inches, and a spacing or pitch of about 0.1 inches to about 0.5 inches, more specifically, about 0.15 inches to about 0.2 inches. Some embodiments may have a slot 338 length of about 0.2 inches to about 2 inches, more specifically, about 0.5 inches to about 1.2 inches, and even more specifically, about 0.7 inches to about 1 inch. For some embodiments, the relieved portion or channel 342 may have a diameter or transverse dimension of about 0.1 inches to about 0.3 inches, more specifically, about 0.15 inches to about 0.25 inches, and even more specifically, about 0.18 inches to about 0.22 inches.

The relieved channel 342 extends from the top surface 348 completely through the block body portion 344 in a direction which is substantially perpendicular to the bottom surface 346. The relieved channel or portion 342 may have a transverse dimension sized to allow easy movement in an axial downward direction of not only the nominal shaft portion of a respective pin tool 68 but also and enlarged portion 143 of a pin tool shaft and be configured to mechanically capture the enlarged portion 143 of a pin tool 68 disposed therein in a lateral direction. Embodiments of the block body portion 344 may optionally include a handle member 352 extending from and secured to the body portion for more convenient handling by a user of the device. The handle member 352 may be a thin but rigid extension of the material of the block body portion 344 that is easily gripped by a user and extends away from the block body portion with material relieved from both the top surface 348 and bottom surface 346 to allow easy access and gripping. The block body 344 may be made from an inert material, such as Teflon®, Delrin® or the like and may have a width of about 0.4 inches to about 3 inches, more specifically, about 0.8 inches to about 1.2 inches, a length of about 0.5 inches to about 4 inches, more specifically, about 1.5 inches to about 2.5 inches, and a height or thickness of about 0.2 inches to about 1.5 inches, more specifically, about 0.3 inches to about 0.7 inches.

FIGS. 21A-21D illustrate an embodiment of a pin tool displacement block 360 for use with a 6×4 pin tool array. The pin tool displacement block 360 includes 6 parallel slots 362 that may have a regular spacing that is configured to match that of an array of pin tools of a pin tool head assembly 64. Two relieved channels 364 are disposed in each of a second parallel slot, a fourth parallel slot, and a sixth parallel slot in order to allow six pin tools to be configured for use after deployment of the pin tool displacement block into the pin too head assembly. Other than the 6 relieved channels 364, the pin tool displacement block of FIGS. 21A-21D may have the same features, dimensions or materials as those of the pin tool displacement block of FIGS. 20A-20D discussed above. The relieved channels of the pin tool displacement block are disposed at the 2-2, 2-4, 4-2, 4-4, 6-2 and 6-4 positions of the array and extend completely through the block body portion of the pin tool displacement block 360.

For some embodiments, a method for selectively displacing at least one pin tool 68 of a pin tool head assembly 64 of a robotic sample transfer device 10 may include the use of a pin tool displacement block 370 having a block body with a bottom surface and a plurality of parallel slots formed into the block body portion. The parallel slots may be substantially perpendicular to the bottom surface with a predetermined regular spacing configured to correspond to regular spacing of pin tools 68 of a pin tool head assembly 64. The parallel slots may have a transverse dimension sized to allow easy movement of a width of a nominal shaft of the pin tools 68 in the slots but restrictive of movement of an enlarged portion of the shaft of the pin tools. The pin tool displacement block may also include at least one relieved portion or channel in a slot which has a transverse dimension sized to allow easy downward movement of the enlarged portion of a pin tool shaft which is greater than the transverse dimension of the slot and which extends from a top surface of the block body towards the bottom surface. An array of pin tools of a pin tool head assembly 64 are axially displaced by depressing the distal ends of the pin tools 68 against a flat surface. The pin tool displacement block may then be deployed into the pin tool head assembly such that the parallel slots of the pin tool displacement block slide over rows of the array of pin tools of the pin tool head assembly. The pin tools 68 are then allowed to return to a relaxed state by retracting the pin tool head assembly from the flat surface with at least one of the pin tools remaining displaced in an axially retracted and relaxed state.

Figure 22:
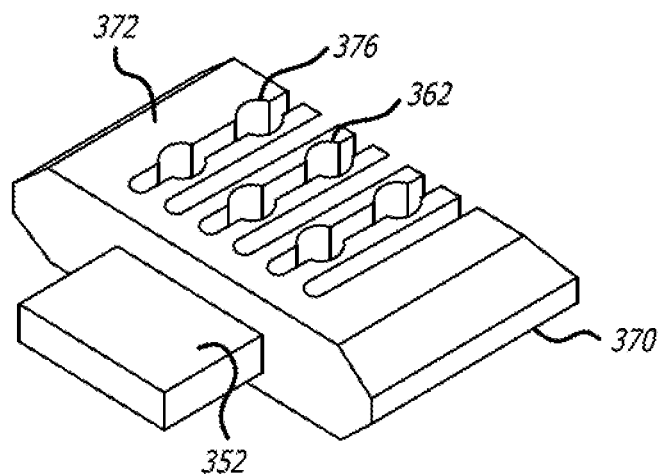
FIG. 22 is a perspective view from a first side of a reversible pin tool displacement block embodiment.
Figure 23:
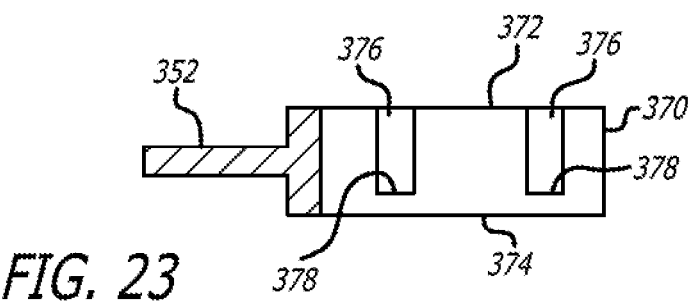
FIG. 23 is an elevation view of the reversible pin tool displacement block of FIG. 22.
Figure 24:
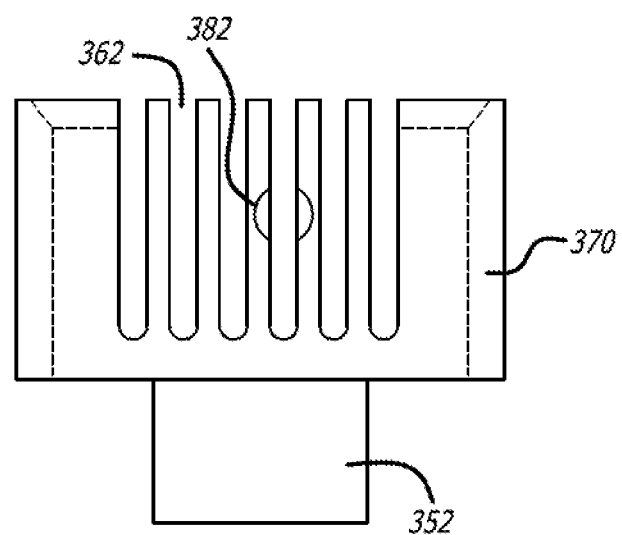
FIG. 24 is a view from a second side of the reversible pin tool displacement block of FIG. 22.

FIGS. 22-24 illustrate an embodiment of a reversible pin tool displacement block 370. The reversible pin tool displacement block 370 may have some or all of the features, dimensions or materials as those of the pin tool displacement block embodiments 300, 336 and 360, discussed above. The reversible pin tool displacement block 370 essentially combines the functions of the pin tool displacement blocks 336 and 360 of FIGS. 20A-20D and FIGS. 21A-21D discussed above. When the block 370 is oriented in a first direction and deployed, a first pin tool or set of pin tools is active and when the block is flipped over 180 degrees or otherwise oriented a second direction and deployed, a second pin tool or set of pin tools is active which is different from the first set. The reversible pin tool displacement block embodiment 370 shown allows a single pin tool to be configured for used while deployed on a first side 372 while maintaining all remaining pin tools of a 6×4 pin tool array in a retracted state. The reversible pin tool displacement block 370 allows 6 pin tools to be configured for used while deployed on a second side 374 while maintaining all remaining pin tools of a 6×4 pin tool array in a retracted state.

For the reversible pin tool displacement block embodiment 370, it may be desirable for relieved portion or portions 376 to extend only partially through the block body portion 370 and terminate at a stop surface 378 which is spaced from a surface of the block opposite the opening of the relieved channel 376. The first surface 372 and second surface 374 of the block body 370 portion may be substantially flat and substantially parallel to each other for some embodiments. FIG. 22 illustrates the pin tool displacement block 370 with the first side 372 up showing 6 relieved channels 380 that allow six pin tools 68 to be active or usable when the pin tool block 370 is deployed on the second side 374 with the second side down. FIG. 24 illustrates the pin tool displacement block 370 with second side 374 up showing a single relieved channel 382 that allow a single pin tool to be active or usable on the first side when the first side is down.

Some method embodiments of dispensing calibration material onto a chip 274, such as a spectrometry chip, may include the use of a chip 274 having an array of regularly spaced sample deposition sites 292 disposed on a substantially flat working surface 293 of the chip 274. The chip 274 may also include at least one sample deposition site 292 for receiving calibration material which is also disposed on the flat working surface 293 of the chip 274. The method embodiments may include the use of a robotic sample transfer device 10 having a pin tool head assembly 64 with an array of regularly spaced pin tools 68. Distal ends 158 of the pin tools 68 of the pin tool head assembly 64 are disposed substantially coplanar in a relaxed state and have a regular spacing which is the same as or otherwise matched to the regular spacing of the first array of sample deposition sites 292 of the chip. The spacing of the pin tools 68 may also be an integer multiple of the spacing of the sample deposition sites of the chip 274 and configured to align with the array of regularly spaced sample deposition sites 292 of the chip 274 or a subset thereof.

Generally, it is desirable to dispense calibration material very selectively to only those sample deposition sites 292 that are intended for use with calibration materials. As such, it is desirable to avoid dispensing calibration material or otherwise contaminating sample deposition sites 292 which are not intended for use in calibration with calibration material. For some method embodiments, it may be useful to use a reduced number of pin tools 68 of a pin tool head assembly 64 in order to avoid such contamination or inadvertent material transfer. For some such method embodiments, all but one of the pin tools 68 of the pin tool head assembly 64 is displaced to a retracted non-usable state by deploying a pin tool displacement block 336, such as pin tool displacement block shown in FIGS. 20A-20D, into the pin tool head assembly 64. The pin tool block 336 may be deployed in the pin tool head assembly 64 as shown in FIGS. 18 and 19 and discussed in the accompanying text above. A sample reservoir 156 of the usable pin tool 68 of the robotic sample transfer device 10 may then be loaded with calibration material by dipping the pin tool 68 into a well containing calibration material. The calibration material may then be dispensed from the usable pin tool 68 of the robotic sample transfer device 10 to a sample deposition site 292 for receiving calibration material. During the deposition of the calibration material to the sample deposition site 292, the functioning pin tool 68 containing the calibration material extends distally below the pin tools 68 that are held in a retracted state by the pin tool displacement block 336. As such, while the functioning pin tool tip 156 is moved distally into contact with the sample deposition site 292 for deposition of the calibration material, the pin tools 68 which are displaced by the pin tool displacement block 336 do not contact the chip.

In addition to dispensing calibration materials by methods that include controlling the number of active pin tools 68 of a pin tool array 64, calibration material may also be deposited on selected sample deposition sites 292 of a chip 274 or the like by using a full array of pin tools 68. The full array of pin tools 68 may be used with a chip 274 having a first array of regularly spaced sample deposition sites 292 disposed on a substantially flat working surface 293 of the chip 274. The chip 274 may also have at least one sample deposition site 292 for receiving calibration material which is also disposed on the flat working surface 293 of the chip 274 and which is off pitch with respect to the regular spacing of the first array of regularly spaced sample deposition sites 292 of the chip 274, as shown in FIGS. 11A and 11B.

A robotic sample transfer device 10 having a pin tool head assembly 64 may also be used for the calibration method. The pin tool head assembly 64 may have an array of regularly spaced pin tools 68 with distal ends 158 which are substantially coplanar with each other in a relaxed state. The pin tools 68 of the pin tool array also have a regular spacing which is the same as or otherwise corresponds to the regular spacing of the first array of sample deposition sites 292 or an integer multiple thereof. The regular spacing of the pin tools 68 is also configured to align with the array of regularly spaced sample deposition sites 292 of the chip 274 or a subset thereof.

Figure 25:
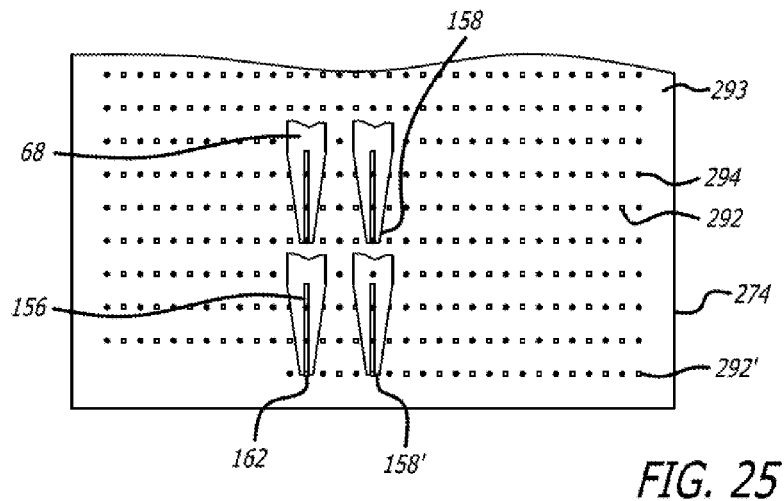
FIG. 25 is an enlarged perspective view of a portion of a sample chip showing sample deposition sites and sample reservoirs of a pin tool head assembly disposed over calibration sites.

During a calibration process embodiment, sample reservoirs 156 of the array of regularly spaced pin tools 68 of the robotic sample transfer device 10 may be loaded with calibration material. Only the pin tool reservoir or reservoirs 156 that will be depositing the calibration material onto the desired calibration material sample deposition site will be loaded with calibration material for some embodiments. The calibration material may then be dispensed from the pin tools 68 of the robotic sample transfer device 10 to the at least one sample deposition site 292 for receiving calibration material. During deposition of the calibration material, the pin tools 68 which are not aligned with sample deposition sites 292 for receiving calibration material are off pitch with respect to the first array of regularly spaced sample deposition sites 292 of the chip. As such, the pin tools 68 do not contact any of the regularly spaced sample deposition sites 292 of the first array. FIG. 25 illustrates two pin tool distal ends 158 disposed over sample deposition sites 292 of a second array of sample deposition sites which are regularly spaced and off pitch from the first array. The sample deposition sites 292 of the second array are configured to receive calibration material which is being dispensed from the sample reservoirs 156 of the distal tips 158 of the pin tools 68 to the calibration sample deposition sites 292 of the chip 274 as shown. Also shown are two pin tool distal ends 158 disposed between and not aligned with the sample deposition sites of the first array of sample deposition sites 292 for receiving normal sample deposition. For some embodiments, the first array of regularly spaced sample deposition sites includes an array of regularly spaced mass spectrometry sample deposition sites.

Figure 26:
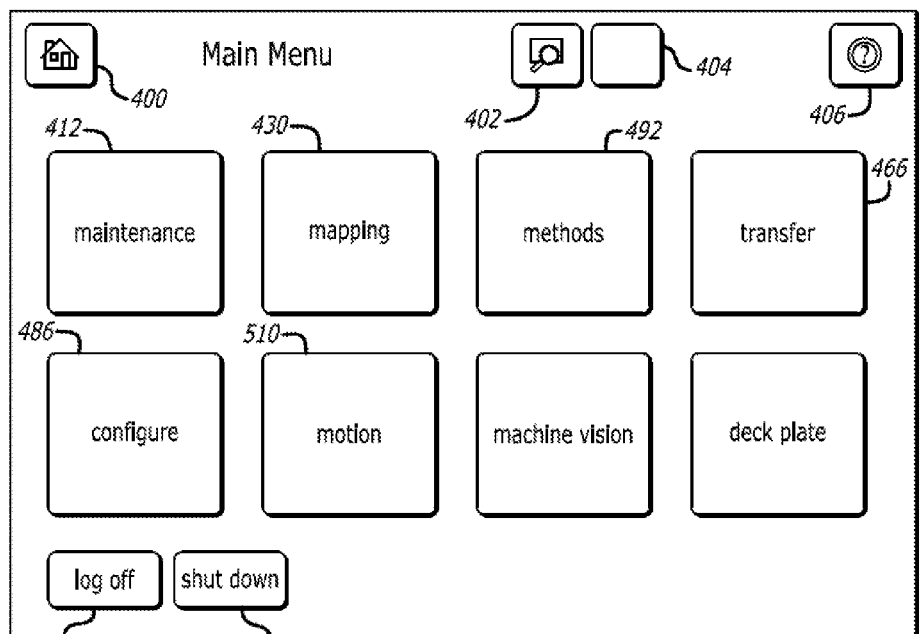

FIG. 26 illustrates a main screen of an embodiment of the user interface 26 discussed above. The main screen or main menu is arrived at after a user logs onto the device 10 by entering a user name and password into the system through the user interface 26. From the main screen of the user interface 26, a user may navigate the various programming controls of the device 10 in a convenient and user friendly manner. For the embodiment shown, along the top row of the screen, a "home" button 400 may be touched by the user to manually send the pin tool head assembly 64 of the device 10 to a home position located generally towards the front and left side of the processing chamber 14. A "system status" button 402 takes the user to a screen that provides detailed information regarding the current status of the integrated robotic positioning device 10. Status data such as the identification of the current user, computer identification, hard drive capacity, volatile memory capacity, software version, x, y, and z positions of the pin tool head assembly 64, safety interlock status, temperature and humidity within the processing chamber 14, wash fluid tank 242 and waste fluid tank 224 fluid levels as well as other information may be displayed on the status screen or screens. The "exit" button 404 takes the user back to the fundamental operating system interface of the processor 32. For example, for processor embodiments 32 using a Windows® type operating system, the exit button 404 will return the user back to a Windows® desktop. A "help" button 406 allows the user to access a help database with information regarding the programming, use and operation of the device 10 with regard to the type of options available on the screen displaying the help button 406. Generally, for some embodiments, each screen of the user interface 26 may have a help button 406. At the bottom row of the main screen, a "log off" button 408 is used to log off the current logged on user of the system 10. A "shut down" button 410 shuts down the system 10.

Figure 27:
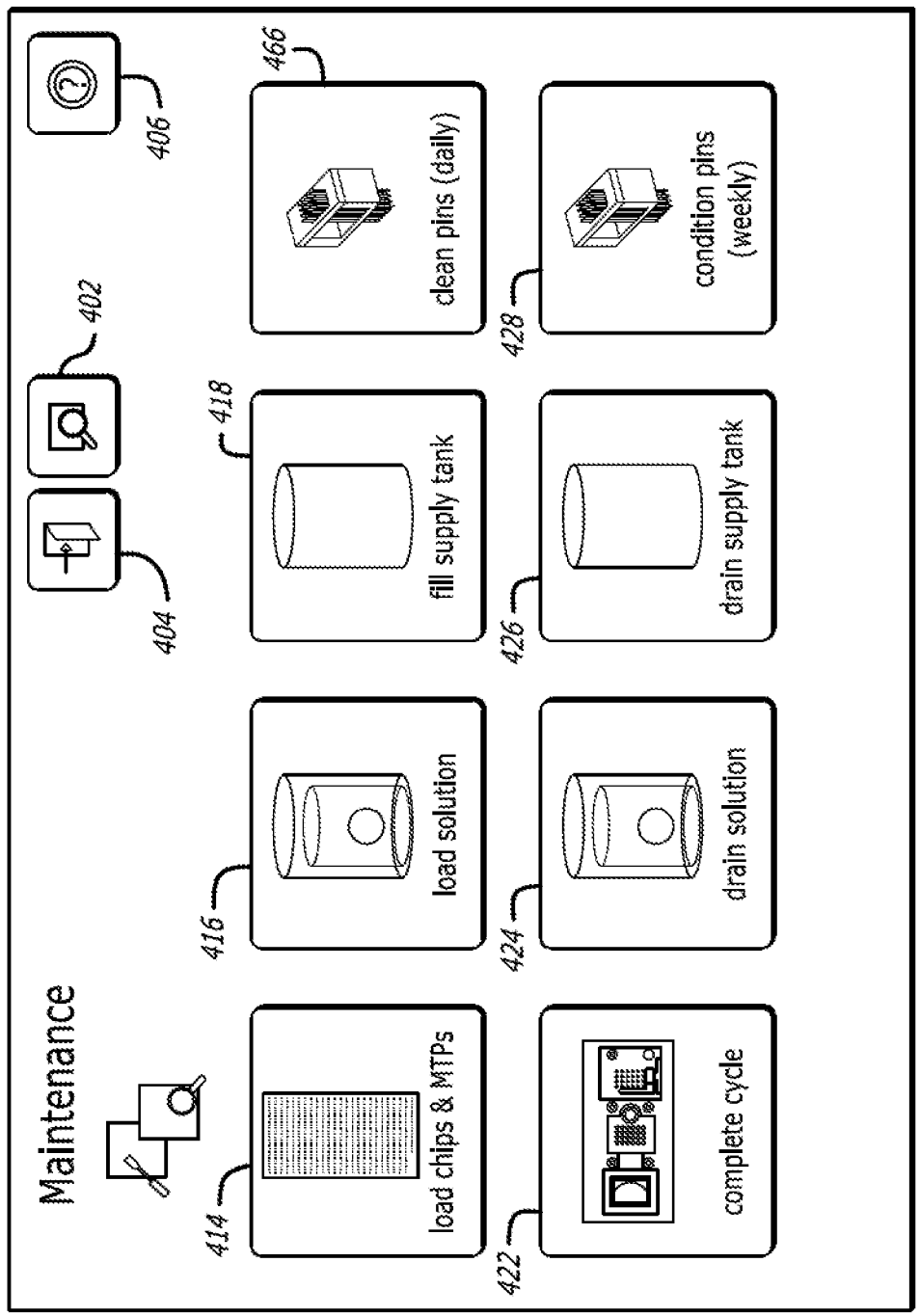

A "maintenance" button 412 on the main screen takes a logged on user to a maintenance screen illustrated in FIG. 27. The maintenance screen includes the status button 402, exit button 404 and help button 406 discussed above. The maintenance screen also includes a "load chips and MTPs" button 414, a "load solution" button 416, a "fill supply tank" button 418, a "clean pins" button 420, a "complete cycle" button 422, a "drain solution" button 424, an "drain supply tank" button, 426 and a "condition pins" button 428. The load chips and MTPs button 414 moves the pin tool head assembly 64 of the system 10 to a far left and rear position in order to make room for the user to load sample chips 274 or a chip block 266 onto the work surface 22 of the device 10. The load solution button 416 moves the pin tool head assembly 64 to the far right and rear position of the processing chamber 14 in order to make room for a user to load or unload the supply reservoir 168. The fill supply tank button 418 prompts the user to position the fluid valves in the lower storage tank chamber 44 in communication with the supply tank such that the supply tank 242 may be filled from an external tank. After the user is prompted to manually configure the valves, de-ionized water may be pumped into the supply tank with a self priming pump disposed within the housing 12. The pump may be configured to automatically turn off once the tank 242 is filled. The user may then be prompted to switch the valves manually back normal operating mode. The controller may then execute a priming routine to clean out air from the tubing or lines between the tank 242 and the rinse station. To accomplish this, the water may be pumped to the rinse station at about 5 percent to about 10 percent normal flow using a pulsed modulation technique. For this pulsed technique, the pump may be run at full speed for a short period of time and then stopped for an interval before restarting again. For some embodiments, the pump may be run for about 5 msec to about 15 msec and stopped for about 85 msec to about 95 msec. The pulse intervals are short enough that the pump appears to run continuously to the user, but is only achieving a 5 percent to 10 percent duty cycle.

The clean pins button 420 runs a protocol for cleaning the pins 68 of the pin tool head assembly 64 by immersing the pins in the ultrasonic bath for an extended period of time. For some embodiments, the pin tools 64 may be soaked for about 15 minutes to about 45 minutes, more specifically, for about 25 minutes to about 35 minutes. During the soaking process, the ultrasonic bath may contain a cleaning solution such as pure ethanol. The pin tools may be treated with a subsequent standard cleaning cycle after the soak that may include a water rinse in the rinse station, drying in the vacuum drying station, ultrasonic cleaning with water in the ultrasonic bath and a final drying in the vacuum drying station.

A complete cycle button 422 initiates a standard cleaning cycle, as discussed above, including a water rinse in the rinse station, drying in the vacuum drying station, ultrasonic cleaning with water and alcohol in the ultrasonic bath and a final drying in the vacuum drying station. For some embodiments, an equal mix of de-ionized water and ethanol alcohol may be used for the ultrasonic cleaning bath. The drain solution button 424 turns on the pump 222 and drains the ultrasonic bath of the ultrasonic wash station. As the ultrasonic bath is drained, it may be refilled by the reservoir 168 until the reservoir is emptied.

The drain supply tank button 426 turns on the rinse fluid pump continuously until the rinse fluid supply tank 242 is emptied. This may be used to lighten the device 10 in anticipation of transporting the device 10, performing maintenance in the lower chamber or the like. The condition pins button 428 initiates a protocol whereby the pins 68 of the pin tool head assembly 64 are soaked in a cleaning solution, such as a 1 molar solution of NaOH which may be disposed within selected wells of a microtiter plate. The pins 68 may be soaked for about 5 minutes to about 15 minutes and then treated with a standard clean cycle as discussed above. This process may be carried out every week or so in order to condition the pins 68.

Figure 28:
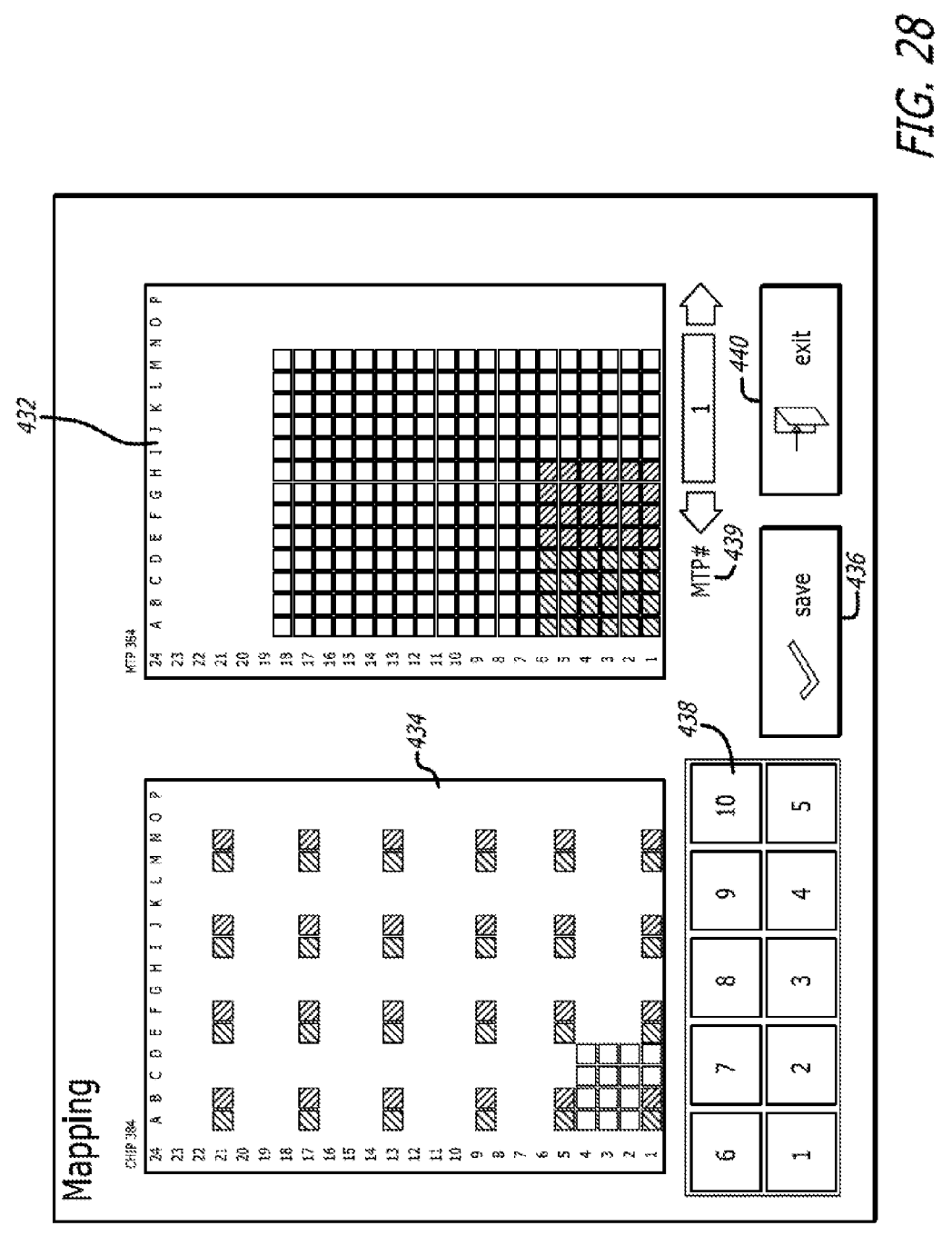

Referring back to FIG. 26, a "mapping" button 430 takes the user to a mapping screen shown in FIG. 28. The mapping screen allows the user to input some preliminary information about the sample transfer process desired. For example, for some embodiments, the user may be prompted with a request to select a microtiter plate format, such as a 96 or 384 well plate. Next, the user may be prompted to select a chip format and thereafter the number of the chips to be used. Once this information has been entered, mapping information presented visually by a grid 432 representing the microtiter plate wells and grid 434, representing the chip sample deposition sites, may be selected and stored by a "save" button 436 to track the mapping to be used. Chip buttons 438 may be used to select the chip number to be loaded with samples taken and the "MTP" arrow buttons 439 may be used to select the microtiter plate from which to load samples. The "exit" button 440 may be used to exit the mapping screen. In addition, a two dimensional bar code of a selected chip 274 may be tied to a bar code of a specific microtiter plate by the controller. The controller may also store the mapping configuration selected between the chip and microtiter plate along with some additional data including time stamp data, microtiter plate and chip configuration data and the like. All of this data may be transferred to a sample tracking database server or other data storage device.

Figure 29:
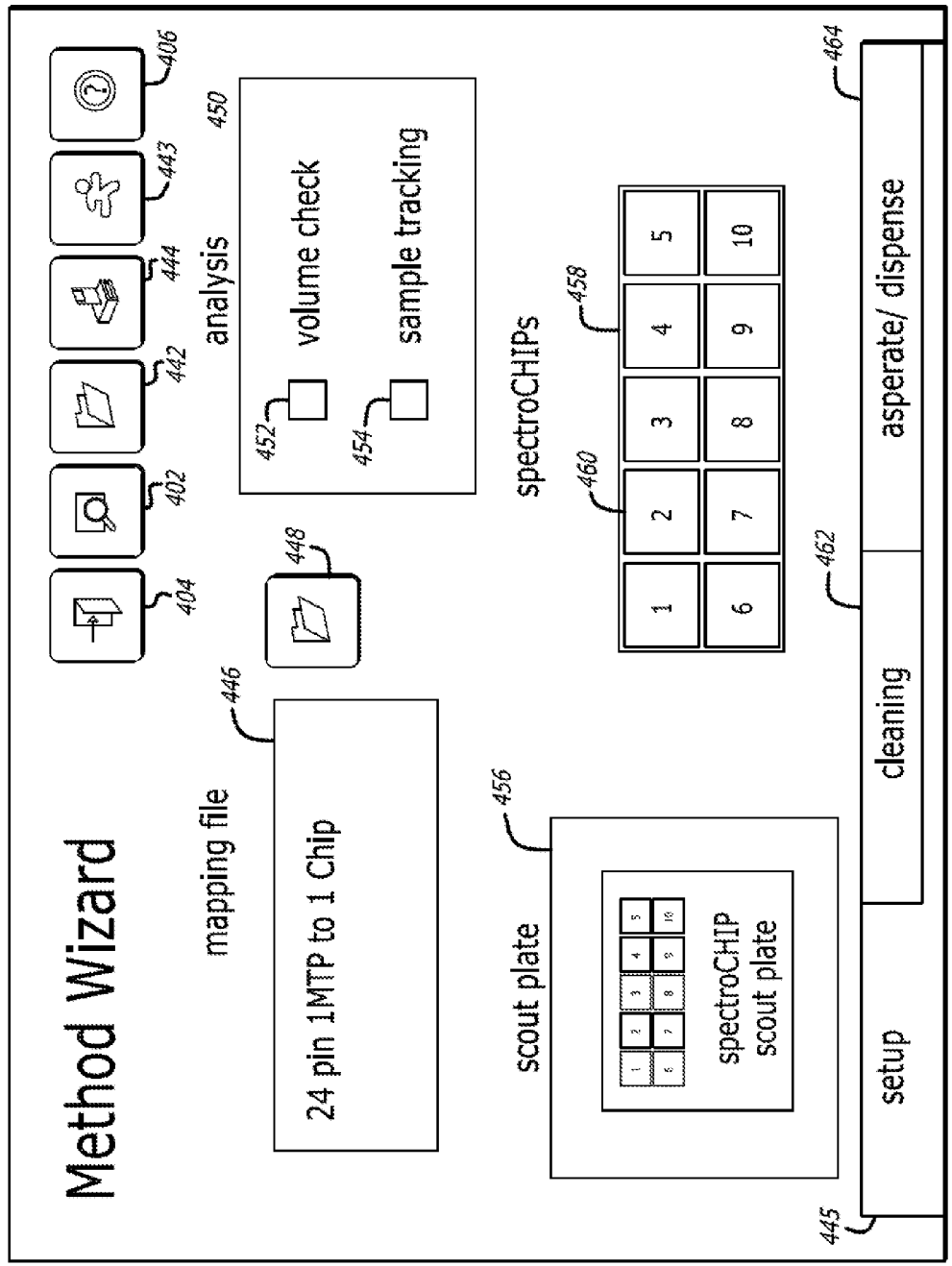

Referring again to FIG. 26, a "methods" button 442 takes the user to a methods screen shown in FIG. 29. The methods screen includes the exit button 404, status button 402 and help button 406 on the top row which may have the same functions as discussed above. Also on the top row of the methods screen are an "open" button 442 and a "save" button 444. The open button 442 allows a user to open a predetermined set of method transfer parameters and the save button 444 allows a user to save a predetermined set of method transfer parameters. A "run transfer" button 443 takes the user to the "run transfer" screen shown in FIG. 30 and discussed below. At the bottom of the methods screen are three tabs, with the "setup" tab 445 being selected for the methods screen embodiment shown. Within a "mapping file" section 446 of the methods screen for setup, a user may select a predetermined mapping file as generated from the mapping screen of FIG. 28 for use in a transfer method. A "browse" button 448 may be used to browse a plurality of predetermined mapping files created by a user. An "analysis" section 450 of the methods screen includes a "volume check" check box 452 and a "sample tracking" check box 454. If the user selects the volume check box 452, each sample deposited onto a sample deposition site of a chip 274 may be imaged by the imaging camera and the image taken processed in order to estimate the volume of each sample deposited onto a sample deposition site. The volume check parameters of a deposited sample may be determined by the volume, average diameter, y-axis direction diameter, x-axis direction diameter, circumference and area of one or more deposited samples. The average volume for samples deposited and standard deviation of volume of samples deposited may also be determined. If the sample tracking box is checked by a user, bar code data associated with microtiter plates 268 and corresponding chips 274 will be saved to a file that may be later accessed by a user in order to confirm a transfer method.

A "scout plate" section 456 allows a user to select a particular chip type from the number of chips such as a 4 chip scout plate or a 10 chip scout plate. A "spectrochips" section 458 includes "chip selection" buttons 460 numbered 1-10 for a 10 chip mount block (or 1-4 if a 4 chip mount block was selected in section 456) which allows a user to select a particular chip from the number of chips of the chip mount block type previously selected to receive transferred samples for a particular method.

Referring again to the bottom of the methods screen, if the "cleaning" tab 462 is selected for the screen, additional sections (not shown) are available to the user which allow a user to set cleaning cycle parameters such as dwell time in a particular cleaning station functional element and the like. The "aspirate/dispense" tab 464 provides options on a screen (not shown) for the amount of time that the sample reservoir of the pin tools 68 dwell in a sample reservoir while aspirating a sample, the depth to which a pin tool 68 is moved into a sample well of a microtiter plate and the speed of the pin tool 68 as it enters and leaves a sample well of a microtiter plate. The user may also set the dwell time of a pin tool 68 as it contacts a sample deposition site of a chip, the speed of the pin tool as it approaches a surface of the chip and the length of compression of the resilient member which biases the pin tool 68 against the upper surface of the chip once the tip of the pin tool 68 makes contact. These parameters may affect the amount of sample aspirated or taken up by a pin tool 68 and the amount of sample deposited to a sample deposition site. These parameters may also affect the speed and efficiency of the transfer method and prevent damage to the chips 274 or microtiter plates as well as prevent loss of samples or contamination due to splashing as a result of excessive speed of the pin tool 68 during a transfer.

Figure 30:
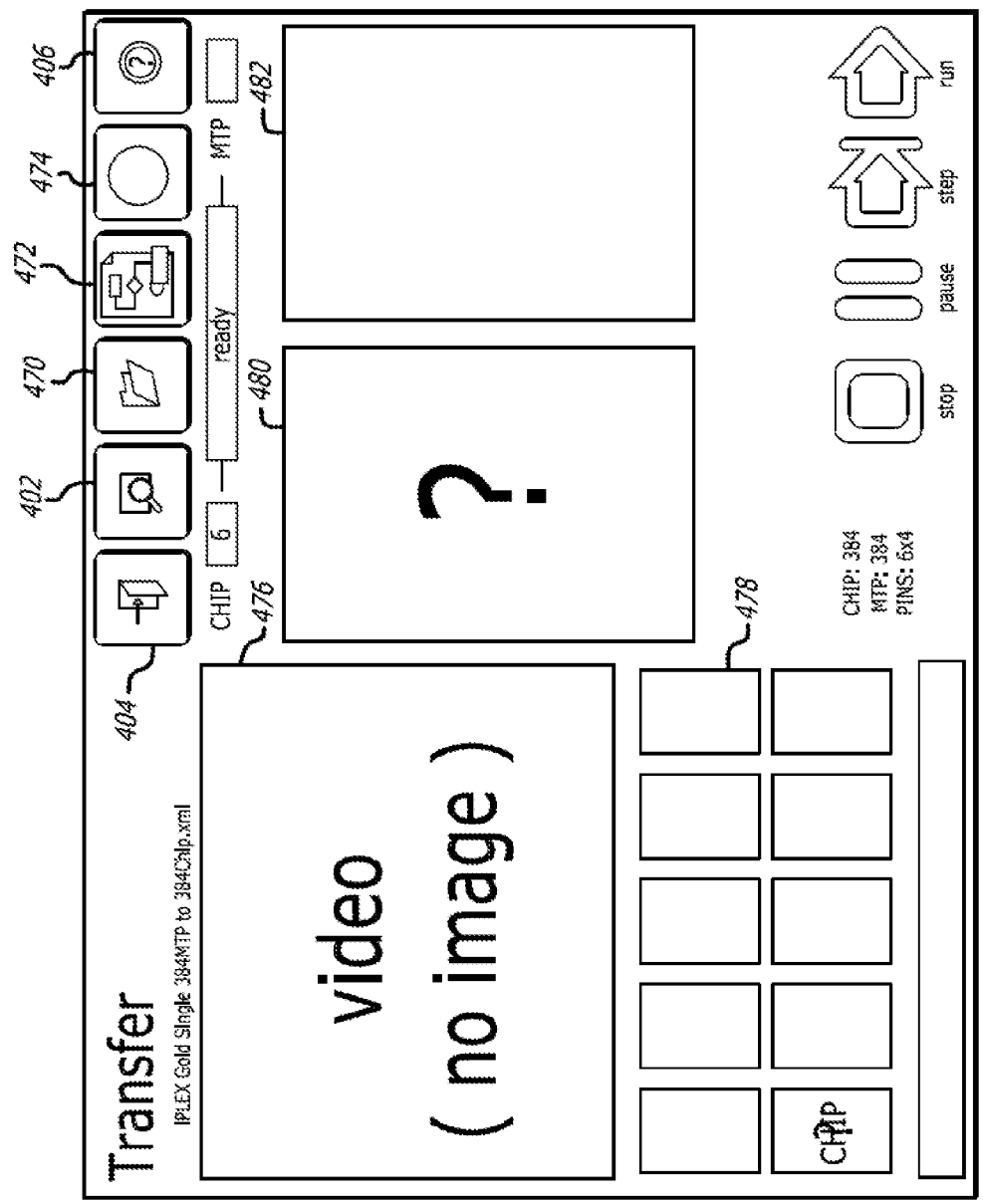

Referring again to FIG. 26, a "transfer" button 466 takes the user to a run transfer screen shown in FIG. 30. A top row on the run transfer screen again includes the exit button 404, status button 402, and help button 406 that may have the same functions as discussed above. An "open method" button 470 at the top of the screen allows a user to open a previously determined set of method parameters. A "flow" button 472 allows a user to access the method screen while running a transfer and change method parameters during the transfer process. A "volume check" button 474 allows a user to access and review volume check data for data collected when the volume check box 452 on the method screen is selected.

A live video image of the transfer process may be displayed in video block 476 as well as a graphic of the transfer status of sample deposition on chips 274 of a selected chip mount block shown on a chip status block 478. Microtiter plate status blocks 480 and 482 show the transfer status of two selected microtiter plates 268 in current use including a graphic display of sample wells that have already been transferred and which wells are full and have not yet been transferred to a sample deposition site of a chip 274. "Stop", "pause", "step" and "run" buttons are disposed at the bottom of the run transfer screen which allow a user to stop, pause or run a selected transfer process. The step button may pause after every dispense cycle to allow the user to update method parameters or view volume check data. The use may then press the step button again to continue the cycle in the transfer or press the run button to finish the transfer process without automatically pausing after each dispense cycle.

Figure 31:
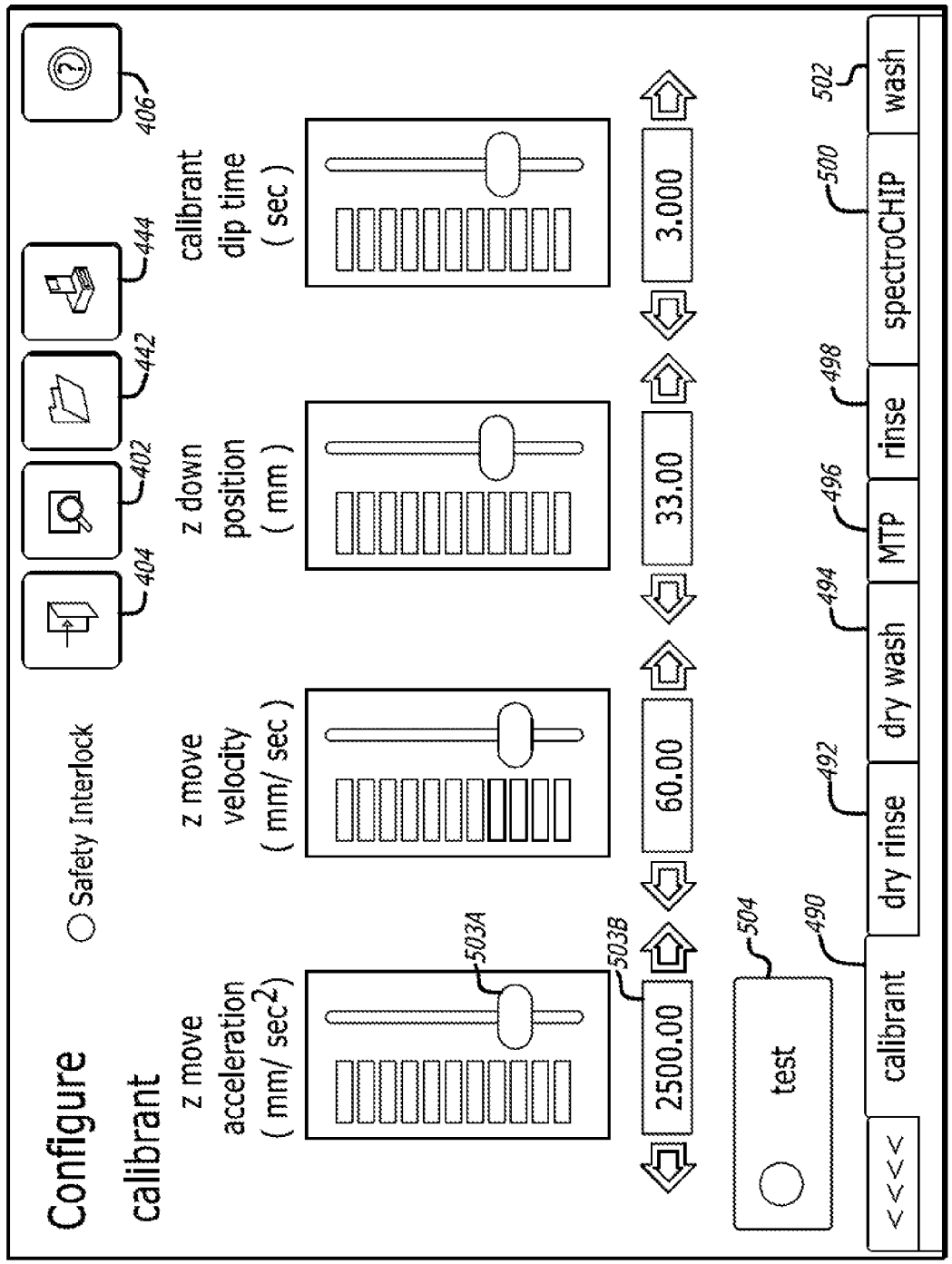

Referring back to FIG. 26, a "configure" button 486 takes the user to a configure screen shown in FIG. 31. A top row on the configure screen again includes the exit button 404, status button 402, and help button 406 that may have the same functions as discussed above. Also on the top row of the configure screen are an "open" button 442 and a "save" button 444. The open button 442 allows a user to open a predetermined set of method transfer parameters and the save button 444 allows a user to save a predetermined set of method transfer parameters.

At the bottom of the configure screen, a row of tabs allows the user to select sub-screens that provide options for selecting movement parameters for various predetermined process steps that the device 10 may carry out. The tabs at the bottom of the configure screen include a "calibrant" tab 490, a "dry rinse" tab 492, a "dry wash" tab 494, a "MTP" or microtiter plate tab 496, a "rinse" tab 498, a "spectochip" tab 500 and a "wash" tab 502. A tab with a set of laterally oriented arrows may be selected to show additional tabs (not shown) including a "general" tab, a "bar code" tab and a "calibration" tab. For each of these tabs, generally, motion parameters for the pin tool head assembly for the process corresponding to each tab may be selected or preset. For example, for the configure screen show in which the calibrant tab 490 is selected, the z axis motion acceleration, z axis motion velocity, z down position and calibrant dip time may be preset and saved. These settings may be determined by moving a sliding setting bar 503A disposed in a setting box or by directly entering numerical data in a data box 503B disposed below the sliding setting bar. Once these settings are selected and saved, they may be tested for each process indicated by the tabs by actuating the "test" button 504. Some additional features include functions of the barcode tab which allow a user to turn the bar code reader function on and off. The bar code reader function may be carried out by the bar code reader head for scanning linear bar codes on microtiter plates 268 as well as the imaging camera which may be used to scan two dimensional bar codes disposed on the chips 274.

The general tab screen has a variety of settings and also includes a button which allows a user to reset all of the settings of the configure screens to the factory default settings. The calibration tab screen provides the user with predetermined settings that may not be changed often. For example, the calibration tab screen may provide a data box to enter the position offset of a pre-selected pin tool 68 of the pin tool head assembly 64, such as pin tool "A-1", with respect to the position of the center of the field of view of the imaging camera. Once this is properly set, any feature, functional element or the like which is imaged by the imaging camera in the center of the field of view may then be accessed by a pin tool by instructing the processor to move the pin tool 68 in the distance and direction of the known offset, which may serve as a single entry look up table for such motion.

Figure 32:
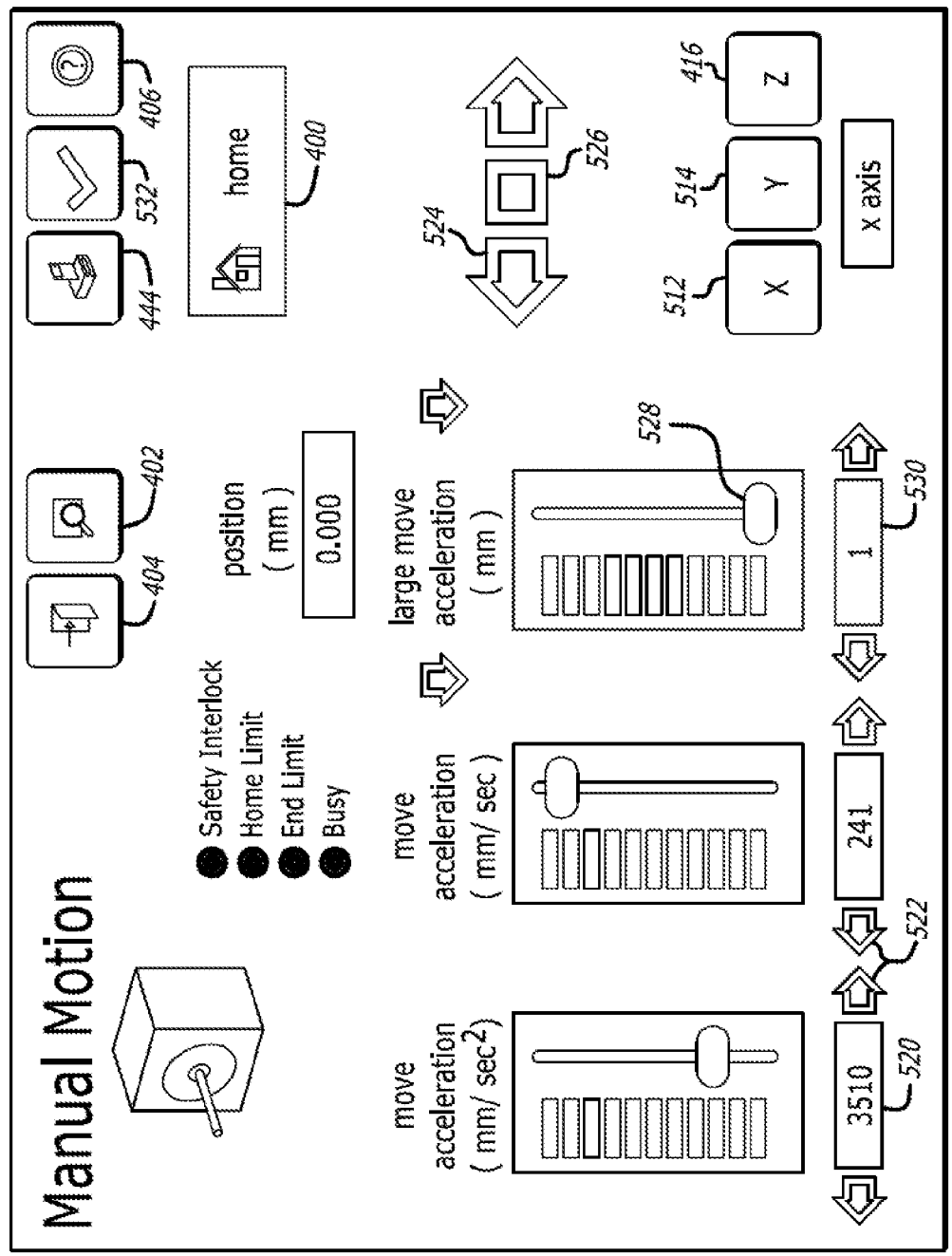

Referring to FIG. 26, a "motion" button 510 takes the user to a motion screen shown in FIG. 32. A top row on the motion screen again includes the exit button 404, status button 402, and help button 406 that may have the same functions as discussed above. Also on the top row of the configure screen is a "save" button 444 that may be used to store settings. A home button 400 is also disposed on the motion screen to have the pin tool head assembly moved to the home position.

The motion screen of FIG. 32 allows a user to select general motion parameters for motion acceleration, velocity and large move distance for translation of the pin tool head assembly in the x, y and z axes, with the buttons for selecting the axis of interest indicated by buttons 512, 514 and 516 respectively. Data selections for these parameters may be entered by clicking and moving a sliding bar 518 or by direct data entry into a data box 520 disposed below the sliding bar 518. Arrows 522 disposed on either side of the data boxes allow a user to click the arrows and adjust the parameters in the data boxes by fixed increments. A set of arrows 524 are disposed on the right hand side of the screen and allow a user to manually move or jog the pin tool head assembly by predetermined increments. A toggle button 526 allows users to select between large movement increments and small movement increments, each of the increments being selected or set by the sliding bar 528 or by direct data entry into data box 530. One of the uses of the functions on the motion screen is to teach the processor of the device 10 where the locations of the various components or functional elements reside on the work surface. For example, a user may wish to teach the processor the location of a first microtiter plate disposed on the microtiter plate mount block of the work surface. The user may use the jog buttons 524 in either large movement or small movement mode to position the pin tool head array 64 above the predetermined corner of the first microtiter plate. Fine adjustments may be made with visual feedback by the user to align the pin tools 68 with the predetermined wells of the microtiter plate.

Figure 33:
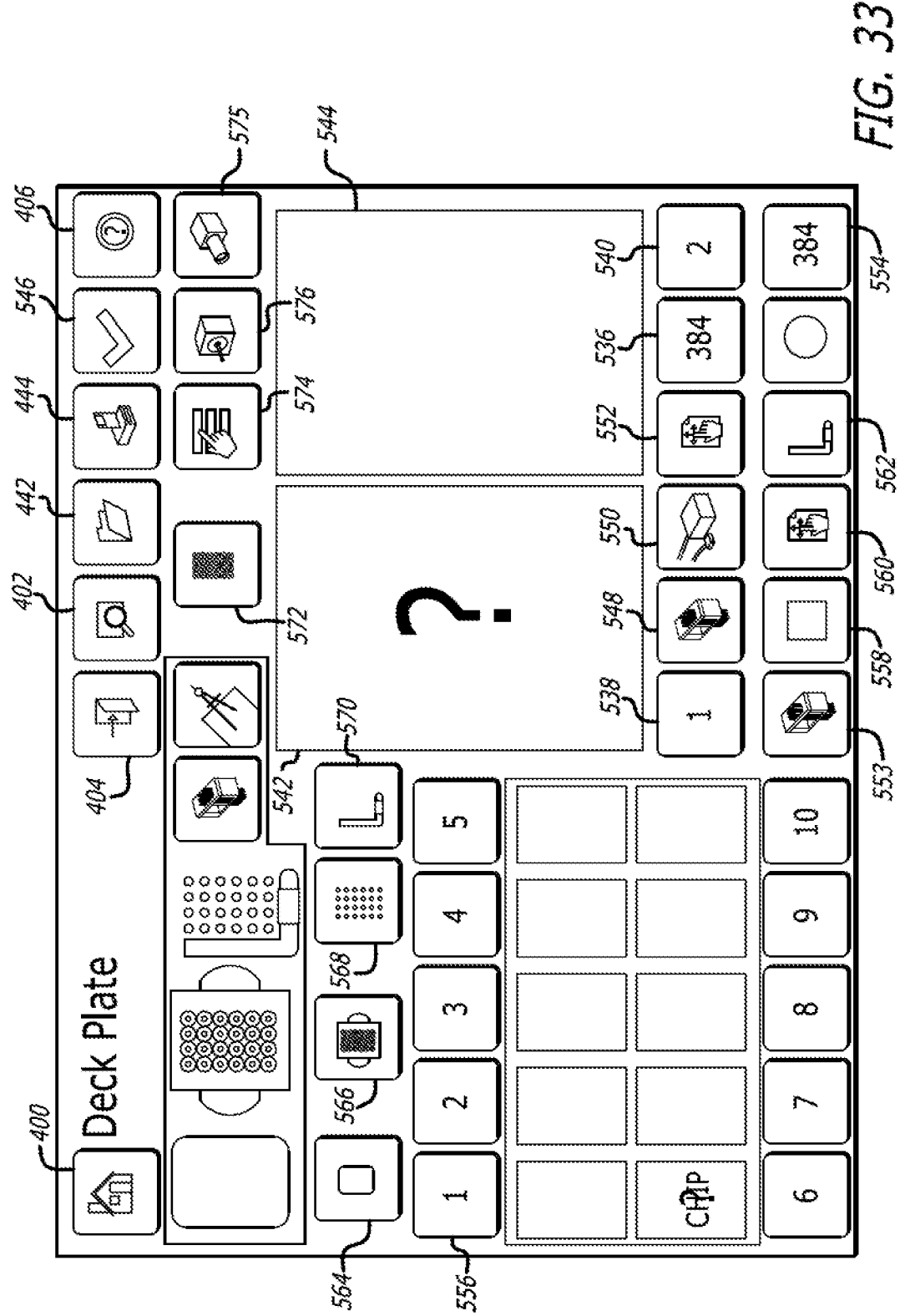

Once this positioning has been achieved, the user may select a "check" button 532 disposed at the top of the motion screen which then takes the user to the "deck plate" screen shown in FIG. 33. A top row on the deck plate screen includes the exit button 404, status button 402, and help button 406 that may have the same functions as discussed above. Also on the top row of the deck plate screen are an "open" button 442 and a "save" button 444. The open button 442 allows a user to open a predetermined set of method transfer parameters and the save button 444 allows a user to save a predetermined set of method transfer parameters.

The deck plate screen also includes a variety of buttons that may be used to allow a user to store position data generated from the position sensors such as the encoder strip assemblies and store that known position data so as to associate the position data to a known component of functional element of the work surface. There are two basic approaches to use of the deck plate screen. The first is a manual teach mode which may be entered from the check save button 532 of the motion screen wherein know position data is stored so as to correspond to know functional elements or components of the device 10. A manual mode in the deck plate screen allows a user to direct the pin tool head to a known, pre-programmed position and also allows the used to carry out basic single event procedures, such as washing, drying, rinsing etc.

If the position information for each of the functional elements of the work surface 22 is taught to the processor, a database or lookup type table may be generated for use as to absolute and relative positions of the functional elements as well as other components. For example, from the motion screen of FIG. 32, the pin tool head array may be moved by a user using the jog buttons 524 to the A-1 position of the first microtiter plate disposed on the work surface of the device. Once the pin tools are properly positioned, a "microtiter plate type" button 536 may be touched and toggled so as to select a microtiter plate type that matches the type mounted to the work surface. For some embodiments, the toggle choices may include a 96 well or 384 well microtiter plate. A "first microtiter plate" button 538 may then be touched to indicate that the pin tools 68 are disposed in the first microtiter plate and not the second microtiter plate which may be selected by "second microtiter plate" button 540. A graphic image of the first microtiter plate is displayed on block 542 and the second microtiter plate on block 544. If the position data and component selection has been properly made, the user may then select the "check save" button 546 at the top of the screen which saves the data to the memory storage unit of the controller 28 or other suitable device. This same procedure may be applied to the teaching of position data of the pin tool head assembly and pin tools 68 thereof by using the "pin tool" button 548, the bar code reader head assembly by using the "bar code reader" button 550, and the camera by using the "camera" button 552. These position data teaching procedures generally apply to the pin tool head assembly 64 and microtiter plates, however, the same or similar procedures for teaching position data to the controller 28 may also be used for the pin tool head assembly 64 with respect to the chips 274.

For such a procedure, the pin tool head may be manually moved to a predetermined location with respect to a chip 274 mounted in a chip mount block on the work surface. Such positioning may be carried out by using manual jogging movement from the position screen discussed above. Once the pin tools 68 are properly positioned with respect to a component for functional element, the component or functional element may be identified by touching the corresponding button, such as the "pin tool" button 553. Thereafter, the type of chip 274 being used may be selected by the "chip type" button 554 to select between a 384 site chip, a 96 site chip or any other suitable configuration. The specific chip 274 over which the pin tools 68 are located may then be selected by touching one of the "chip number" buttons 556 that correspond to the chip being used. If the position data and component selection has been properly made, the user may then select the "check save" button 546 at the top of the screen which saves the data to the memory storage unit of the controller 28 or other suitable device. This same procedure may be applied to the teaching of position data of the pin tool head assembly and pin tools 68 thereof, as well as the position of other components, by using other buttons on the screen. For example, position data for the 2-d bar code on a chip may be taught by using the "bar code reader" button 558, and the camera by using the "camera" button 560. The position data related to the calibration material vessel 256 may be taught by using the "calibration vessel" button 562.

Figure 34:
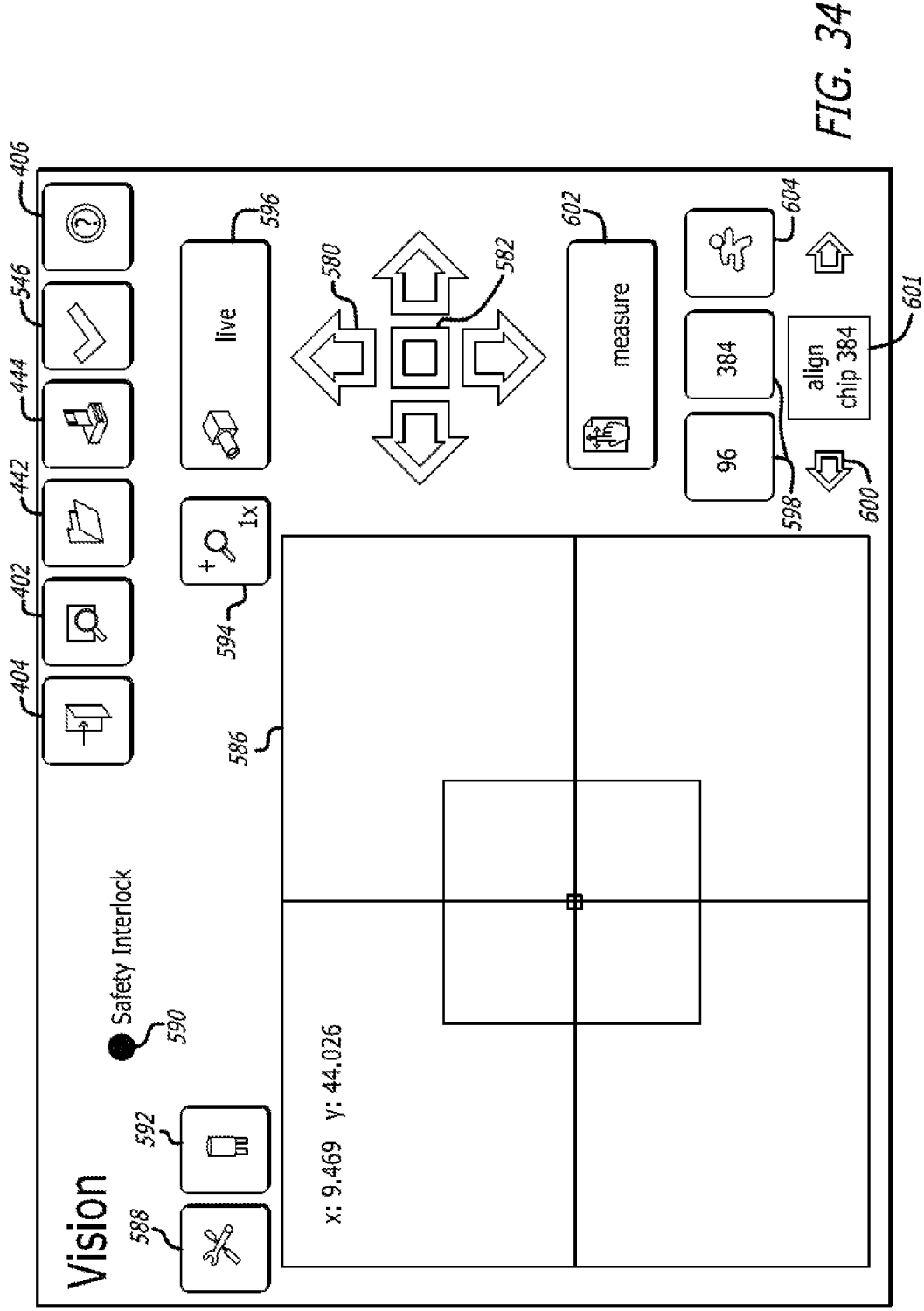
Figure 35A:
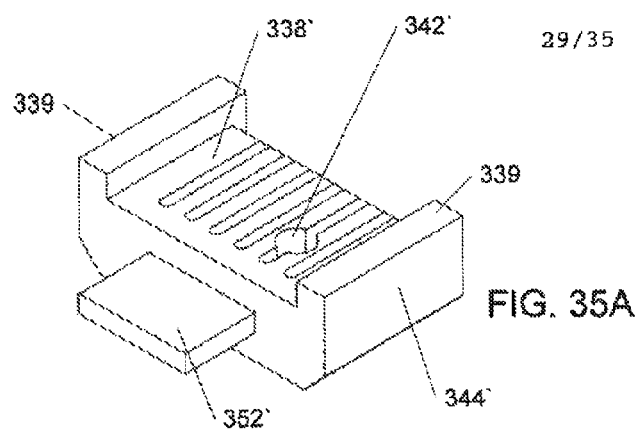
FIGS. 35A-35D illustrate an embodiment of a pin tool displacement block, single pin configuration.
Figure 35B:
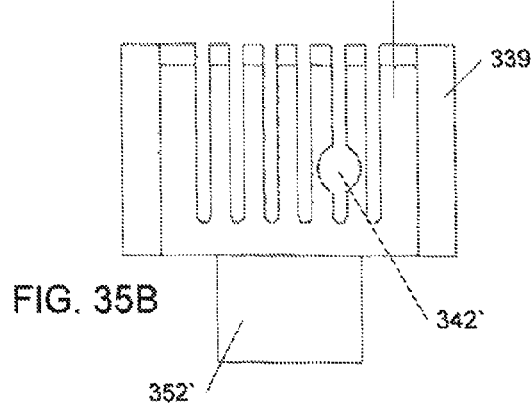
Figure 35C:
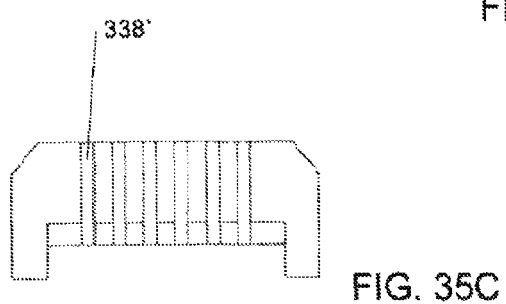
Figure 35D:
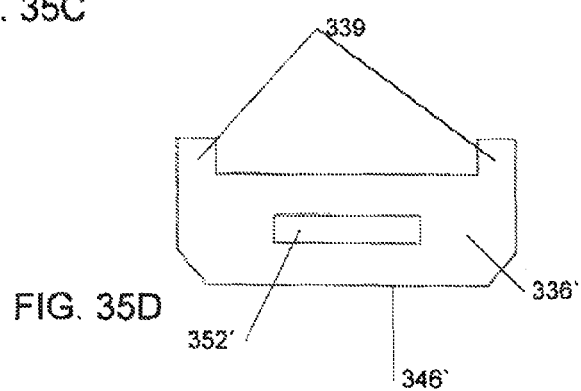
Figure 36A:
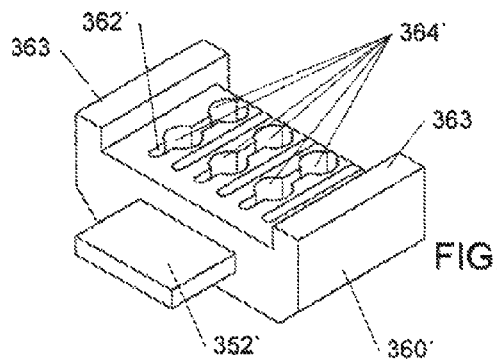
FIGS. 36A-36D illustrate an embodiment of a pin tool displacement block, six pin configuration.
Figure 36B:
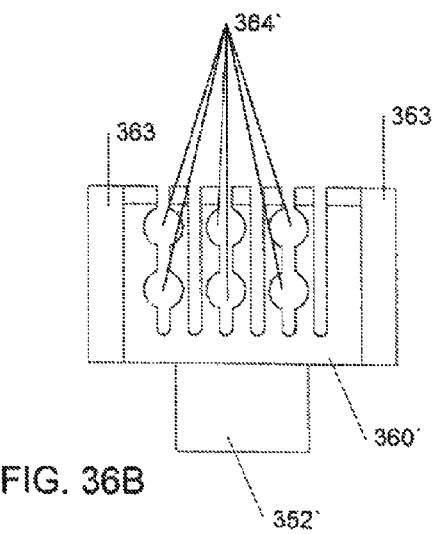
Figure 36C:
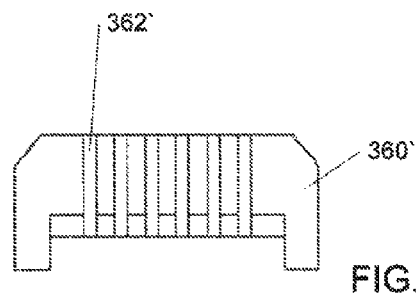
Figure 36D:
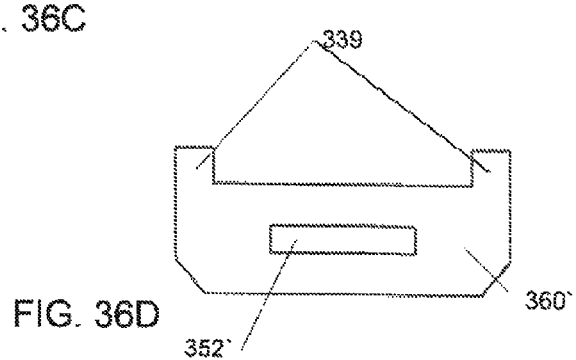

Once one or more position data sets have been taught to the controller 28, there are other features on the deck plate screen that allow a user to carry out basic functions on an as needed basis. For example, a user may initiate a wash cycle by touching "wash cycle" button 564, a rinse cycle by touching "rinse cycle" button 566 or a dry cycle by touching "dry cycle" button 568. A "calibration vessel home" button 570 may be used to move the pin tool head assembly 64 to the calibration vessel 256. A "pin tool selection" button 572 may be used to select or toggle between various pin tool array configurations, such as a single pin tool, 6 pin tool array or 24 pin tool array as well as others. A "configuration screen" button 574 may be touched by a user to jump to the configuration screen, a "motion screen" button 576 may be used to jump to the motion screen and a "vision screen" button 575 may be used to jump to the vision screen shown in FIG. 34.

The vision screen includes controls that allow a user to turn the imaging camera 132 on and off and move the camera to a desired position manually with a set of jog arrows 580 which may be toggled between large movement steps and small movement steps with a "toggle" button 582. The live video image block 584 allows the user to see the work surface 22 and functional elements and components thereof through the imaging camera lens while the camera is being positioned with the jog arrow buttons 580. The vision screen may also be used in conjunction with the deck plate screen for manual teaching of positions and relative positions of the pin tool head, bar code reader and imaging camera with respect to the work surface 22 and functional elements thereof. Work surface components may be viewed on the video image block 584 and aligned with a cross hair centering reticle 586 positioned in the center of the field of view of the imaging camera so that the position of the viewed and aligned component may be know with regard to the position of the imaging camera 132. If the position of the center of field of view of the imaging camera is know with respect to other components of the device 10, this positioning data may be stored or otherwise used to calculate the position of other components. If the imaging camera is aligned with a component at a position that is useful to be taught to the controller 28, the "check" button 532 may be selected to take the user to the deck plate screen discussed above for manual teaching of position as discussed above.

A top row on the vision screen includes the exit button 404, status button 402, and help button 406 that may have the same functions as discussed above. Also on the top row of the vision screen are an "open" button 442 and a "save" button 444. The open button 442 allows a user to open a predetermined set of method transfer parameters and the save button 444 allows a user to save a predetermined set of method transfer parameters. A "configuration" button 588 allows a user to set a variety of imaging parameters such as exposure, gain and further adjustment of jog movement parameters such as the length of the large and small movement jog steps. The safety interlock indicator 590 indicates whether the safety interlock switch is engaged or disengaged. An "illuminator" button 592 toggles an illumination light source for the imaging camera 132 on and off. A "zoom" button 594 zooms the field of view in the live image block 584 in and out and a "video on" button 596 toggles the imaging camera 132 on and off.

A set of "chip type" buttons 598 allows a user to select the type of chip 274 being imaged or otherwise used on the work surface 22. A selection may be made between a 96 site chip and a 384 site chip. A set of selection arrows 600 allow a user to choose from a menu of predetermined image processing algorithms 601 which may be used to confirm the position of the imaging camera relative to a feature or component of interest. Examples of the algorithms include a 2-d bar code algorithm, an align a 96 site chip algorithm, an align a 384 site chip algorithm, an align a 96 well microtiter plate algorithm, an align a 384 well microtiter plate algorithm, a calibrate pins algorithm, a calibrate pixels algorithm, and a volume check algorithm. The calibrate pins algorithm determines the center of the field of view of the imaging camera with respect to the position of a particular pin tool, such as the A1 positioned pin tool. The calibration of pixels algorithm uses the known distance between two fiducial marks on a chip 274 to calculate the number of pixels of the imaging camera per millimeter on the plane of the work surface. The "measure" button 602 may be used or selected in order to initiate a selected algorithm process once the camera has been positioned in a desired location. The "run" button 604 may be selected to move the pin tool head assembly, bar code reader or camera to a position on the work surface 22 corresponding to the algorithm selected to be run.

Figure 37A:
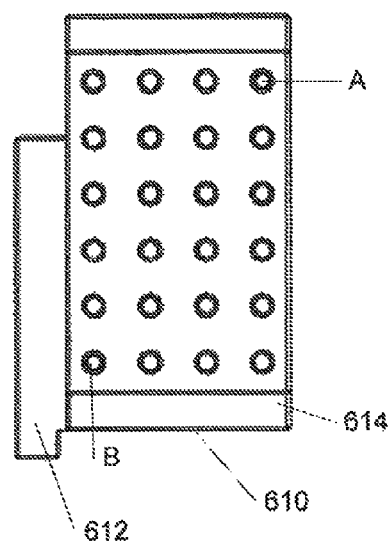
FIGS. 37A-37C illustrate an embodiment of a pin protection block tool assembly.
Figure 37B:
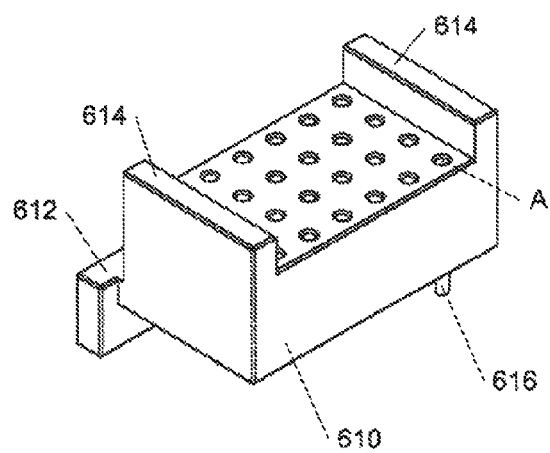
Figure 37C:
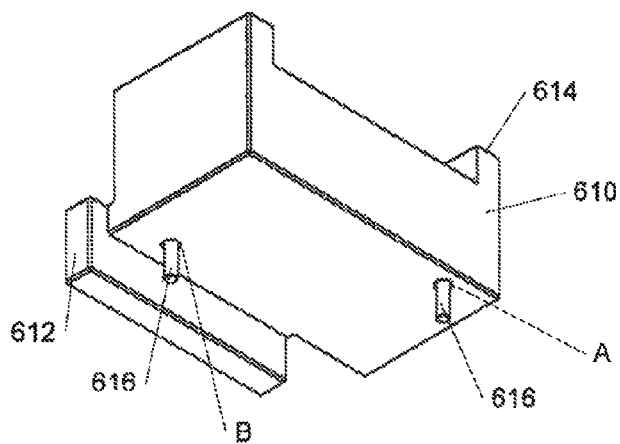

In addition to embodiments described above, other similar embodiments, such as those discussed below, may also be used in the same or similar manner as discussed above. For some embodiments, a pin protection block tool assembly for selectively displacing at least one pin tool 68 of a pin tool head assembly 64 of a robotic sample transfer device 10 may be used. Using the pin protection block tool allows the user to select any number of active pin tools by selective deactivation of the pin tools not being used in the standard 24 pin tool head 64. For instance, if the user wants only a single pin tool active, the user may use the pin protection block tool assembly in conjunction with a pin tool displacement block having a single pin configuration to selectively deactivate all but one of the pin tools 68 (e.g., deactivate 23 of 24). The pin protection block tool assembly, as shown in FIGS. 37A-37C, is used for upwards axial displacement of the pin tools 68 and pin tool collars 143 within the pin tool head assembly 64 prior to insertion of a pin tool displacement block. The pin protection block tool assembly has body 610 which is substantially rectangular in shape and has raised edges 614 which act as a hard stop to the downward movement of the lower surface, which in turn may prevent the user from over compressing the pins and damaging the pin array and holder, while allowing adequate room for inserting a pin tool displacement block (also referred to as a pin too displacement comb) of pin tool head assembly 64 of robotic sample transfer device 10. The pin protection block tool assembly has a top surface and a bottom surface which is substantially parallel to the top surface, and a plurality of non penetrating cylindrical bores machined into the block body, arranged with a predetermined regular spacing configured to correspond to regular spacing of pin tools 68 of a pin tool head assembly 64. At least two pins extending from or through the bottom surface of the pin protection block tool assembly are configured to register the pin protection block tool assembly in fixed lateral alignment with the holes of the vacuum drying station 176. The pins serve to secure the pin protection block tool assembly to the vacuum drying station 176, for use in selectively displacing one or more pins in the pin too head assembly 64. Pin protection block tool assembly body 610 also has spacing element 612 which fits into the channel machined into vacuum drying station 176 (see FIG. 7) that allows proper orientation and fitting of the pin protection block tool assembly for selectively displacing one or more pins in the pin too head assembly 64. Spacing element 612 acts as a keying feature such that the pin protection block assembly may only be inserted in one orientation, thus preventing the user from incorrectly mounting the pin protection block assembly and potentially damaging the pin tools 68 or the pin tool head 64. The pin protection block tool assembly embodiment may be machined from a monolithic block of a strong stable material, such as polymers, such as Delrin®, composites and metals, such as stainless steel, aluminum, which may be anodized, and the like.

Figure 42:
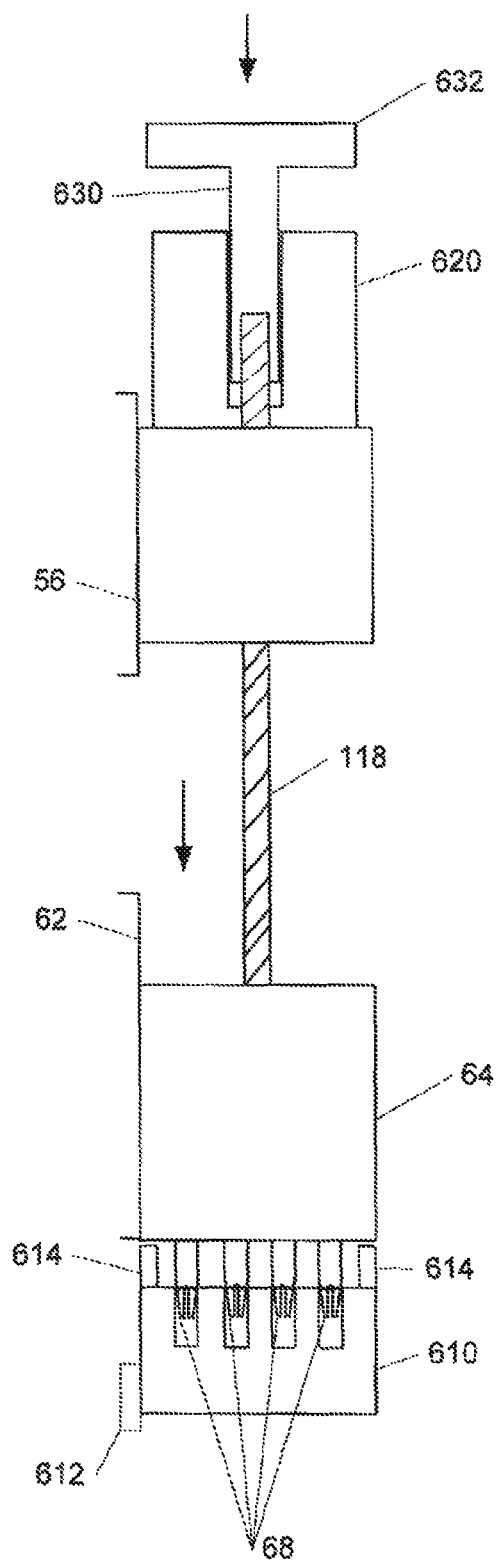
FIG. 42 illustrates the functional coupling of components which enable selective displacement of pin tools in the pin tool head.

The regularly spaced cylindrical bores in the upper surface of the pin protection block tool assembly may be of sufficient diameter to allow a lower part of the tapered portion 158 and slotted tip 162 of pin tool shaft 142 to enter the opening, yet narrow enough for the upper tapered portion of pin tool shaft 142 to come to rest against the edge and inner wall surface of the cylindrical bores in the pin protection block tool assembly (see FIG. 42). The pin tools resting on an upper part of the tapered portion 158 of slotted pin too tip 162 may prevent damage to the lower slotted portion of the pin tool 68, by focusing downward pressure on the sturdier upper part of the tapered portion 158 of pin tool 68. The diameter of pin protection block tool assembly holes maybe in the range of about 0.01 to about 0.1 inches, and more specifically in the range of about 0.05 to about 0.06 inches in diameter. The depth of the holes in the pin protection block tool assembly maybe greater than the length of the tapered portion of the pin tool shaft, such that when the pin tool head assembly 64 comes to rest on the raised edges 614 of the pin protection block tool assembly body 610, the pin tools 68 may be suspended above the bottom of the machined holes and the pin tools may be held in place by contact an upper part of the tapered portion 158 of pin tool shaft 142 and the edges of the cylindrical bores in the pin protection block tool assembly body. The depth of the non-penetrating cylindrical bores of the pin protection block tool assembly may be in the range of about 0.1 to about 1 inch and more specifically in the range of about 0.3 to about 0.4 inches in depth.

In some embodiments, the pin protection block tool assembly is used in conjunction with a plunger mechanism assembly, as shown in FIGS. 38A-38B and 39A-39B. The plunger mechanism assembly may be useful for downward displacement of the z-axis carrier and pin tool assembly which translates to upwards axial displacement of the pin tools 68, relative to pin tool head 64, to allow insertion of various comb insert blocks, which allow the selective displacement of one or more pin tools 68 in a pin tool head assembly 64. The plunger mechanism assembly includes a collar 620 and plunger handle 630.

Figure 38A:
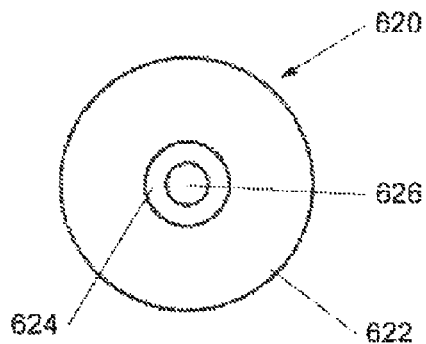
FIG. 38A is a top view of an outer collar for use with a plunger mechanism embodiment.
Figure 38B:
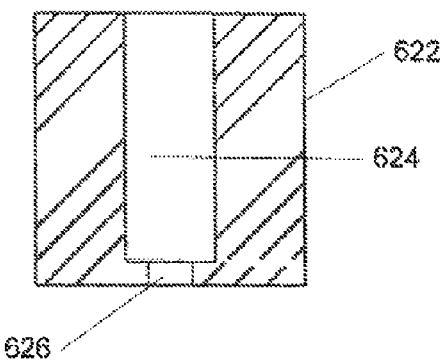
FIG. 38B is a cross section view of an outer collar for use with a plunger mechanism embodiment.

Referring now to FIGS. 38A-38B, plunger mechanism collar 620 is substantially cylindrical with a central concentric stepped cylindrical bore in the material of the collar. The plunger mechanism assembly embodiment may be machined from a monolithic block of a strong stable material, such as polymers, such as Delrin®, composites and metals, such as stainless steel, aluminum, which may be anodized, and the like. The outer diameter 622 of the plunger mechanism collar may be in the range of about 0.5 to about 3 inches and more specifically in the range of about 1.5 to about 2 inches in diameter. The central concentric stepped cylindrical bore has two different diameters (624, 626), which when viewed from a top down position assumes the configuration shown in FIG. 38A. The larger of the two inner diameters 624 may be machined to a depth from the top of the collar in the range of about 1.20 to about 1.45 inches, and more specifically about 1.35 to about 1.39 inches. The diameter of this larger of the inner bores may be in the range of about 0.1 to about 1 inch and more specifically in the range of about 0.4 to about 0.6 inches. The smaller of the two diameters 626 may be formed from the bottom of the larger diameter to the bottom of the collar forming an opening with a diameter in the range of about 0.1 to about 0.4 inches and more specifically in the range of about 0.23 to about 0.27 inches in diameter. Plunger mechanism assembly collar 620 allows functional coupling to both the plunger 630 of the plunger mechanism assembly and the threaded rod 118 of the z-axis translatable carrier 56, which carries pin tool assembly 64. In some embodiments plunger mechanism collar 620 functions as an additional positional stop to prevent over compressing the axial springs 152 or the pin tool tips 156 of the pin tools. In some embodiments plunger mechanism collar 620 functions as a guide to prevent lateral displacement of the threaded shaft 118, thus minimizing the potential for damage to the z-axis translatable carrier mechanism by bending or flexing threaded shaft 118, during axial displacement. In some embodiments plunger mechanism 620 provides both functions.

Figure 39A:
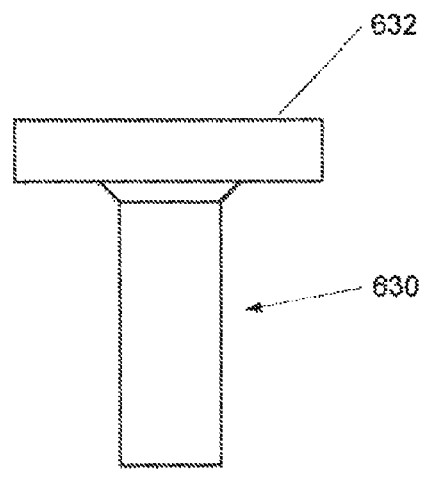
FIG. 39A is a front view of a plunger handle for use with a plunger mechanism embodiment.
Figure 39B:
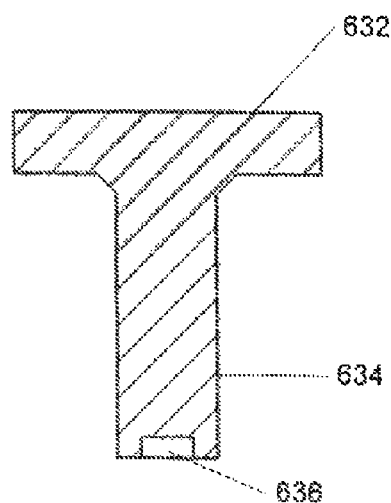
FIG. 39B is a cross section view of a plunger handle for use with a plunger mechanism embodiment.

Referring now to FIG. 39A-39B, plunger 630 of the plunger mechanism assembly may be configured to allow fitment into plunger mechanism assembly collar 620. Plunger 630 may be in the range of about 1 to about 4 inches in height, and more specifically in the range of about 1.55 to about 1.85 inches in height. Plunger 630 may be formed with a main shaft 634 with a diameter in the range of about 0.3 to about 0.7 inches, and more specifically in the range of about 0.4 to about 0.6 inches in diameter. This main shaft enlarges to a cylindrical plunger handle 632 with a diameter in the range of about 0.5 to about 3.0 inches and more specifically in the range of about 1.5 to about 2 inches in diameter. The base of the plunger handle shaft 634 contains a cylindrical bore 636 with a diameter in the range of about 0.1 to about 0.4 and more specifically in the range of about 0.23 to about 0.27 inches in diameter. The depth of cylindrical bore 636 may be in the range of about 0.01 to about 0.2 inches and more specifically in the range of about 0.08 to about 0.12 inches in depth. The plunger mechanism assembly handle 630 may be so configured to allow functional coupling to both the plunger mechanism assembly collar 620 and the threaded rod 118 of the z-axis translatable carrier 56, which carries pin tool assembly 64.

FIG. 38B is a cross sectional view of the central concentric stepped cylindrical bore of the plunger mechanism collar 620 which shows where the plunger handle 630 and the threaded rod 118 of z-axis translatable carrier 56 are brought into functional coupling in the interior of collar 620 of the plunger mechanism assembly. In some embodiments the plunger mechanism assembly may be assembled and functionally coupled to the threaded shaft 118 of z-axis translatable carrier 56 to enable upwards axial displacement of the pin tool tools 68, relative to the pin tool head 64, to allow insertion of various comb insert blocks, enabling the selective displacement of one or more pin tools 68 in a pin tool head assembly 64. As described previously, the pin tool head assembly 64 may be placed on a hard surface with the tips of the pin tools resting directly on the hard surface (see FIG. 18 and FIG. 19). For some embodiments the comb insert block assembly may be used to suspend the tips of the pin tools 68 over the machined cylindrical bores of the comb insert block assembly with the main shaft of the pin tools 68 supporting the pin tools as the threaded collar 118 in functional contact with pin tool head assembly 64 may be depressed using the plunger mechanism assembly functionally coupled to the threaded shaft 118 or z-axis translatable carrier 56, causing the upwards axial displacement of the pin tool collar member 143, relative to the pin tool head 64. Use of the comb insert block assembly reduces the possibility of damage to the pin tools 68 by eliminating placing the tapered portion 158 and slotted tip 162 of pin tool shaft 142 in direct contact with a hard surface.

As described previously, it may be desirable to selectively alter the number of pins being used in the pinhead tool 64, without physically changing out the pinhead tool. For some embodiments, a method for selectively displacing at least one pin tool 68 of a pin tool head assembly 64 of a robotic sample transfer device 10 may optionally include providing a pin protection block tool assembly and a plunger mechanism assembly in addition to the pin tool insert block. Such a method embodiment may be initiated using the user interface 26 and navigating the various programming controls of device 10. The commands for altering pin tool configuration are located in the "Maintenance Screen" accessed from the main menu. Once in the "Maintenance Screen", the "Change Insert" button may be selected to initiate the method for selectively displacing at least once pin tool 68 in the pin tool head assembly 64.

Upon program initiation, the pin tool head may be moved away from the vacuum drying station 176 of the cleaning and drying portion of device 10, facilitating removal of any vacuum plates or calibration wells, and allowing positioning of the pin protection block tool assembly. The pin protection block tool body 610 of the pin protection block tool assembly may be positioned using the aligning element 612 and pins 616. Pins 616 are reversibly operationally coupled with holes in the vacuum drying station 176. Once the pin protection block tool assembly is in place, "Continue" may be selected using the user interface 26 and device 10 moves pin tool head 64 over the pin protection block tool assembly. Pin tool head 64 is automatically lowered approximately 5 mm, placing the narrowest part of the tapered portion 158 of pin tools 68 within the cylindrical bores of the pin protection block tool assembly. The user may then functionally couple the plunger mechanism to the threaded shaft 118, and apply downward pressure to compress the pin tool head 64 the remaining distance to bring the bottom plate 139 of pin tool head 64 in contact with pin protection block assembly raised edges 614, as illustrated in FIG. 42. FIG. 42 illustrates the functional coupling of the comb insertion block assembly, pin tool head 64, threaded shaft 118, Z-axis step motor 126, y-axis translatable carrier 62, z-axis translatable carrier, plunger mechanism collar 620, and plunger 630, all used in concert to allow selective displacement of pin tools 68 in a pin tool head 64. Downward pressure, as shown by the downward arrow in FIG. 42, may be applied to plunger 630 through plunger handle 632 which pushes pin tools 68 against the pin protection block tool assembly which in turn serves to push the pin tool collars 143 up, relative to pin tool head 64, allowing the insertion of a pin tool insert comb. After the pin tool comb insert (336 or 360) is inserted, the plunger mechanism assembly may be removed, which allows the pin tool head to come back to a relaxed state. "Continue" may be selected on the user interface 26, and device 10 completes the pin tool selection program. In some embodiments, device 10 may provide the user with visual prompts. In some other embodiments device 10 may provide the user with auditory prompts. In yet other embodiments, device 10 may provide the user with video clips showing the procedure being performed. In some embodiments device 10 may provide a combination of visual prompts, auditory prompts, and video clips to aid the user in completing the pin tool displacement block insert procedure.

As previously described and illustrated in FIGS. 20A-20D and FIGS. 21A-21D, pin tool displacement blocks may be used that enable the selective displacement of one or more pin tools 68 in a pin tool head assembly 64. FIGS. 35A-35D and FIGS. 36A-36D illustrate embodiments of pin tool displacement blocks. Pin tool comb 336' and 360' of FIGS. 35A-35D and 36A-36D may have features, dimensions, or materials that are the same or similar to those of 336 and 360 in FIGS. 20A-20D and 21A-21D. Additionally the methods useable for insertion of the previously described and illustrated pin tool displacement blocks maybe the same as the methods used to insert the additional embodiments of the pin tool displacement blocks.

Referring now to FIG. 35A-35D, in some embodiments a pin tool comb insert allowing the displacement of all but one pin tool 68 is provided. This embodiment of a pin tool displacement block (pin tool comb insert) has raised edges 339 which act as an orientation keying feature which prevents the pin tool displacement block from being inserted incorrectly. That is, raised edges 339 may confer a unidirectional orientation to the pin tool displacement block. Pin tool comb insert 336' may also be configured to have a chamfered forward upper edge to allow the user easier insertion into the pin tool head 64.

Referring now to FIG. 36A-36D, in some embodiments a pin tool comb insert allowing the displacement of all but six pin tools 68 is provided. This embodiment of a pin tool displacement block (pin tool comb insert) has raised edges 363 which act as an orientation keying feature which prevents the pin tool displacement block from being inserted incorrectly. That is, raised edges 363 may confer a unidirectional orientation to the pin tool displacement block. Pin tool comb insert 360' may also be configured to have a chamfered forward upper edge to allow the user easier insertion into the pin tool head 64.

While pin tool displacement blocks have been described herein for applications that selectively displace all but one or all but 6 pin tools, pin tool numbers other than 1, 6 or 24 maybe used. The number and pattern of pin tools selectively displaced and thereby inactivated may be 1, 2, 3, 4, 5, 6, 7 . . . . up to 23, when using a 24 pin tool head. This may be achieved by an alternative configuration of pin tool displacement blocks, and the disclosure herein is not meant to limit the embodiments contemplated to 1, 6, or 24 active pin tools 68.

In some embodiments where the number of pin tools being actively used has been selectively altered, a dry station plate assembly may be provided that may be configured to correspond to the pattern of the pin tools selected to be active. The dry station plate assembly allows for selective use of the vacuum drying station 176 vertical holes 178 as drying orifices. This allows the user to direct the vacuum to only those pin tools 68 actively being used in any particular application. The dry station plate assembly may be machined from a monolithic block of a strong stable material, such as polymers, such as Delrin®, composites and metals, such as stainless steel, aluminum, which may be anodized, and the like. The dry station plate assembly may also be cut or machined from Lucite®, polycarbonates, acrylic and the like. Dry station plate assemblies for any number of openings corresponding to a desired number of selectively activated pin tools 68 are contemplated herein as well as the embodiments described below. In general the dry station plate assembly (640, 650) may be substantially rectangular in shape, the size and shape corresponding with the size and shape of pin tool head 64. The height of the dry station plate assembly body (642, 652) may be in the range of about 0.01 to about 1 inch, more specifically in the range of about 0.1 to about 1 inch and most specifically be in the range of about 0.2 to about 0.5 inches in height. The dry station plate assemblies may have at least 3 holes machined through the body to allow insertion of seating pin dowels, the holes being of sufficient diameter to allow the use of pin dowels (644, 654) that fit within the nominal diameter of the vacuum dry station 176 vertical holes 178, and allow functional coupling of the dry station plate assembly to the vacuum drying station. The use of dry station plate assemblies may reduce the waste of vacuum in the vacuum holding tank by channeling vacuum to only the openings 178 that correspond to active pin tools 68, and blocking off all other openings through which vacuum might be wasted. Additionally, if the unused holes are not blocked using the dry station plate assemblies, all vacuum flow will be through the unblocked holes and minimal flow will be through the holes containing pin tools. This may cause the pins to not be sufficiently dried, which in turn may lead to cross contamination of samples.

Figure 40A:
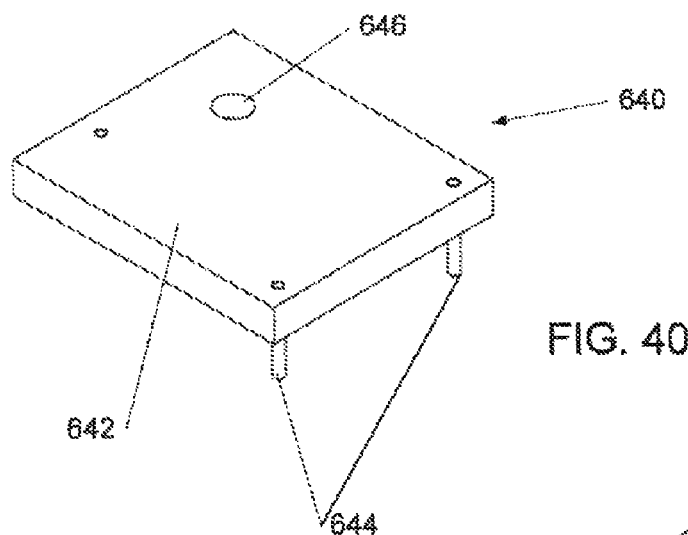
FIGS. 40A-40C illustrate an embodiment of a dry station plate assembly, single in configuration.
Figure 40B:
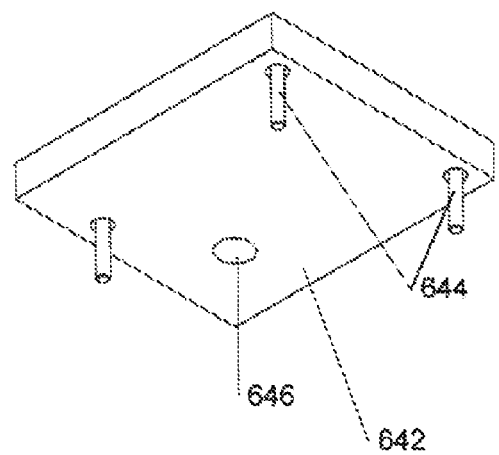
Figure 40C:
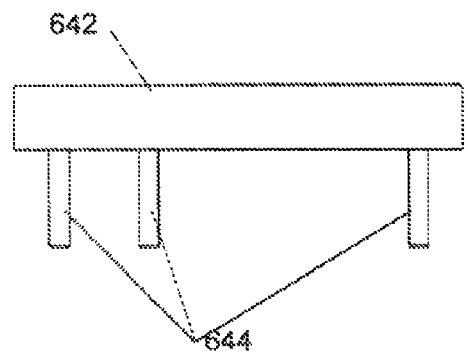

Referring now to FIGS. 40A-40C, in some embodiments a vacuum drying station plate assembly 640 which blocks all but one vertical hole 178 in the vacuum drying station 176 is provided. Vacuum drying station plate assembly 640 includes plate body 642, pin dowels 644 and pin tool opening 646. The embodiment of dry station plate assembly 640 may be used in conjunction with the pin tool insert comb that selectively displaces or deactivates all but one pin tool 68.

Referring now to FIGS. 41A-41C, in some embodiments a vacuum drying station plate assembly 650 which blocks all but six vertical holes 178 in the vacuum drying station 176 is provided. Vacuum drying station plate assembly 650 includes plate body 652, pin dowels 654 and pin tool openings 656. The embodiment of dry station plate assembly 650 may be used in conjunction with the pin tool insert comb that selectively displaces or deactivates all but six pin tools 68.

In general, a wide variety of techniques can be implemented consistent with the principles the invention and no attempt is made herein to describe all possible techniques. With regard to the above detailed description, like reference numerals used therein refer to like elements that may have the same or similar dimensions, materials and configurations. While particular forms of embodiments have been illustrated and described, various modifications can be made without departing from the spirit and scope of the embodiments of the invention. Accordingly, it is not intended that the invention be limited by the forgoing detailed description.

What is claimed is:

1. A robotic sample transfer device, comprising:
a substantially horizontal work surface including a plurality of functional elements configured for small sample processing;
a three axis robotic positioning assembly having a fixed mount portion secured in fixed relation with the work surface,
a translatable carrier configured to be translatable in three different axes with respect to the fixed mount portion and work surface, which translatable carrier comprises three stepper motors each corresponding to each of the three axes and at least one linear encoder assembly configured to generate position data for at least one axis;
a pin tool head assembly coupled to the translatable carrier; the pin tool head assembly comprising a plurality of pin tools configured for displacement along an axis perpendicular to lateral surfaces of the pin tool head assembly, each of which pin tools comprises (i) a shaft that comprises a sample reservoir at a distal end of the shaft, and (ii) a collar around the shaft positioned between a proximal end and the distal end of the shaft;
a pin tool displacement block comprising a plurality of slots and one or more relieved channels in a subset of slots, each of the relieved channels is configured to permit a pin tool shaft and a collar to traverse all or part of the relieved channel, each of which slots is configured to permit a pin tool shaft, but not a collar, to traverse all or part of the slot, and which pin tool displacement block is moveably disposed relative to the pin tool head assembly; and a controller configured to control (i) the stepper motors, (ii) at least one linear encoder assembly, and (iii) movement of the pin tool displacement block into a position that disposes the relieved channels under a first subset of the pin tools for use in sample transfer and does not dispose the relieved channels under a second subset of the pin tools not for use in sample transfer.

2. The robotic sample transfer device of claim 1, further comprising a housing disposed around the work surface, the three axis robotic positioning assembly and the controller.

3. The robotic sample transfer device of claim 2, further comprising a graphic user interface on an exterior of the housing and operatively coupled to the controller, which graphic user interface provides user input to the controller.

4. The robotic sample transfer device of claim 1, wherein the three axes are orthogonal to each other.

5. The robotic sample transfer device of claim 1, wherein the three axis robotic positioning assembly further comprises a bar code reader.

6. The robotic sample transfer device of claim 1, wherein the translatable carrier further comprises an imaging camera translatable in at least two axes and operatively coupled to an image processor.

7. The robotic sample transfer device of claim 2, wherein the controller comprises at least one processor disposed within the housing at a level which is above the level of the work surface.

8. The robotic sample transfer device of claim 1, wherein the slots are parallel.

* * * * *